US012486852B2

(12) United States Patent
Xie et al.

(10) Patent No.: US 12,486,852 B2
(45) Date of Patent: *Dec. 2, 2025

(54) CENTRIFUGAL FAN, NECK FAN, AND VORTEX SHELL ASSEMBLY

(71) Applicants: SHENZHEN JISU TECHNOLOGY CO., LTD, Shenzhen (CN); Xiangfu Li, Shenzhen (CN); Guanzheng Zheng, Shenzhen (CN); Jiahang Xie, Shenzhen (CN)

(72) Inventors: Jiahang Xie, Shenzhen (CN); Guanzheng Zheng, Shenzhen (CN); Xiangfu Li, Shenzhen (CN)

(73) Assignees: SHENZHEN JISU TECHNOLOGY CO., LTD, Shenzhen (CN); Xiangfu Li, Shenzhen (CN); Guanzheng Zheng, Shenzhen (CN); Jiahang Xie, Shenzhen (CN)

( * ) Notice: Subject to any disclaimer, the term of this patent is extended or adjusted under 35 U.S.C. 154(b) by 24 days.

This patent is subject to a terminal disclaimer.

(21) Appl. No.: 19/034,691

(22) Filed: Jan. 23, 2025

(65) Prior Publication Data

US 2025/0163922 A1 May 22, 2025

Related U.S. Application Data

(63) Continuation of application No. 18/244,334, filed on Sep. 11, 2023, which is a continuation of application
(Continued)

(30) Foreign Application Priority Data

Oct. 25, 2019 (CN) ......................... 201921815938.3
Sep. 30, 2020 (CN) ......................... 202022210032.8

(51) Int. Cl.
*F04D 29/42* (2006.01)
*A61F 7/00* (2006.01)
(Continued)

(52) U.S. Cl.
CPC ....... *F04D 25/166* (2013.01); *F04D 29/4213* (2013.01); *F04D 29/424* (2013.01);
(Continued)

(58) Field of Classification Search
CPC ............. F04D 29/4226; F04D 29/4246; A41D 20/005; A42B 3/286; F24F 2221/38; A61F 2007/0009; A61F 2007/001
See application file for complete search history.

(56) References Cited

U.S. PATENT DOCUMENTS 5,802,865 A * 9/1998 Strauss ..................... A61F 7/10
62/259.3
2017/0370596 A1* 12/2017 Lee ........................ A42B 3/286
(Continued)

FOREIGN PATENT DOCUMENTS

KR 20190012600 * 2/2019 ............. F04D 25/08
KR 20170370596 * 4/2019 ............. F04D 25/10

*Primary Examiner* — Andrew J Marien

(57) ABSTRACT

A neck fan is provided and is configured to be worn around a neck of a user. The neck fan includes: a shell, defining a receiving channel; and two centrifugal fans. One of the two centrifugal fans is disposed at an end of the receiving channel, and another one of the two centrifugal fans is disposed at another end of the receiving channel. Each of the two centrifugal fans includes: a plurality of blades, configured to rotate to intake air from an outside of the centrifugal fan to generate wind; and a vortex tongue structure, including a pressurizing plate and a wind guiding plate connected to the pressurizing plate. The pressurizing plate is a curved wall arranged around ends of some of the plurality of blades,
(Continued)

the wind guiding plate protrudes from and is extending away from an outer surface of the pressurizing plate.

10 Claims, 44 Drawing Sheets

Related U.S. Application Data

No. 17/739,081, filed on May 7, 2022, now Pat. No. 11,754,080, which is a continuation-in-part of application No. 17/471,178, filed on Sep. 10, 2021, now Pat. No. 11,661,947, which is a continuation of application No. PCT/CN2020/128564, filed on Nov. 13, 2020.

(51) Int. Cl.

| | |
|---|---|
| ***F04D 25/16*** | (2006.01) |
| *F04D 25/06* | (2006.01) |
| *F04D 29/00* | (2006.01) |

(52) U.S. Cl.

CPC .. *F04D 29/4246* (2013.01); *A61F 2007/0011* (2013.01); *A61F 2007/0067* (2013.01); *F04D 25/0673* (2013.01); *F04D 29/005* (2013.01)

(56) References Cited

U.S. PATENT DOCUMENTS

2020/0187574 A1* 6/2020 Te Hsiang ......... A41D 13/0053
2021/0310718 A1* 10/2021 Zeng ......................... F25D 7/00
2021/0355963 A1* 11/2021 Kang .................... F04D 29/281

* cited by examiner

CENTRIFUGAL FAN, NECK FAN, AND VORTEX SHELL ASSEMBLY

CROSS-REFERENCE TO RELATED APPLICATIONS

The present application is a continuation application of the U.S. patent application Ser. No. 18/244,334, filed on Sep. 11, 2023. The U.S. patent application Ser. No. 18/244,334 is a continuation application of U.S. patent application Ser. No. 17/739,081. The U.S. patent application Ser. No. 17/739,081 is a continuation-in-part of U.S. patent applicant Ser. No. 17/471,178, filed on Sep. 10, 2021, which claims priorities of Chinese patent application No. 202022210032.8 filed on Sep. 30, 2020, and the Chinese patent application No. 201921815938.3, filed on Oct. 25, 2019. Contents of the applications are incorporated herein by reference in their entireties.

TECHNICAL FIELD

The subject matter herein generally relates to fans, and particularly relates to a fan hanging around a neck, a centrifugal fan, and a vortex shell assembly.

BACKGROUND

Fans in the art may include fixed and portable fans. Fixed fans, such as floor fans, desktop fans and wall-mounted fans, are fixed in a certain place, and people may be cooled if staying within an air supply area. However, the fans cannot be carried around. Portable fans are available in the art but tend to have a single structure and a fixed shape. The user may be uncomfortable when wearing the fix-shaped portable fan, and have a poor experience when wearing the fix-shaped portable fan for a long period of time.

SUMMARY OF THE INVENTION

In a first aspect, a neck fan is provided and is configured to be worn around a neck of a user. The neck fan includes: a shell, defining a receiving channel; and two centrifugal fans. One of the two centrifugal fans is disposed at an end of the receiving channel, and an other one of the two centrifugal fans is disposed at an other end of the receiving channel. Each of the two centrifugal fans includes: a plurality of blades, configured to rotate to intake air from an outside of the centrifugal fan to generate wind; and a vortex tongue structure, including a pressurizing plate and a wind guiding plate connected to the pressurizing plate. The pressurizing plate is a curved wall arranged around ends of some of the plurality of blades, the wind guiding plate protrudes from and is extending away from an outer surface of the pressurizing plate.

BRIEF DESCRIPTION OF THE DRAWINGS

Implementations of the present disclosure will now be described, by way of embodiment, with reference to the attached figures. It should be understood, the drawings are shown for illustrative purpose only, for ordinary person skilled in the art, other drawings obtained from these drawings without paying creative labor by an ordinary person skilled in the art should be within scope of the present disclosure.

DETAILED DESCRIPTION

Figure 1:
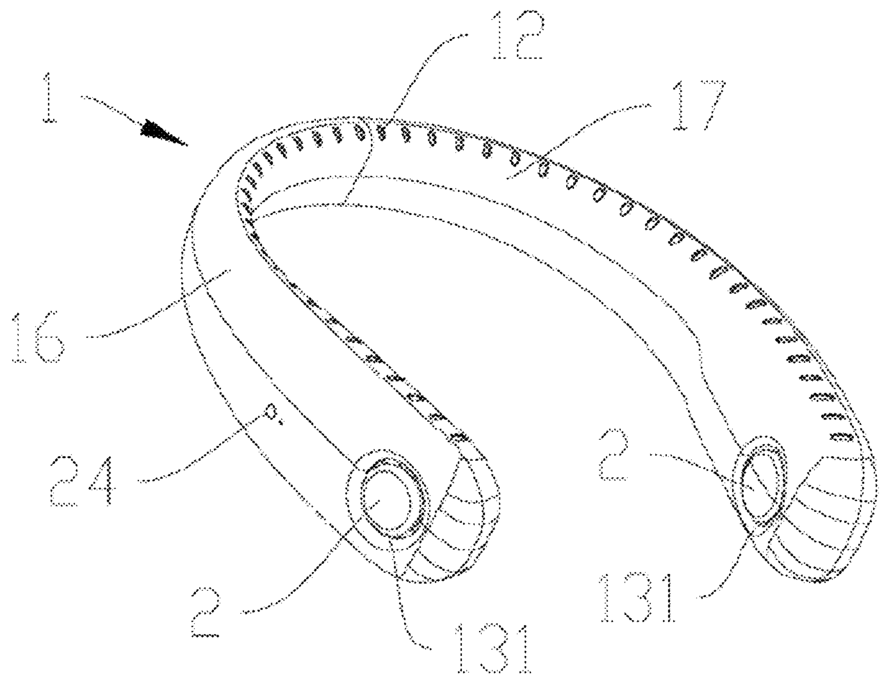
FIG. 1 is a schematic view of a neck fan according to an embodiment of the present application.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term “comprising” when utilized, means “including, but not necessarily limited to”; it specifically indicates open-ended inclusion or membership in the so-described combination, group, series, and the like. The disclosure is illustrated by way of example and not by way of limitation in the figures of the accompanying drawings in which like references indicate similar elements. It should be noted that references to “an” or “one” embodiment in this disclosure are not necessarily to the same embodiment, and such references can mean “at least one”. In addition, the terms “first” and “second” are used for descriptive purposes only and cannot be understood as indicating or implying relative importance or implying the number of indicated technical features. Thus, the features defined as “first” and “second” may explicitly or implicitly include one or more of the said features. In the description of embodiments of the invention, “a plurality of” means two or more, unless otherwise specifically defined.

Figure 2:
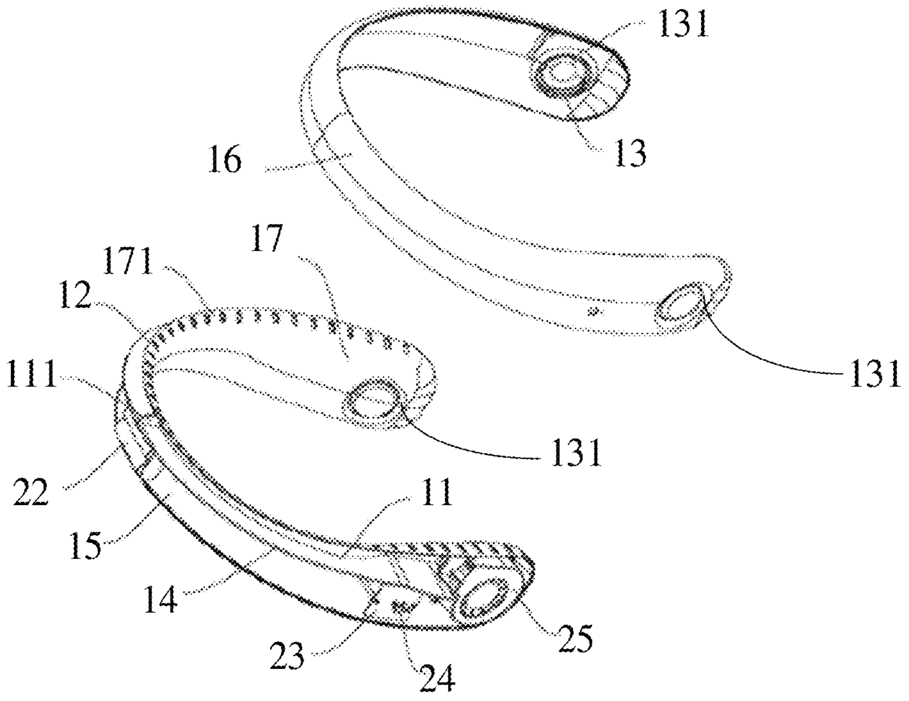
FIG. 2 is an explosive view of a neck fan according to an embodiment of the present application.

In an embodiment, as shown in FIGS. 1 and 2, the present disclosure provides a neck fan including a body portion 1 and a fan assembly 2. The body portion 1 may be worn around a neck of a user. The body portion 1 defines an air duct 11. The body portion 1 defines a plurality of air outlets 12 communicating with the an outside of the neck fan and the air duct 11. In this way, air in the air duct 11 may flow to the outside through the air outlets 12. The fan assembly 2 is mounted on the body portion 1 and is configured to drive the air from the outside into the air duct 11 and blow the air to the outside through the air outlets 12. The air driven into the air duct 11 through fan assembly 2 has a certain speed. Therefore, a wind pressure difference is present between an inside and the outside of air outlets 12, i.e., between the air duct and the outside. In this case, while the air is being blown to the outside through the air outlets 12, due to the wind pressure difference, some of the air in the air duct 11 may flow out of the air duct 11 through air outlets 12 to reach the neck to cool the user. In an embodiment, the plurality of air outlets 12 are evenly distributed and spaced apart from each other. Therefore, when being worn, the body portion 1 surrounds a front, a side and a back of the neck, and the air blown out from the air outlets 12 may be directed to the front, the side and the back of the neck. In this way, a range that the air may reach is expanded, and the user may be cooled from various directions. The neck fan is highly applicable and may be used conveniently.

As shown in FIG. 1, the body portion 1 may be bent and tubular and may be made of an elastic material that can be extended and retracted. When putting on the body portion, two ends of the body portion 1 may be pulled apart from each other to form a gap, and a size of the gap may be greater than a size (such as a diameter) of the neck. After the neck fan is worn to the neck, the body portion may be reset, i.e., the two ends may be reset to original positions, and the gap between the two ends of the body portion may be reduced. In some embodiments, when the two ends are at the original positions, the two ends may be spaced apart from each other, and a size of the gap therebetween may be less than the size of the neck. In some embodiments, when the two ends of the body portion are at the original positions, the two ends may be connected to each other, such that the body portion is ring-shaped (such as forming an enclosed circle). The body portion 1 may be made of plastic. The user may carry the body portion easily and may feel comfortable when wearing the body portion. The air outlets 12 are oriented towards an inside and/or a top of the bent and tubular body portion. Therefore, while being worn, the neck does not cover the air outlets 12, allowing the air to be blown out the air outlets 12 to the neck smoothly. In detail, some of the air outlets 12 defined in the body portion 1 are oriented towards the inside of the tubular body portion, and some of the air outlets 12 are oriented towards the top of the tubular body portion 1, increasing a range covered by the air supplied from the air outlets 12.

Figure 3:
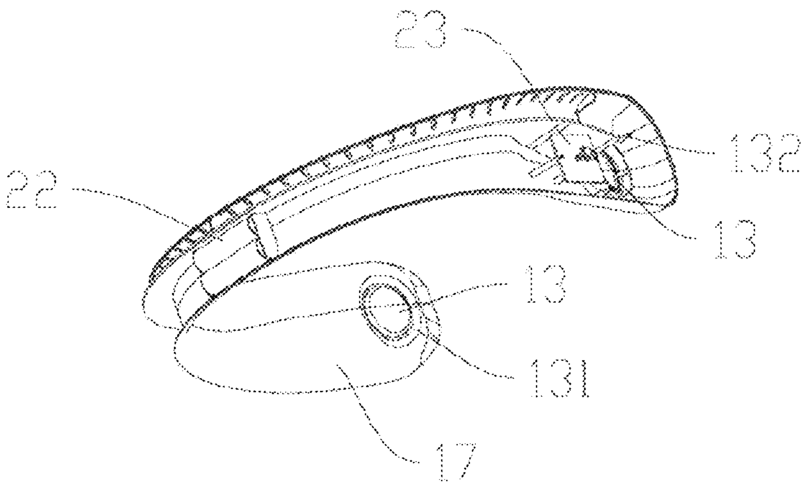
FIG. 3 is a schematic view of an inner shell of a neck fan according to an embodiment of the present application.

As shown in FIGS. 1 to 3, each of two ends of the body portion 1 defines a mounting cavity 13. The fan assembly 2 is received in the mounting cavity 13 to be mounted with the body portion 1. A portion of the body portion 1 corresponding to the mounting cavity 13 defines an air inlet 131. The fan assembly 2 is fixedly received in the mounting cavity 13. When the fan assembly 2 is operating, the fan assembly 2 draws in the outside air through the air inlet 131, and is configured to accelerate the air to drive the air to flow into the air duct 11. In the present embodiment, two ends of the body portion 1 define two mounting cavities 13, and two fan assemblies 2 may be received in the two mounting cavities 13, respectively. Each of the two fan assemblies 2 may operate independently. A plate 111 may be arranged in a middle of the air duct 11 to divide the air duct 11 into two sections. One of the two sections of the air duct 11 corresponds to one of the two fan assemblies 2. By arranging the plate 111, a length of the air duct 11 may be reduced effectively, ensuring an air velocity at an air outlet 12, which is further away from the fan assembly 2.

Figure 4:
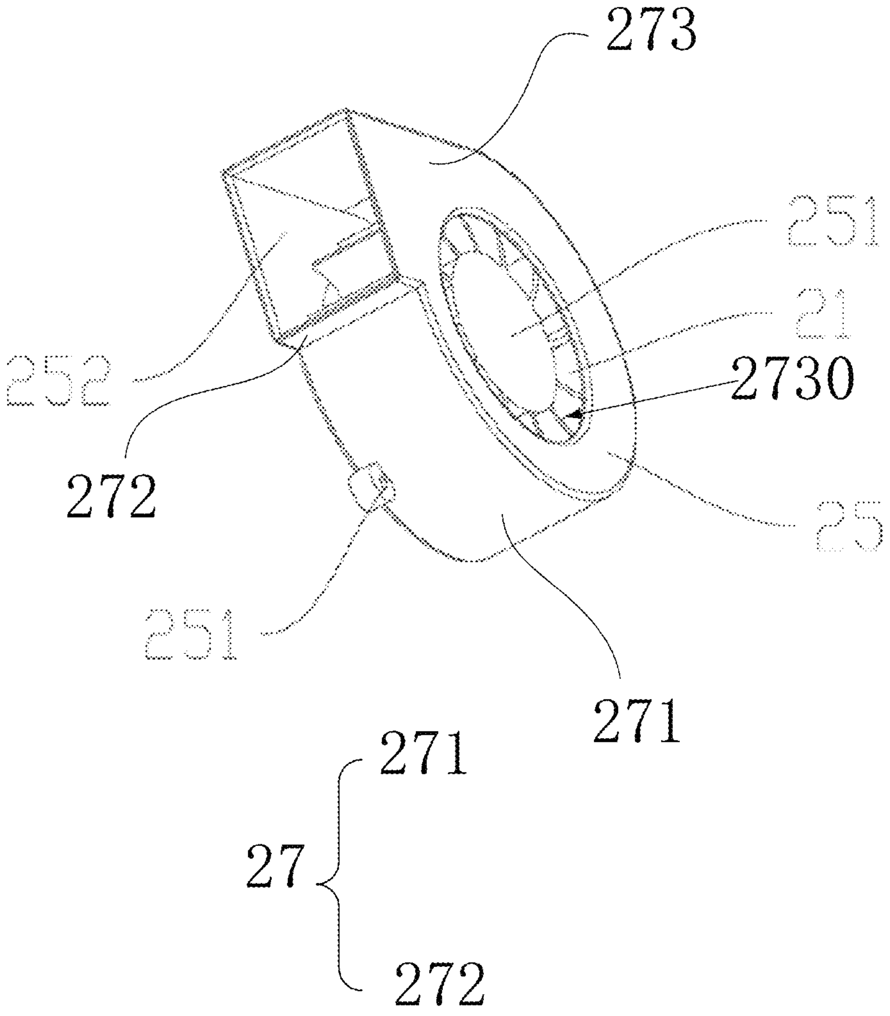
FIG. 4 is a schematic view of a turbo fan of a neck fan according to an embodiment of the present application.

As shown in FIGS. 2 and 4, the fan assembly 2 includes a fan blade 21, a motor (not shown in the figures) which drives the fan blade 21 to rotate to generate an air flow, a battery 22 which provides power to the motor, a main control circuit board 23 which controls a rotation speed of the motor, and a gear switch 24 electrically connected to the main control circuit board 23. When the neck fan needs to be initiated, the gear switch 24 may be pressed, and the main control circuit board 23 may receive a signal from the gear switch 24. After receiving the signal, the main control circuit board 23 controls the motor to rotate to drive the fan blade 21 to rotate. Rotation of the fan blade 21 may lead the air at the outside to flow into the fan assembly 2 under the wind pressure, and the air may be guided by the fan assembly 2 to flow into the air duct 11. When the wind speed of the air flowing out of the air outlets 12 needs to be adjusted, the gear switch 24 may be pressed to generate various gear signals. The main control circuit board 23 may receive the gear signals and control the rotation speed of the motor to further control the rotation speed of the fan blade 21 connected to the motor. Accordingly, a speed of the air driven by the fan assembly 2 to flow into the air duct 11 and a speed of the air flowing out through the air outlets 12 may change. A partition 14 may be arranged inside the body portion 1. The partition 14 separates an inner space of the body portion 1 into a shaped cavity 15 and the air duct 11. The battery 22 and the circuit board both are received in the shaped cavity 15. The battery 22 may be disposed in a middle of the inner space of the body portion 1. In this way, the fan assemblies 2 are arranged at the two ends of body portion 1, whereas the battery 22 is arranged at the middle of the body portion 1, the two ends of the body portion 1 may not be too heavy, and weights of the two ends of the body portion 1 may be balanced, preventing a weight center of the body portion 1 from being shifted towards one side.

As shown in FIG. 2, a cross-sectional area of the air duct 11 gradually decreases from the two ends to the middle of the body portion 1. The air flowing from the two ends to the middle of the body portion 1 may generate a frictional force. At the same time, the cross-sectional area of the air duct 11 decreases from the two ends to the middle of the body portion 1, i.e., the cross-sectional area that the air passes through while flowing in the air duct 11 decreases. In this way, an effect of the frictional force on slowing down the speed of the air flow in the air duct 11 may be partially or completely eliminated. The speed of the air flowing out of the air outlets 12 may be controlled within a certain range, solving a problem of a large difference between the speed of the air flowing out of an air outlet 12 at or near the two ends of the air duct 11 and the speed of the air flowing out of an air outlet 12 in the middle of the air duct 11.

As shown in FIG. 2, the body portion 1 includes an outer shell 16 and an inner shell 17. Compared to the body portion 1 configured as a one-piece structure, the body portion 1 of the present embodiment is assembled from the outer shell 16 and the inner shell 17, allowing the fan assemblies to be processed and assembled more simply, and allowing later maintenance to be performed more easily. The partition 14 is arranged on the inner shell 17 and extends towards the outer shell 16. The air duct 11 is defined cooperatively by the inner shell 17, the outer shell 16 and the partition 14. When the outer shell 16 is connected to the inner shell 17, the partition 14 tightly abuts against an inner side of the outer shell 16, preventing the air in the air duct 11 from entering the shaped cavity 15. The air outlets 12 are defined in the inner shell 17. A portion of the inner shell 17 that contacts the neck of the user extending upwardly to form a curved surface 171. The curved surface 171 may be inclined at a certain angle relative to the portion that contacts the neck of the user, and the air outlets 12 are defined in the curved surface 171, such that the air outlets 12 are oriented towards the inner side of the tubular body portion.

As shown in FIGS. 2 and 4, the fan assembly 2 includes a turbine fan 25. The turbine fan 25 defines two inlet windows 251, increasing a circulation area and an efficiency of the turbine fan 25 communicating with the external air. A cavity wall of the mounting cavity 13 defines two air inlets 131 corresponding to the two inlet windows 251 of the turbine fan 25. When the turbine fan 25 is rotating, the external air may enter the inlet windows 251 through the air inlets 131. A guide post 132 is arranged on the cavity wall of the mounting cavity 13 and extends towards the turbine fan 25. The turbine fan 25 defines a guide hole 253 corresponding to the guide post 132. When the turbine fan 25 is received in the mounting cavity 13, the guide post 132 extends into the guide hole 253, thereby securing the turbine fan 25 in the mounting cavity 13.

As shown in FIG. 4, the turbine fan 25 defines an air outlet port 252, which is corresponding to and communicating with the air duct 11. An air flow generated by the turbine fan 25 enters the air duct 11 through the air outlet port 252. A portion of a wall of the air outlet port 252 is received in the air duct 11. The portion of the wall of the air outlet port 252 tightly abuts against a wall of the air duct 11, reducing a loss of the air flow generated by the turbine fan 25 while the air is being guided into the air duct 11.

In an embodiment, as shown in FIG. 4, a centrifugal fan is arranged in the neck fan of the present disclosure and serves as the turbine blade assembly. The centrifugal fan includes a motor, a plurality of blades 21, and a vortex tongue structure 27. The blades 21 may be driven by the motor to rotate to intake air from an outside of the centrifugal fan to generate wind. The vortex tongue structure 27 includes a pressurizing plate 271 and a wind guiding plate 272 connected to the pressurizing plate 271. The pressurizing plate 271 covers at least some of the blades 21. The wind guiding plate 272 has an air channel configured to outlet wind generated by the blades 21. The wind guiding plate 272 protrudes from the pressurizing plate 271 and is extending away from the blades 21.

In detail, the pressurizing plate 271 is a curved wall arranged around ends of the some of the plurality of blades 21. The centrifugal fan includes two side walls 273 connected to two opposite edges of the curved wall. The curved wall and the two side walls 273 cooperatively define a receiving space. The blades 21 are received in the receiving space. The curved wall surrounds ends of the some blades away from the motor. The two side walls 273 cover two sides of each of all blades. The two sides of the blade refer to sides disposed near the air inlets. Each of the two side walls 273 defines an air inlet hole 2730 corresponds to the air inlet window 251 of the blades 21. The blades 21 are configured to rotate to intake air from the air inlet window 251 of each of the two side walls 273.

In another embodiment, the centrifugal fan includes a first wind guiding sub-plate, a second wind guiding sub-plate opposite to the wind guiding sub-plate, a third wind guiding sub-plate connected between the first wind guiding sub-plate and the second wind guiding sub-plate, and a fourth wind guiding sub-plate connected between the first wind guiding sub-plate and the second wind guiding sub-plate and opposite to the third wind guiding sub-plate. The first wind guiding sub-plate, the second wind guiding sub-plate, the third wind guiding sub-plate, and the fourth wind guiding sub-plate cooperatively define the air channel communicating with the receiving space. The blades are configured to generate wind from the air taken in from the air inlet window, the pressurizing plate 271 is configured to guide the generated wind to flow to the air channel from the rest of the plurality of blades uncovered by the pressurizing plate. A direction to which an opening of the air channel faces is perpendicular to a direction along which the air is taken in into the receiving space through the air inlet windows. Further, ends of the rest of the plurality of blades away from the motor are exposed from the opening of the air channel.

The first wind guiding sub-plate acts as the wind guiding plate 272 and may be connected to an end of the curved wall of the pressurizing plate 271 and extending away from the two side walls 273. The second wind guiding sub-plate may be connected to the other end of the curved wall and extending parallel to the first wind guiding sub-plate. The third wind guiding sub-plate may be connected to one of the two side walls 273, and the fourth wind guiding sub-plate may be connected to the other one of the two side walls 273.

In an embodiment, the first wind guiding sub-plate may be extending inclined relative to the end portion of the curved wall near the first wind guiding sub-plate. The second wind guiding sub-plate may be extending from the other end portion of the curved wall disposed near the second wind guiding sub-plate. The second wind guiding sub-plate and the other end portion of the curved wall disposed near the second wind guiding sub-plate may be extending on a same plane or may be inclined relative to each other. The present disclosure does not limit an angle between the second wind guiding sub-plate and the other end portion of the curved wall disposed near the second wind guiding sub-plate.

By connecting the pressurizing plate 271 with the wind guiding plate 272, the air channel may be communicating with the receiving space. A direction to which an opening of the air channel faces is substantially perpendicular to a direction along which the air is taken in into the receiving space through the air inlet windows. The wind guiding plate 272 may be connected to the pressurizing plate 271 by a connecting member, such as screws, snaps, or adhesives; alternatively, the wind guiding plate 272 and the pressurizing plate 271 may be configured as a one-piece and integral structure.

In the present embodiment, the blades may generate wind based on the air taken in from the air inlet windows 251. Since at least some of the blades are surrounded by the curved wall of the pressurizing plate 271, the generated wind cannot flow out of the blades from the at least some of the blades but may flow out of (leave) of the blades from those blades that are not surrounded or blocked by the curved wall. In this way, the wind generated by the blades are pressurized, i.e., the wind may flow out of the blades 21 at a higher speed.

The opening of the air channel of the centrifugal fan may be communicated with the air duct 11. Therefore, the air duct 11, the air channel, and the receiving space are communicated with each other. Specifically, at least a part of the wind guiding plate 272 is connected to the partition 14, such that wind, that is generated by the blades and flow out of the blades, may flow into the air duct. In some embodiments, as shown in FIG. 4, a gap may be defined between the end of the partition 14 near the centrifugal fan and the wind guiding plate 272. Therefore, some of the wind may flow into the shaped cavity 15 through the gap to dissipate heat generated by the battery and other components received in the shaped cavity 15.

In some embodiments, a vortex shell assembly is provided and includes a pressurizing portion and an air guiding portion. The pressurizing portion includes a pressurizing plate and two side walls connected to two opposite sides of the pressurizing plate. The pressurizing plate may surround ends of some of a plurality of blades. The plurality of blades are configured to intake air from the two opposite sides of the pressurizing plate and generate wind from the intake air. The pressurizing portion is configured to pressurize the wind generated by the blades and to guide the pressurized wind to flow to an air outlet.

The air guiding portion is connected to the pressurizing portion and protruding from and extending away from an outer surface of the pressurizing portion. The air guiding portion defines an air channel communicating with the air outlet of the pressurizing portion.

Figure 5:
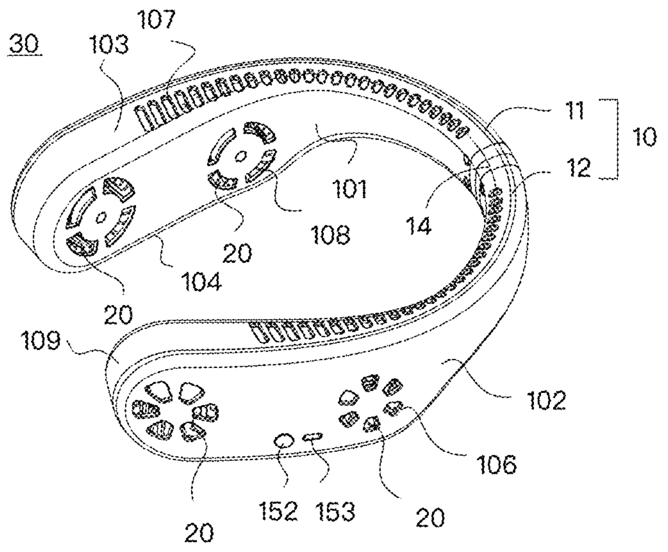
FIG. 5 is a schematic view of a neck fan in according to a first embodiment of the present disclosure.
Figure 6:
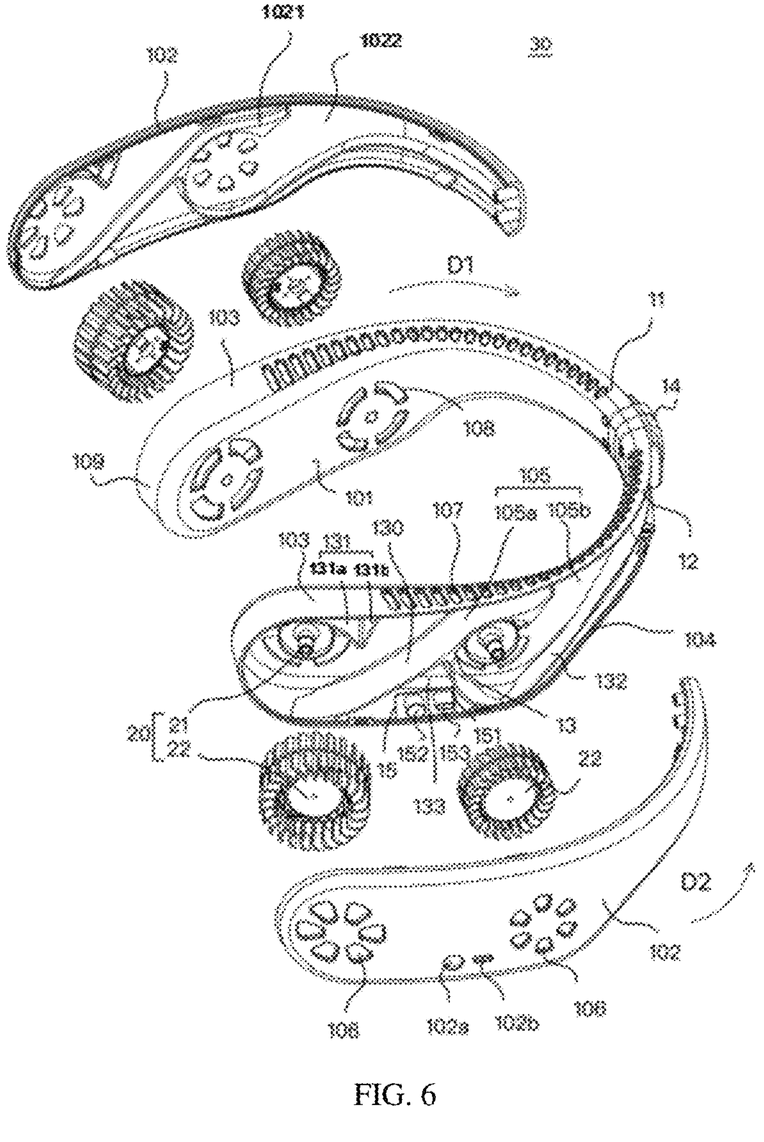
FIG. 6 is an exploded view of the neck fan of FIG. 5.

In an embodiment, as shown in FIGS. 5 and 6, FIG. 5 is a schematic view of a neck fan according to an embodiment of the present disclosure, and FIG. 6 is an explosive view of the neck fan of FIG. 5. The neck fan 30 includes an arc-shaped shell 10 and at least four fan assemblies 20. The at least four fan assemblies 20 may be arranged inside the arc-shaped shell 10. It shall be understood that, for illustration purposes only, in the following embodiment, the neck fan 30 including the at least four fan assemblies 20 will be taken as an example for illustration.

The arc-shaped shell 10 may be worn to surround the neck of the user. The arc-shaped shell 10 includes a first portion 11 and a second portion 12. The first portion 11 and the second portion 12 are arranged around two sides of the neck, such as a left side and a right side. Each of the first portion 11 and the second portion 12 includes an inner wall 101 configured to be close to the neck, an outer wall 102 opposite to the inner wall 101, a top wall 103 close to a head of the user and connecting between the inner wall 101 and the outer wall 102, and a bottom wall 104 opposite to the top wall 103 and connecting between the inner wall 101 and the outer wall 102.

The inner wall 101, the outer wall 102, the top wall 103, and the bottom wall 104 cooperatively define a receiving space 105. Each of the first portion 11 and the second portion 102 defines air inlets 106 and air outlets 107 communicating with the receiving space 105. In detail, in the present embodiment, the inner wall 101, the bottom wall 104, and the top wall 103 may be connected into an integrated structure (such as, a one-piece structure) to serve as a first side wall. The outer wall 102 may serve as a second side wall opposite to the first side wall. The first side wall and the second side wall cooperatively define the receiving space 105.

At least one partition 13 is received inside the receiving space 105 to divide the receiving space 105 into at least two receiving sub-spaces 105*a* and 150*b*. The at least two receiving sub-spaces 105*a* and 150*b* are arranged successively along an extension direction of the arc-shaped shell 10. Each of the at least two receiving sub-spaces correspond to and communicate with some of the air inlets 106 and some of the air outlets 107. Each of the fan assemblies is received in one corresponding receiving sub-space. Each of the fan assemblies is configured to guide the air, which flows into the corresponding receiving sub-space through corresponding air inlets 106, to flow to air outlets 107 corresponding to the receiving sub-space, allowing the air to be blown out through the corresponding air outlets 107. The number of the air outlets 107 may be more than one. The more than one air outlets may be distributed along the extension direction of the arc-shaped shell 10. Sizes, shapes of the air outlets 107 and/or distances between every two adjacent air outlets 107 vary gradually along the extension direction of the arc-shaped shell 10.

Compared to the neck fan in the art, in the neck fan 30 illustrated in the above-mentioned embodiments, the arc-shaped shell 10 includes the first portion 11 and the second portion 12. The first portion 11 and the second portion 12 are configured to be around two opposite sides of the neck. Each of the first portion 11 and the second portion 12 defines the receiving space 105, the air inlets 106, and the air outlets 107. The air inlets 106 and the air outlets 107 communicate with the receiving space 105. Each receiving space 105 is divided into at least two receiving sub-spaces by the partition 13. Each of the fan assemblies 20 is arranged in one of the receiving sub-spaces and configured to guide the air at the air inlets 106 to flow to the air outlets 107 to be blown out. Since the fan assemblies 20 are received in the receiving space 105, foreign matters, such as hair, may not be absorbed into the fan assemblies easily, allowing the neck fan to be used safely and conveniently. In the present embodiment, four receiving sub-spaces 105*a* and 105*b* are defined along the extension direction of the arc-shaped shell 10, and four fan assemblies 20 may be arranged and received in four receiving sub-spaces respectively. Since a plurality of the receiving sub-spaces 105*a* and 105*b* are defined, a length of the air duct in each of the receiving sub-spaces may be relatively short. When the air is flowing in each of the receiving sub-spaces, a concentration of the air being output may be reduced, the user may be comfortable about the air output, wind noise may be reduced, and an air volume loss may be reduced. The applicant of the present disclosure finds that, the longer the air duct, the longer period of time that the air flows along the receiving sub-space, increasing the wind noise and the air volume loss. By dividing the receiving space 105 into the plurality of receiving sub-spaces 105*a* and 105*b*, the wind noise and the air volume loss may be reduced significantly. In addition, by determining an extension direction, sizes, shapes of the air outlets 107 and distances between two adjacent air outlets 107, the user may be more comfortable about the air output from the neck fan 30, the air may be output from the neck fan 30 more softly, improving the user's experiences.

Further, each fan assembly 20 includes a driving shaft 21 and a fan blade assembly 22 mounted on the driving shaft 21. The driving shaft 21 extends from the inner wall 101 towards the outer wall 102. In this way, a thickness of the arc-shaped shell 10 along a direction from the inner wall 101 to the outer wall 102 may be reduced, such that the user may be comfortable when wearing the neck fan.

Further, the air inlets 106 are defined in the outer wall 102, and the air outlets 107 are defined in the top wall 103. It shall be understood that, the air inlets 106 are defined in the outer wall 102, and the outer wall 102 faces outwardly (i.e., opposite to the neck of the user), and therefore, the air may enter the shell easily and smoothly. In addition, the air outlets 107 are defined in the top wall 103, and the driving shaft 21 extends from the inner wall 101 to the outer wall 102. In this way, the fan blade assemblies 20 may direct the air from the air inlets 106 to the air outlets 107 to achieve a high air guiding efficiency. Moreover, the air outlets 107 are defined in the top wall 103, such that the air may be output towards a face and the head of the user, such that the user may be cooled rapidly.

Further, an end of the driving shaft 21 is fixedly arranged on the inner wall 101. It shall be understood that, such arrangement together with the air inlets 106 defined in the outer wall 102 allows the air inlets 106 to be unblocked, achieving a better air inlet effect.

Further, each fan assembly 20 corresponds to a plurality of air inlets 106. It shall be understood that, air is guided into the fan assembly 20 through the plurality of fan inlets 106, allowing the neck fan to have a better appearance, preventing foreign matters from entering the fan assembly 20 easily, increasing usage safety.

Further, the number of the air inlets 106 corresponding to each fan assembly 20 may be the same. The air inlets 106 corresponding to each fan assembly 20 are distributed in a circular shape. It shall be understood that, such arrangement allows the neck fan to have a better appearance, and prevents foreign matters from entering the fan assembly 20 easily. A better air inlet effect may be achieved due to such arrangement and shapes of the fan assemblies 20.

Further, a plurality of air inlets 108 are defined in the inner wall 101 corresponding to each fan assembly 20. The fan assembly 20 can guide the air from the air inlets 108 to the air outlets 107. Each of the plurality of air inlets 108 is arc shaped. The plurality of air inlets 108 corresponding to each fan assembly 20 are distributed in a circular shape. It shall be understood that, such arrangement allows the neck fan to have a better appearance, and prevents foreign matters from entering the fan assembly 20 easily. A better air inlet effect may be achieved due to such arrangement and shapes of the fan assemblies 20.

Further, the fan blade assembly 22 is a turbine fan blade assembly. It shall be understood that the turbine fan blade assembly may reduce the wind noise and improves the usage safety.

Further, the neck fan 30 further includes a connecting portion 14 connected between the first portion 11 and the second portion 12. The connecting portion 14 is configured to join the first portion 11 and the second portion 12 into an integrated structure. In the present embodiment, the connecting portion 14 may be configured as an individual element. In some embodiments, the connecting portion 14 may be integrally formed with one of the first portion 11 and the second portion 12, and then assembled with the other of the first portion 11 and the second portion 12. A structure of the connecting portion 14 may be various, and shall not be limited by the present disclosure.

The first portion 11 further includes an end plate 109 disposed at an end of the first portion 11 away from the connecting portion 14. The second portion 12 further includes an end plate 109 disposed at an end of the second portion 12 away from the connecting portion 14. Each end plate 109 is connected to the top wall 103, the bottom wall 104, the inner wall 101 and the outer wall 102. Sizes of the air inlets 106 corresponding to the fan assembly 20 arranged near the connecting portion 14 are less than those of the air inlets 106 corresponding to the fan assembly 20 arranged near the end plate 109. An outer diameter of the fan assembly 20 arranged near the connecting portion 14 is less that that of the fan assembly 20 arranged near the end plate 109. In other words, an end of the first portion 11 at which the end plate 109 is disposed may serve as a free end, and an end of the second portion 12 at which the end plate 109 is disposed may serve as another free end. An end of the first portion 11 near the connecting portion 14 may serve as a connecting end, and an end of the second portion 12 near the connecting portion 14 may serve as another connecting end. In the present embodiment, the sizes of the air inlets 106 corresponding to the fan assembly 20 arranged near the connecting end are less than those of the air inlets 106 corresponding to the fan assembly 20 arranged near the free end. The outer diameter of the fan assembly 20 arranged near the connecting end is less than that of the fan assembly 20 arranged near the free end. It shall be understood that, by determining various sizes of the air inlets 106 and various outer diameters of the fan blade assemblies 20, a size of the arc-shaped shell 10 may be gradually reduced along a direction from the end plate 109 to the connecting portion 14, such that the shell 10 is more suitable to a curve of the neck, allowing the user to be comfortable. In the present embodiment, the end plate 109 may be arc shaped, providing a better appearance. The shape of the end plate 109 may further be suitable to shapes of the receiving sub-spaces 105*a* and shapes of the fan assemblies 20 to achieve a better air inlet and outlet effect.

It shall be understood that, for each of the first portion 11 or the second portion 12, the inner wall 101, the top wall 103, the bottom wall 104, the end plate 109, and the partition 13 may be formed as a one-piece structure. The outer wall 102 may be buckled with the top wall 103, the bottom wall 104, and the end plate 109 through a buckle. There may be various types of buckles and various means to connect the above structure integrally, which will not be limited by the present disclosure.

Further, the number of the air outlets 107 may be more than one. The more than one air outlets 107 are distributed along the extension direction of the arc-shaped shell 10 and extends to a position near the connecting portion 14. Sizes of the more than one air outlets 107 gradually decrease along a direction from the end plate 109 to the connecting portion 14. It shall be understood that, the more than one air outlets 107 may improve the usage safety. Sizes of the more than one air outlets 107 gradually decrease along the direction from the end plate 109 to the connecting portion 14, allowing the air to be output in a more concentrated manner, improving air outlet intensity. In addition, sizes of the receiving sub-spaces 105*a* and 105*b* gradually decrease along the extension direction of the air duct. Therefore, the air output from the overall neck fan may be more uniform, and the user may feel comfortable. In detail, the extension direction of the arc-shaped shell 10 includes a first extension direction and a second extension direction. A direction extending from the first portion 11 to the second portion 12 may be referred to as a first extension direction D1. The sizes of the more than one air outlets 107 defined in the first portion 11 are gradually reduced along the first extension direction D1. A direction extending from the second portion 12 to the first portion 11 is referred to as a second extension direction D2. The sizes of the more than one air outlets 107 defined in the second portion 12 are gradually reduced along the second extension direction D2. Furthermore, each of the air outlets 107 is a strip-shaped air outlet. An extension direction of the strip-shaped air outlet may be inclined in a preset angle relative to the extension direction of the arc-shaped shell 10. The preset angle may be 90 degrees. It shall be understood that, by defining the air outlets 107 in the above extension direction, the air outlet of the neck fan 30 may be softer, and the user may be more comfortable, improving the user's experience. In particular, when the preset angle is 90 degrees, the air outlet efficiency of the air outlets 107 is improved. In addition, a cross-sectional area of the air duct of the first portion is gradually decreased along a direction from the first portion to the second portion; and/or a cross-sectional area of the air duct of the second portion is gradually decreased along a direction from the second portion to the first portion.

Further, the partition 13 is connected to a surface of the inner wall 101 facing the outer wall 102 and extends towards the outer wall 102. The partition 13 includes a partition body 130, a first guiding portion 131, and a second guiding portion 132. One end of the partition body 130 is connected to an end of the bottom wall 104 near the end plate 109. The other end of the partition body 130 extends towards a middle of the top wall 103 to be close to a middle of the top wall 103. The first guiding portion 131 includes a first sub-portion 131*a* and a second sub-portion 131*b*. The first sub-portion 131*a* surrounds a periphery of the fan assembly 20 arranged near the end plate 109. The second portion 131*b* is connected between the first portion 131*a* and the top wall 103. The second guiding portion 132 is connected to the partition body 130 and surrounds a periphery of the fan assembly 20 near the connecting portion 14. It shall be understood that, the partition body 130 is configured to divide the receiving space 105 into the two receiving sub-spaces 105*a* and 105*b*. The first guiding portion 131 and the second guiding portion 132 are configured to match shapes of the fan blade assemblies 22 so as to guide the air and achieve a better air outlet effect.

In particular, to the extent understandable to those in the centrifugal fan technical field, as shown in FIG. 6, the first guiding portion 131 serves as the vortex tongue structure 27 shown in FIG. 4, the first sub-portion 131*a* serves as the pressurizing plate 271 shown in FIG. 4 and the second sub-portion 131*b* serves as the wind guiding plate 272 shown in FIG. 4.

Further, an end of the second guiding portion 132 away from the partition body 130 extends to reach the connecting portion 14. Along a direction from the end plate 109 to the connecting portion 14, a distance between the second guiding portion 132 and the bottom wall 103 is gradually reduced until the second guiding portion 132 is tangent to the bottom wall 103, and then the distance between the second guiding portion 132 and the bottom wall 103 is gradually increased to a predetermined value and remains at the predetermined value. The predetermined value may be determined according to actual demands, for example, in some embodiments, the predetermined value may be a half of a distance between the top wall 103 and the bottom wall 104. Such arrangement of the second guiding portion 132 allows the air duct to extend to reach the connecting portion 14. In addition, some of the air outlets 107 are defined near the connecting portion 14. In this way, a range of the air output from the neck fan 30 is larger, improving the cooling effect.

Further, the neck fan 30 further includes an electronic control assembly 15. The electronic control assembly 15 includes a battery and a printed circuit board 151. The second guiding portion 132 and the partition body 130 cooperatively define a receiving chamber 133 to receive at least part of the electronic control assembly 15. It shall be understood, the electronic control assembly 15 are received in the receiving chamber 133, preventing heat generated by the electronic control assembly 15 from entering the receiving sub-spaces 105*a* and 150*b*, and therefore, the cooling effect may not be affected. In addition, such arrangement allows individual arrangement of heat dissipation and wiring of the electronic control assembly 15, thereby improving the usage safety.

Further, the electronic control assembly 15 further includes a switch button 152 and a data port 153. The outer wall 102 of the second portion 12 defines a first opening 102*a* corresponding to the switch button 152 and a second opening 102*b* corresponding to the data port 153. The switch button 152 is mounted corresponding to the first opening 102*a* and connected to the printed circuit board 151. The data port 153 is mounted corresponding to the second opening 102*b* and connected to the printed circuit board 151. Such arrangement allows the user to operate the neck fan easily, improving user's experience. Furthermore, it shall be understood, in addition to the electronic control assembly 15, structures and elements of the first portion 11 and the second portion 12 are symmetrically arranged to increase wearing comfort.

Further, the outer wall 102 includes a main plate 1021 and an auxiliary plate 1022. A shape and a position of the auxiliary plate 1022 correspond to those of the partition 13. The auxiliary plate 1021 is connected between the main plate 1021 and the partition 13. It shall be understood that the auxiliary plate 1022 and the partition 13 cooperatively define the air duct of the fan assembly 20, so as to achieve a better air guiding effect.

Figure 7:
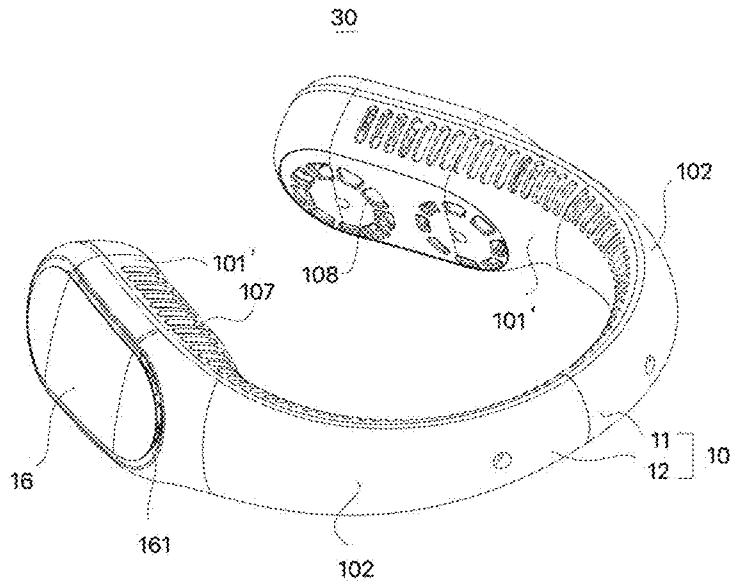
FIG. 7 is a schematic view of a neck fan in according to a second embodiment of the present disclosure.
Figure 8:
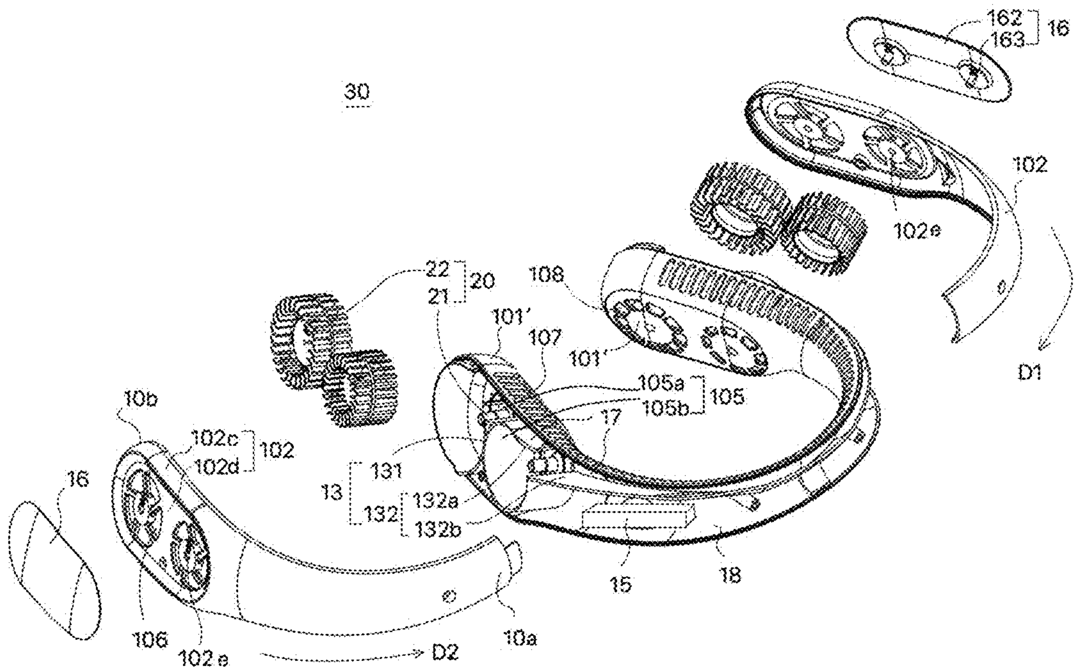
FIG. 8 is an exploded view of the neck fan of FIG. 7.
Figure 9:
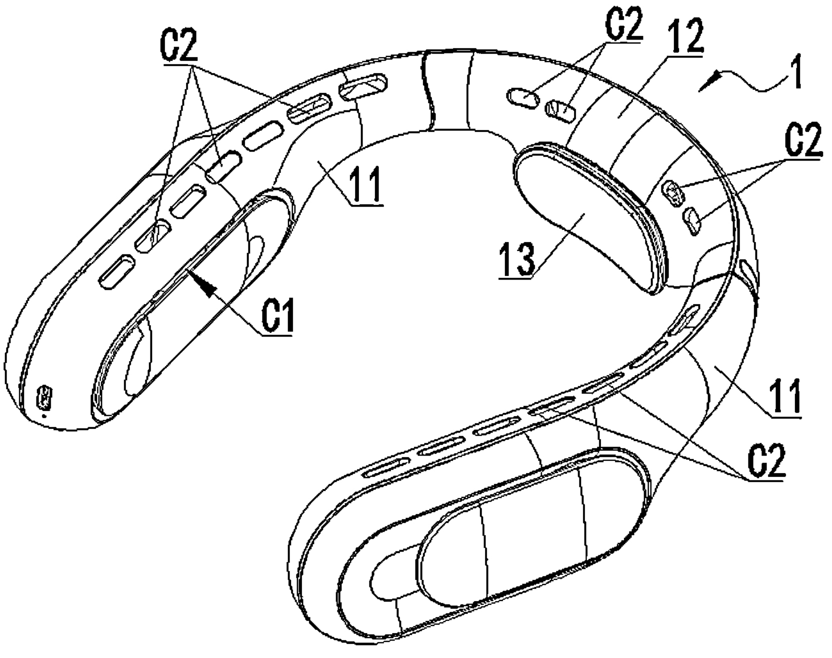
FIG. 9 is a schematic view of a neck fan according to an embodiment of the present disclosure.

In another embodiment, as shown in FIGS. 7 and 8, FIG. 7 is a schematic view of a neck fan 30 according to an embodiment of the present disclosure, and FIG. 8 is an explosive view of the neck fan 30 of FIG. 7. The neck fan 30 includes an arc-shaped shell 10 and at least four fan assemblies 20. The at least four fan assemblies 20 are arranged inside the arc-shaped shell 10. It shall be understood that, in the present embodiment, a neck fan having four fan assemblies 20 may be taken as an example for illustration.

The arc-shaped shell 10 may be hung around the neck of the user. The arc-shaped shell 10 includes a first portion 11 and a second portion 12. The first portion 11 and the second portion 12 are arranged around two sides of the neck, such as a left side and a right side. Each of the first portion 11 and the second portion 12 includes a side wall that defines a receiving space 105. Each of the first portion 11 and the second portion 12 defines air inlets 106 and air outlets 107 communicating with the receiving space 105.

At least one partition 13 is received in the receiving space 105 to divide the receiving space 105 into at least two receiving sub-spaces 105*a* and 150*b*. The at least two receiving sub-spaces 105*a* and 150*b* are arranged successively along an extension direction of the arc-shaped shell 10. Each of the at least two receiving sub-spaces correspond to and communicate with some of the air inlets 106 and some of the air outlets 107. Each of the fan assemblies 20 is received in one corresponding receiving sub-space. Each of the fan assemblies is configured to guide the air, which flows into the corresponding receiving sub-space through corresponding air inlets 106, to flow to air outlets 107 corresponding to the receiving sub-space, allowing the air to be blown out through the corresponding air outlets 107. The number of the air outlets 107 may be more than one. The more than one air outlets 107 may be distributed along the extension direction of the arc-shaped shell 10. Sizes, shapes of the air outlets 107 and/or distances between every two adjacent air outlets 107 vary gradually along the extension direction of the arc-shaped shell 10.

Compared to the neck fan in the art, in the neck fan 30 illustrated in the above-mentioned embodiments, the arc-shaped shell 10 includes the first portion 11 and the second portion 12. The first portion 11 and the second portion 12 are configured to be around two opposite sides of the neck. Each of the first portion 11 and the second portion 12 defines the receiving space 105, the air inlets 106, and the air outlets 107. The air inlets 106 and the air outlets 107 communicate with the receiving space 105. Each receiving space 105 is divided into at least two receiving sub-spaces 105*a* and 105*b* by the partition 13. Each of the fan assemblies 20 is arranged in one of the receiving sub-spaces and configured to guide the air at the air inlets 106 to flow to the air outlets 107 to be blown out. Since the fan assemblies 20 are received in the receiving space 105, foreign matters, such as hair, may not be absorbed into the fan assemblies easily, allowing the neck fan to be used safely and conveniently. In the present embodiment, four receiving sub-spaces 105*a* and 105*b* are defined along the extension direction of the arc-shaped shell 10, and four fan assemblies 20 may be arranged and received in four receiving sub-spaces respectively. Since a plurality of the receiving sub-spaces 105*a* and 105*b* are defined, a length of the air duct in each of the receiving sub-spaces may be relatively short. When the air is flowing in each of the receiving sub-spaces, a concentration of the air being output may be reduced, the user may be comfortable about the air output, wind noise may be reduced, and an air volume loss may be reduced. The applicant of the present disclosure finds that, the longer the air duct, the longer period of time that the air flows along the receiving sub-space, increasing the wind noise and the air volume loss. By dividing the receiving space 105 into the plurality of receiving sub-spaces 105*a* and 105*b*, the wind noise and the air volume loss may be reduced significantly.

In detail, the side wall includes a first side wall 101' configured to be close to the neck of the user and a second side wall 102 opposite to the first side wall 101'. The air inlets 106 are defined in the second side wall 102, and the air outlets 107 are defined in a region of the first side wall 101' adjacent to the second side wall 102 or defined in a region of the second side wall 102 adjacent to the first side wall 101'. In the present embodiment, the air outlets 107 are defined in the region of the first side wall 101' adjacent to the second side wall 102 and are close to the user's head and face.

Further, in detail, a direction extending from the first portion 11 to the second portion 12 may be referred to as a first extension direction D1. The sizes of the more than one air outlets 107 defined in the first portion 11 are gradually reduced along the first extension direction D1. A direction extending from the second portion 12 to the first portion 11 is referred to as a second extension direction D2. The sizes of the more than one air outlets 107 defined in the second portion 12 are gradually reduced along the second extension direction D2. Furthermore, each of the air outlets 107 is a strip-shaped air outlet. An extension direction of the strip-shaped air inlet may be inclined in a preset angle relative to the extension direction of the arc-shaped shell 10. The preset angle may be 90 degrees. It shall be understood that, by defining the air outlets 107 in the above extension direction, the air outlet of the neck fan 30 may be softer, and the user may be more comfortable, improving the user's experience. In particular, when the preset angle is 90 degrees, the air outlet efficiency of the air outlets 107 is improved. In some embodiments, the air outlets 107 may be at least one of petal-shaped and heart-shaped. It shall be understood that, both the petal-shaped air outlets 107 and the heart-shaped air outlets 107 may output the air uniformly and provides better appearance for the neck fan.

Further, each fan assembly 20 includes a driving shaft 21 and a fan blade assembly 22 mounted on the driving shaft 21. The driving shaft 21 extends from the first side wall 101' towards the second side wall 102. In this way, a thickness of the arc-shaped shell 10 along a direction from the first side wall 101' to the second side wall 102 may be reduced, such that the user may be comfortable when wearing the neck fan.

It shall be understood, the air inlets 106 are defined in the second side wall 102, and the second side wall 102 faces outwardly (i.e., away from the user's neck) allowing the air to flow into the air inlets 106 easily, allowing the air to flow in smoothly. Such arrangement together with the driving shaft 21 extending along the direction from the first side wall 101' to the second side wall 102 enables the fan blade assembly 22 to direct the air from the air inlets 106 to the air outlets 107, thereby achieving a relatively high air guiding efficiency. Moreover, the air outlets 107 are defined at the first side wall 101' close to the user's head and face, such that the air may be directed out towards the user's head and face, thereby achieving better cooling effect.

The first side wall 101' defines a plurality of air inlets 108 corresponding to each fan assembly 20. The fan assembly 20 can guide the air at the air inlets 108 to the air outlets 107. Each of the plurality of air inlets 108 is arc shaped. The plurality of air inlets 108 corresponding to each fan assembly are arranged in a circular shape. It shall be understood, such arrangement provides a better appearance of the neck fan 30, and prevents the foreign matters from entering the fan assembly 20. Such arrangement together with shapes of the fan assemblies 20 achieves a better air guiding effect.

In an embodiment, the first side wall defines the plurality of air inlets 108, and the second side wall defines the plurality of air inlets 106. The first side wall faces the neck of the user, and the second side wall is connected to the first side wall and faces away from the neck. Further, at least one of a region of the first side wall close to the second side wall and a region of the second side wall close to the first side wall defines the plurality of air outlets 107. In addition, the plurality of air outlets 107 are located between the plurality of air inlets 108 of the first side wall and the plurality of air inlets 106 of the second side wall along an extension direction of the driving shaft 21.

Further, the first portion 11 has a connecting end 10*a* connected to the second portion 12 and a free end 10*b* away from the connecting end 10*a*; and the second portion 12 also has a connecting end 10*a* connected to the first portion 11 and a free end 10*b* away from the connecting end 10*a*. Sizes of the air outlets 107 corresponding to the fan assembly 20 adjacent to the connecting end 10*a* are less than those of the air outlets 107 corresponding to the fan assembly 20 adjacent to the free end 10*b*. An outer diameter of the fan blade assembly 22 adjacent to the connecting end 10*a* is less than that of the fan blade assembly 22 adjacent to the free end 10*b*. It shall be understood, the sizes of the air inlets 106 and the diameter of the fan blade assembly 22 enables a size of the arc-shaped shell 10 to be reduced gradually along a direction from the free end 10*b* to the connecting end 10*a*, such that the shape of the neck fan may fit a curve of the neck more appropriately, increasing wearing comfort.

In the present embodiment, each of the first portion 11 and the second portion 12 includes a cover 16. The cover 16 is disposed on a side of the second side wall 102 away from the first side wall 101' and corresponds to (such as covers) the air inlets 106. A gap 161 communicated with the air inlets 106 is defined between an edge of the cover 16 and the second side wall 102 to allow air to flow into the air inlets 106.

Further, the second side wall 102 includes a main body 102*c* and defines a recess 102*d*. A wall of the recess 102*d* is connected to the main body 102*c*. In other words, the side of the second side wall 102 away from the first side wall 101' is recessed inwardly towards the first side wall 101' to define the recess 102*d*. The air inlets 106 are defined at the recess 102*d*, such as defined in the bottom wall of the recess 102*d*. The cover 16 covers the recess 102*d*. The cover 16 is partially connected to the main body 102*c* connected to wall of the recess 102*d* to define the gap 161. It shall be understood, the cover 16 covers the air inlets 106, and air enters through the gap 161 and the air inlets 106. In this way, a better appearance is provided, and the foreign matters may be prevented from entering the fan assembly 20, increasing the usage safety. Defining the recess 102*d* further reduces an overall size of the neck fan 30 and provides the appearance aesthetics.

Further, the cover 16 includes a cover body 162 and a first mounting portion 163 arranged at a side of the cover body 162 adjacent to the second side wall 102. A side of the second side wall 102 close to the cover 16 is arranged with a second mounting portion 102*e*. In detail, the second mounting portion 102*e* may be arranged on the wall of the recess 102*d* and is located between the plurality of air inlets 106.

Further, the cover 16 further includes the cover body 162 and the first mounting portion 163 arranged on the cover body 162. The second mounting portion 102*e* is arranged on the second side wall 102 and is engaged with the first mounting portion 163. Engagement between the second mounting portion 102*e* and the first mounting portion 163 enables the cover 16 to be mounted (such as detachably or movably mounted) on the side of the second side wall 102 away from the first side wall 101'. It shall be understood, engagement between the first mounting portion 163 and the second mounting portion 102*e* enables the cover 16 to be detachably or movably mounted onto the second side wall 102, allowing the neck fan to be used or disassembled easily.

Further, the first mounting portion 163 and the second mounting portion 102*e* may be engaged in a first mounting state or in a second mounting state. In the first mounting state, the gap 161 is defined between the edge of the cover 16 and the second side wall 102. In the second mounting state, the edge of the cover 16 abuts against the second side wall 102 so as to cover the air inlets 106. It shall be understood, the first mounting portion 163 and the second mounting portion 102*e* may be engaged in the first mounting state or in the second mounting state. Therefore, in the first mounting state, the air can enter the fan assembly through the gap 161 and the air inlets 106; and in the second mounting state, the gap 161 and the air inlets 106 are covered, and dust may be prevented from entering the arc-shaped shell through the air inlets 106 when the neck fan 30 is not in use, achieving the dustproof effect.

It shall be understood, the first mounting state and the second mounting state may be switched from one to the other. In some embodiments, elastic fasteners may be configured, serving as the first mounting portion and the second mounting portion. In this way, the first mounting state and the second mounting state may be switched by pressing the cover 16 along a direction facing the second side wall 102. For example, a first press is made to switch from the first mounting state to the second mounting state, and a next press is made to switch from the second mounting state to the first mounting state. There are various structures for implementing the above-mentioned press switch control, which will not be described specifically hereinafter.

In the present embodiment, the first mounting portion 163 may be a mounting shaft connected to the cover body 162, and the second mounting portion 102*e* may be a mounting hole corresponding to the mounting shaft. In other embodiments, the first mounting portion 163 may be a mounting hole defined in the cover body 162, and the second mounting portion 102*e* may be a mounting shaft corresponding to the mounting hole. It shall be understood, the mounting shaft may be received in the mounting hole to engage the cover 16 to the second side wall 102, achieving an easy mounting operation.

In the present embodiment, the partition 13 includes a partition body 131 and a guiding portion 132. A shape of the partition body 131 at least partially fits to a shape of the fan assembly 20, and the partition body 131 surrounds a periphery of the fan assembly 20. The guiding portion 132 is connected to the partition body 131. The guiding portion 132 and the side wall cooperatively define the air duct communicated to the air outlets 107. It shall be understood that by adapting the partition part 131 to the shape of the fan assembly 20 and by configuring the guiding portion 132 and the side wall to cooperatively define the air duct 17 communicated to the air outlets 107, a better air guiding effect may be achieved, and an air inlet and outlet efficiency may be improved.

Further, for each of the first portion 11 and the second portion 12, the guiding portion 132 includes a first guiding sub-portion 132*a* located between two fan assemblies 20 and a second guiding sub-portion 132*b* arranged at a side of one of the two fan assemblies 20 away from the other of the two fan assemblies. The second guiding sub-part 132*b* extends from one of the first portion 11 and the second portion 12 to the other of the first portion 11 and the second portion 12. A side of the second guiding sub-portion 132*b* and the side wall cooperatively define an accommodating space 18. The neck fan 30 further includes an electronic control assembly 15. The electronic control assembly 15 includes a battery and a printed circuit board. The accommodating space 18 is defined to receive at least one of the battery and the printed circuit board. It shall be understood, by receiving the electronic control assembly 15 in the accommodating space 18, configuration of the neck fan 30 may be effectively balanced, providing wearing comfort for the user. In addition, the fan blade assembly 20 may be a turbine fan blade assembly. It shall be understood that the turbine fan blade assembly may achieve lower noise and higher safety.

In an embodiment, as shown in FIG. 4, the present disclosure provides a turbine blade assembly 22 for a neck fan. The turbine blade assembly 22 has a first side and a second side opposite to the first side. The turbine blade assembly 22 includes a first side blade disposed at the first side, a second side blade disposed at the second side, and a separation plate disposed between the first side and the second side. The first side defines a first inlet window, and the second side defines a second inlet window. The first inlet window and the second inlet window are defined to allow air to flow in from an outside of the neck fan. A bottom wall of the first inlet window is recessed from a plane where the first side blade is disposed. A bottom wall of the second inlet window is recessed from a plane where the second side blade is disposed.

Figure 10:
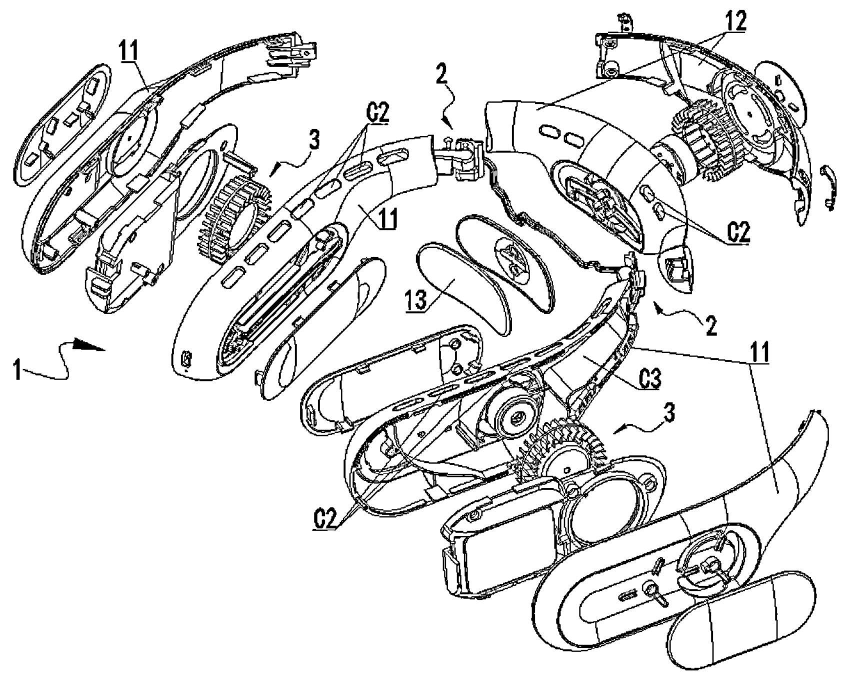
FIG. 10 is an exploded view of the embodiment shown in FIG. 9.
Figure 11:
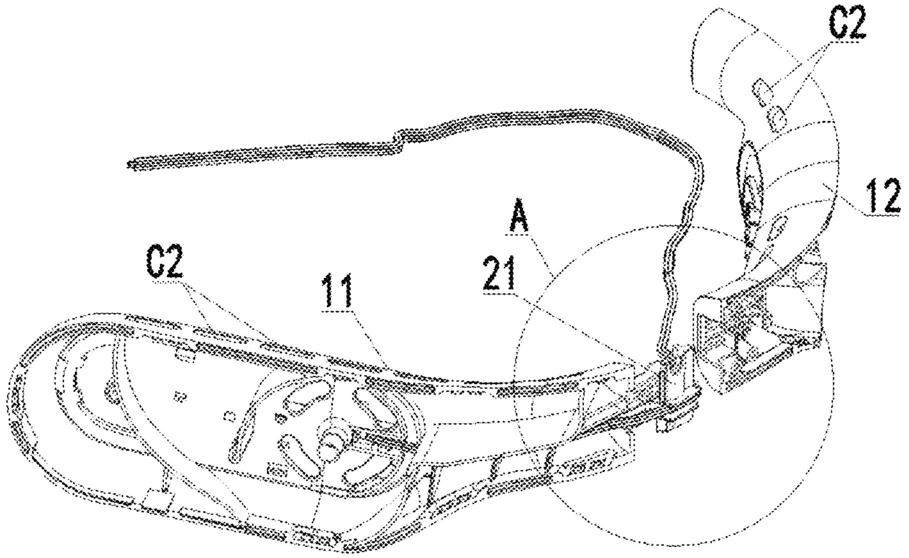
FIG. 11 is a schematic view showing connection among an air guiding portion, a neck wearing portion and an adjustment member of a neck fan according to the embodiment of the present disclosure.

As shown in FIGS. 10-11, FIG. 10 is a perspective view of a neck fan according to another embodiment of the present disclosure, and FIG. 11 is a perspective view of the neck fan shown in FIG. 10 from another view angle. The neck fan 1 includes a curved shell 10 and a fan assembly 20. The neck fan 1 can be worn around the neck.

Figure 12:
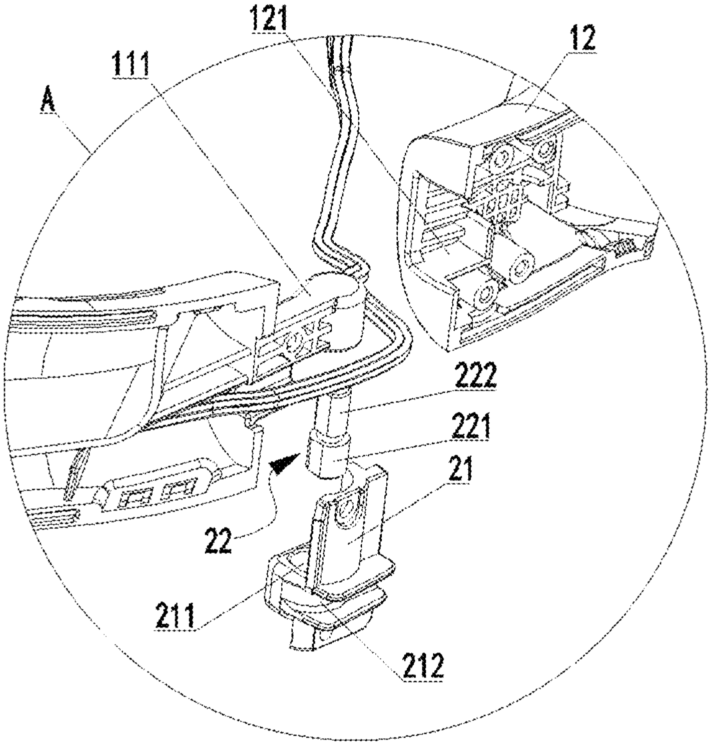
FIG. 12 is an enlarged view of a portion A shown in FIG. 11.
Figure 13:
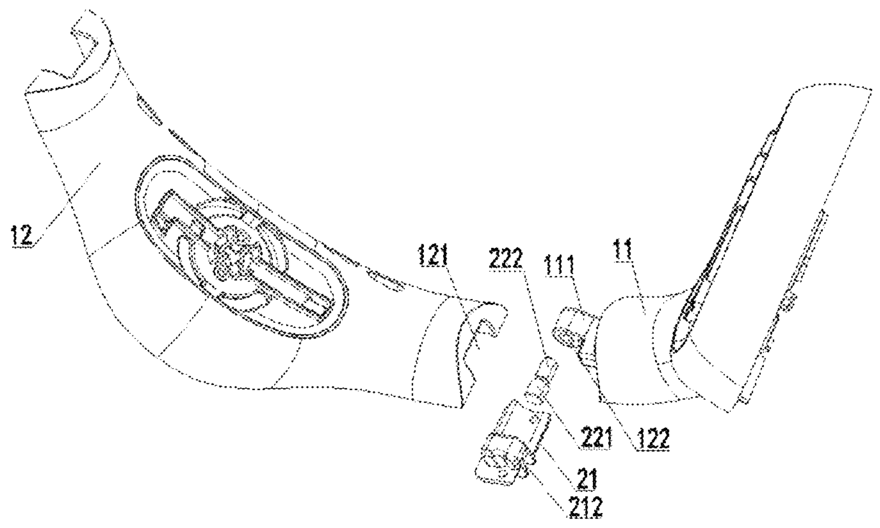
FIG. 13 is a schematic view showing connection among an air guiding portion, a neck wearing portion, a limitation member, and a rotation shaft of a neck fan according to the embodiment of the present disclosure.
Figure 14:
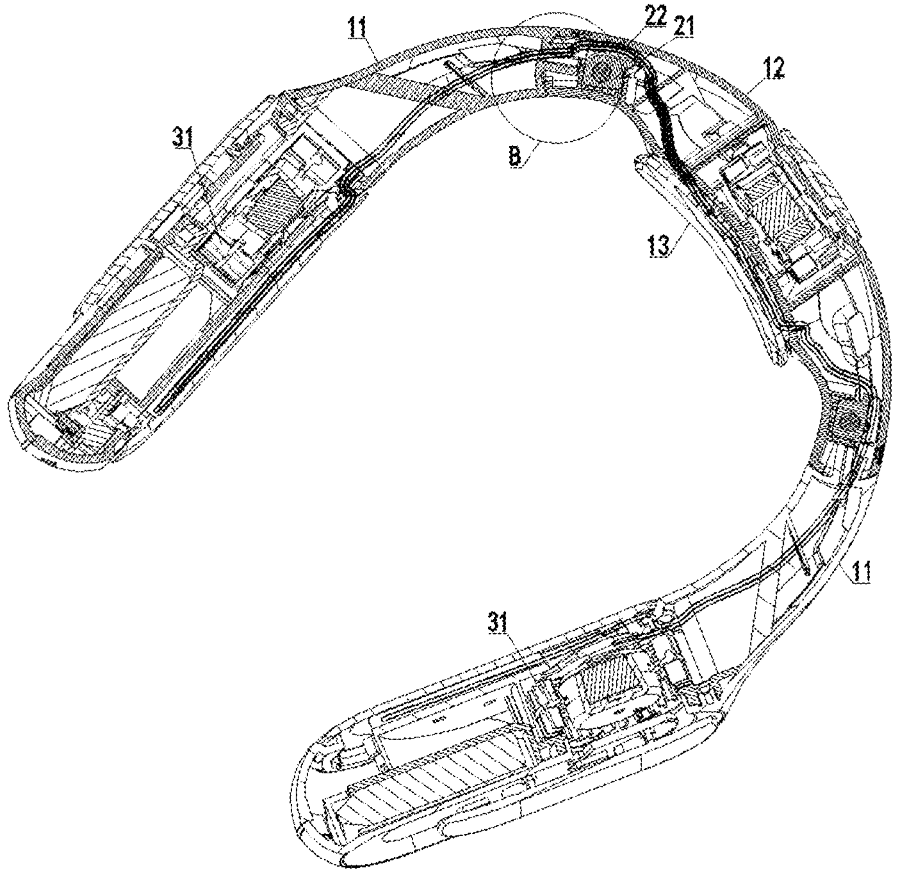
FIG. 14 is a cross section view of a neck fan according to the embodiment of the present disclosure.

As shown in FIGS. 12-14, FIG. 12 is an exploded view of the neck fan shown in FIG. 10, FIG. 13 is a perspective view of a portion of the neck fan shown in FIG. 10, and FIG. 14 is a cross sectional view of the neck fan shown in FIG. 10. The shell 10 includes a first shell 11 and a second shell 12. The first shell 11 and the second shell 12 are opposite to each other, and are disposed on opposite sides of the neck when the neck fan 1 is worn on the user. At least one of the first shell 11 and the second shell 12 includes a first part 111, a second part 112 and a third part 113. The third part 113 is connected between the first part 111 the second part 111. The first part 111 defines a first storage cavity 111*a* and a first air outlet 111*b* communicating with the first storage cavity 111*a*. The second part 112 defines a second storage cavity 112*a* and a second air outlet 112*b* communicating with the second storage cavity 112*a*. The third part 113 defines a third storage cavity 113*a* between the first storage cavity 111*a* and the second storage cavity 112*a*, and the third storage cavity 113*a* is communicating with the first storage cavity 111*a* and the second storage cavity 112*a*. At least one of the first shell 11 and the second shell 12 defines an air inlet 114 communicating with at least one of the first storage cavity 111*a*, the second storage cavity 112*a* and the third storage cavity 113*a*. The fan assembly 20 is at least partially received in the third storage cavity 113*a* and is configured to guide the air from the air inlet 114 to the first air outlet 111*b* and the second air outlet 112*b*.

As shown in FIG. 9, FIG. 10, FIG. 11 and FIG. 12, the neck fan includes a shell 1, an adjustment assembly 2 and a fan assembly 3. The shell 1 is configured to hang around the user's neck. The shell 1 defines an air inlet C1, an air outlet C2 and an air duct C3, and the air inlet C1, the air outlet C2 and the air duct C3 communicate with each other. The adjustment assembly 2 is arranged on the shell 1 to adjust a bending angle of the shell 1. The fan assembly 3 is received inside the shell 1 and is configured to guide the air entering from the air inlet C1 to flow along the air duct C3 to reach the air outlet C2, such that the air further flows to an outside of the neck fan through the air outlet C2. The adjustment assembly 2 is configured to adjust the bending angle of the shell 1, such that the shell 1 can matched with various neck sizes of various users. In this way, the neck fan can be portable and highly adaptable, allowing various users to have better usage experience.

In an embodiment, the shell includes a first shell, a second shell and a third shell. The third shell is connected between the first shell and the second shell. Each of two opposite ends of the third shell is configured with one adjustment assembly. An end of the third shell is connected to the first shell through a corresponding adjustment assembly, and the other end of the third shell is connected to the second shell through another corresponding adjustment assembly. Each of the first shell and the second shell is rotatable relative to the third shell through shell adjustment assembly.

In an embodiment, each of the first shell and the second shell may serve as an air guide portion 11. The third shell may serve as a neck wearing portion 12. That is, in the present embodiment, the shell 1 includes the air guide portion 11 and the neck wearing portion 12. The air guide portion 11 is disposed at each of two free ends of the neck wearing portion 12. The air guide portion 11 is connected to the neck wearing portion 12 through the adjustment assembly 2. The adjustment assembly 2 may be configured with the air guide portion 11 to connect to the neck wearing portion 12. Alternatively, the adjustment assembly 2 may be configured with the neck wearing portion 12 to connect to the air guide portion 11. The air duct C3 extends from the fan assembly 3 towards the neck wearing portion 12.

In another embodiment, the adjustment assembly 2 includes a position limitation member 21 and a shaft structure 22. The shaft structure 22 can rotate and hover by itself. The shaft structure 22 includes a first shaft portion 221 and a second shaft portion 222. The first shaft portion 221 and the second shaft portion 222 can rotate relative to each other. The position limitation member 21 is disposed at an end portion of the neck wearing portion 12. The position limitation member 21 is connected to the first shaft portion 221. The second shaft portion 222 is connected to the air guide portion 11. The shaft structure 22 and the position limitation member 21 are configured to enable the shaft structure 22 to connect to both the air guide portion 11 and the neck wearing portion 12. In this way, so that the air guide portion 11 and the neck wearing portion 12 can rotate relative to each other. While the user is wearing the fan, the air guide portion 11 and the neck wearing portion 12 may be rotated to reach a position suitable for the wearer's neck. The shaft structure 22 can hover by its own, and therefore, rotation can be stopped when the suitable position is reached, preventing the shaft structure 22 from further rotating while the user is wearing the fan. In this way, while the user is wearing the fan, the fan can stably attach to the user's neck.

It shall be understood that, while the user is wearing the fan, an opening angle of the neck fan is selectable. The opening angle can be adjusted to blow the air to various regions of the head. In this way, the shaft structure allows the user to rotate the shells to blow the air to desired places on purpose.

In another embodiment, the shaft structure 22 is received inside the neck wearing portion 12, and an outer periphery of the shaft structure 22 is not provided with any damping element. In this way, the shaft structure 22 can be well protected from erosion caused by external water or dust. It shall be understood that the shaft structure 22 is received inside the neck wearing portion 12. Compared to the shaft structure 22, the end portion of the neck wearing portion 12 is closer to the air guide portion 11. The shaft structure 22 is located at a position having a certain distance from the end portion of the neck wearing portion 12. The neck wearing portion 12 includes an upper shell and a lower shell. The shaft structure 22 is arranged on the lower shell of the neck wearing portion 12, and specifically, the shaft structure 22 is disposed on a side near the upper shell. The end portion of the neck wearing portion 12 wraps around the shaft structure 22. In this way, the shaft structure 22 is wrapped and hidden, enhancing aesthetic appearance and integrity of the neck fan, and allowing an internal space of the neck section 12 to used optimally.

The damping element may include an elastic pad, a silicone pad, a metal pad, and so on. Generally, the pad may be worn out and become smooth after being used for a long time, resulting in a lower friction, which in turn affects the hovering effect.

In another embodiment, as shown in FIG. 13, the position limitation member 21 defines a first recess 211 for receiving the first shaft portion 221. An end of the air guide portion 11 near the neck wearing portion 12 defines a second recess 122 for receiving the second shaft portion 222. A size of the first shaft portion 221 is larger than a size of the first recess 211. A size of the second shaft portion 222 is larger than a size of the second recess. The “size” may refer to a diameter in the present embodiment. In this way, an interference fit is achieved between the shaft structure 22 and the first recess 211, and between the shaft structure 22 and the second recess 122. In addition, such configuration may extend a service life of the shaft structure. After the shaft structure 22 is rotated for a large number of times and is used for a long time, the shaft structure 22 may not be worn out, a relatively high friction may be maintained, ensuring the hovering effect, and a slipping phenomenon may be avoided.

The above-mentioned configuration allows the shaft structure 22 to be wrapped by a wall of the first recess 211 and a wall of the second recess 122. On one hand, rotation of the shaft structure 22 may not be affected, and on the other hand, the shaft structure may be well protected, extending the service life of the shaft structure 22.

In another embodiment, a surface of the shaft structure has knurling. In detail, an outer surface of the shaft structure is arranged with the knurling. The knurling allows the shaft structure 22 to be in the interference fit with the first recess 211 and the second recess. A contact area between the shaft structure and the wall of the first recess 211 and a contact area between the shaft structure and the wall of the second recess are increased, ensuring the frictional force to be sufficient for the hovering effect, and the service life of the neck fan, which can adjust the bending angle, may be increased.

In another embodiment, the position limitation member 21 defines a wire slot 212 for receiving and collecting wires. The wire slot 212 allows the wires to be gathered well, preventing the wires from occupying too much space of the neck fan, facilitating subsequent maintenance of the neck fan, and facilitating replacement of components of the neck fan.

In another embodiment, the position limitation member 21 is an independent structure. Alternatively, the position limitation member 21 may be integrally formed with the air guide portion 11. Alternatively, the position limitation member 21 may be integrally formed with the neck wearing portion 12.

In another embodiment, one of the air guide portion 11 and neck wearing portion 12 is configured with a plurality curved bumps, and the other one of the air guide portion 11 and neck wearing portion 12 defines a plurality of curved grooves. The curved bumps may be adapted to and engaged with the curved grooves. The bending angle of the shell 1 may be adjusted by engaging the curved bumps with the curved grooves at various positions. In this way, the neck fan may be adapted to various neck sizes of various users.

In another embodiment, the adjustment assembly 2 includes a plurality of protrusions and a plurality of recesses. The plurality of protrusions are arranged on one of the air guide portion 11 and the neck wearing portion 12, and the plurality of recesses are defined in the other one of the air guide portion 11 and the neck wearing portion 12. The bending angle of the shell 1 may be adjusted by engaging the protrusions with the recesses at various positions. In this way, the neck fan may be adapted to various neck sizes of various users.

In another embodiment, the adjustment assembly 2 includes a slide block and a slide rail. The slide block is arranged one of the air guide portion 11 and the neck wearing portion 12, and the slide rail is arranged on the other one of the air guide portion 11 and the neck wearing portion 12. The slide block is slidable on the slide rail. The bending angle of the shell 1 may be adjusted by sliding the slide block to reach various positions on the slide rail. In this way, the neck fan may be adapted to various neck sizes of various users.

In another embodiment, an inner side (a side near the user’s neck) of the neck wearing portion 12 is arranged with an attachment portion 13. The attachment portion 13 is configured to attach to the user’s neck, allowing the user to feel more comfortable while wearing the fan. The attachment portion 13 may be curved inwardly. The attachment portion 13 may be made of soft material, allowing the attachment portion to attach to the user’s neck more easily, protecting the user’s skin from being rubbed.

In another embodiment, the fan assembly 3 includes a fan 31 and a motor driving the fan to rotate.

Figure 15:
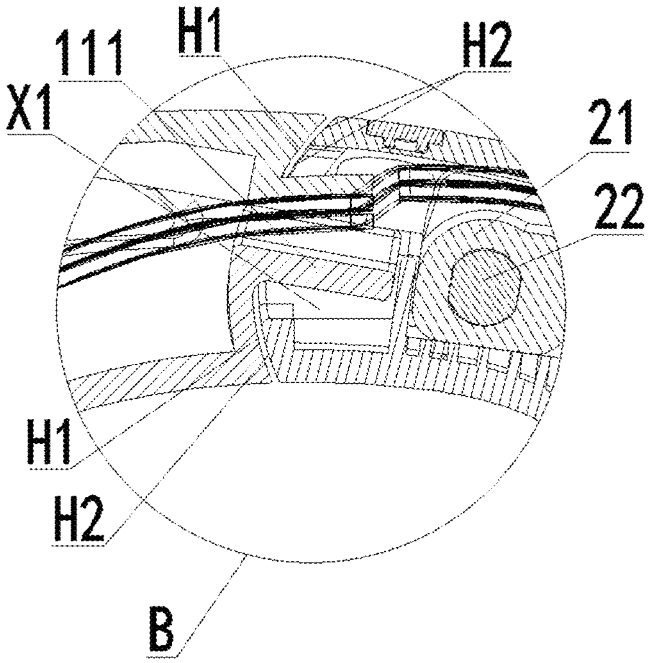
FIG. 15 is an enlarged view of a portion B shown in FIG. 13.
Figure 16:
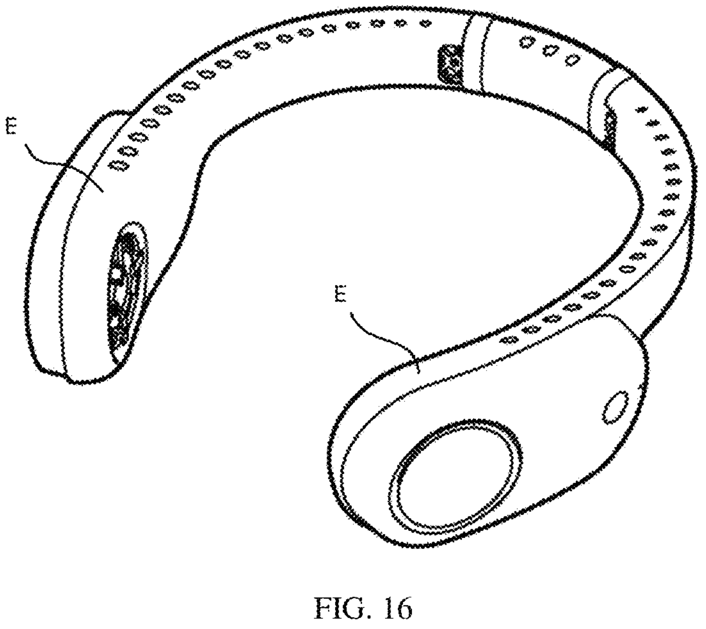
FIG. 16 is a schematic view of a neck fan in the art.

As shown in FIG. 14 and FIG. 15, the position limitation member 21 the first recess 211 for receiving the first shaft portion 221. An insertion portion is extended from the end of the air guide portion 11. The insertion portion 111 defines the second recess 122 for receiving the second shaft portion 222. The end of the neck wearing portion 12 defines a receiving recess 121 for receiving the insertion portion 111 of the end of the air guide portion 11. In this way, the air guide portion 11 and the neck wearing portion 12 are connected. In addition, stability of the connection between the air guide portion 11 and the neck wearing portion 12 may be improved.

The insertion portion 111 may be rod shaped, and an end of the insertion portion 111 may be cylindrical. An end surface of the end of the insertion portion 111 may be recessed along a central axis of the cylindrical end to define the second recess 122.

In another embodiment, an edge of the air guide portion near the insertion portion 111 may be a recessed-curved portion H1. An edge of a wall of the receiving recess 121 near the neck wearing portion 12 may be a protruded-curved portion H2. The recessed-curved portion H1 may fit with the protruded-curved portion H2. In this way, while the insertion portion 111 is inserted into the receiving recess 121, an edge of the air guide portion 11 and an edge of the neck wearing portion 12 may be connected tightly, preventing the external water and dust from an inside of the neck fan through a gap between the air guide portion 11 and the neck wearing portion 12, such that the neck fan may be protected from erosion.

In another embodiment, when the insertion portion 111 is inserted into the receiving recess 121, a rotation gap X1 may be defined between the insertion portion 111 and the wall of the receiving recess 121. When the user is adjusting relative positions between the air guide portion 11 and the neck wearing portion 12, i.e., when the shaft structure 22 is rotating, the insertion portion 11 may be rotating in the receiving recess 121. Defining the rotation gap X1 provides a space margin for rotating the insertion portion 111 in the receiving recess 121, facilitating the user to adjust the neck fan based on the size of the user's neck.

According to the present disclosure, the neck fan includes the shell, the adjustment assembly and the fan assembly. The shell is configured to hang around the user's neck. The shell defines the air inlet, the air outlet, and the air duct, and the air inlet, the air outlet, and the air duct communicate with each other. The adjustment assembly is arranged on the shell and is configured to adjust the bending angle of the shell. The fan assembly is received inside the shell and is configured to guide the air from the air inlet to flow through the air duct to reach the air outlet, such that the air further flows to the outside through the air outlet. The neck fan is portable, and the bending angle of the neck fan is adjustable, such that the neck fan may be suitable for various neck sizes of various users.

FIGS. 16-22 show a neck fan according to another embodiment of the present disclosure.

Figure 17:
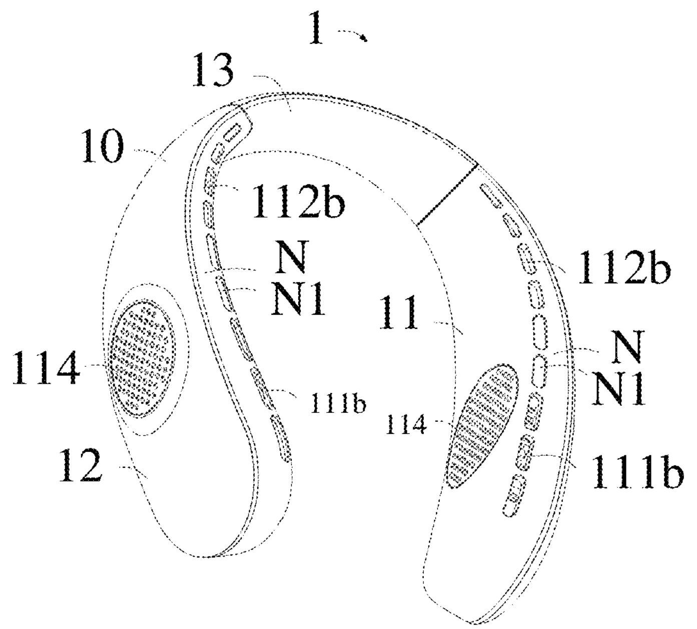
FIG. 17 is a schematic view of a neck fan according to an embodiment of the present disclosure.
Figure 18:
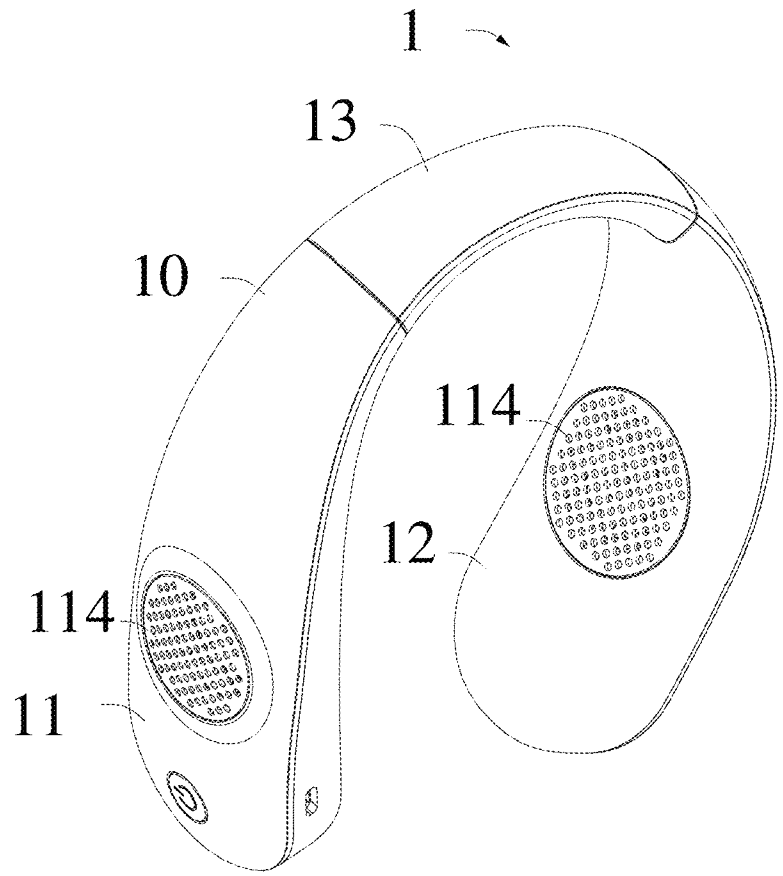
FIG. 18 is a schematic view of the neck fan shown in FIG. 17 from another view angle.

FIG. 17 is a schematic view of a neck fan according to an embodiment of the present disclosure. FIG. 18 is a schematic view of the neck fan shown in FIG. 17 from another view angle. The neck fan 1 includes an arc-shaped shell 10 and a fan assembly 20. The neck fan may be worn around the user's neck to free the user's hands.

Figure 19:
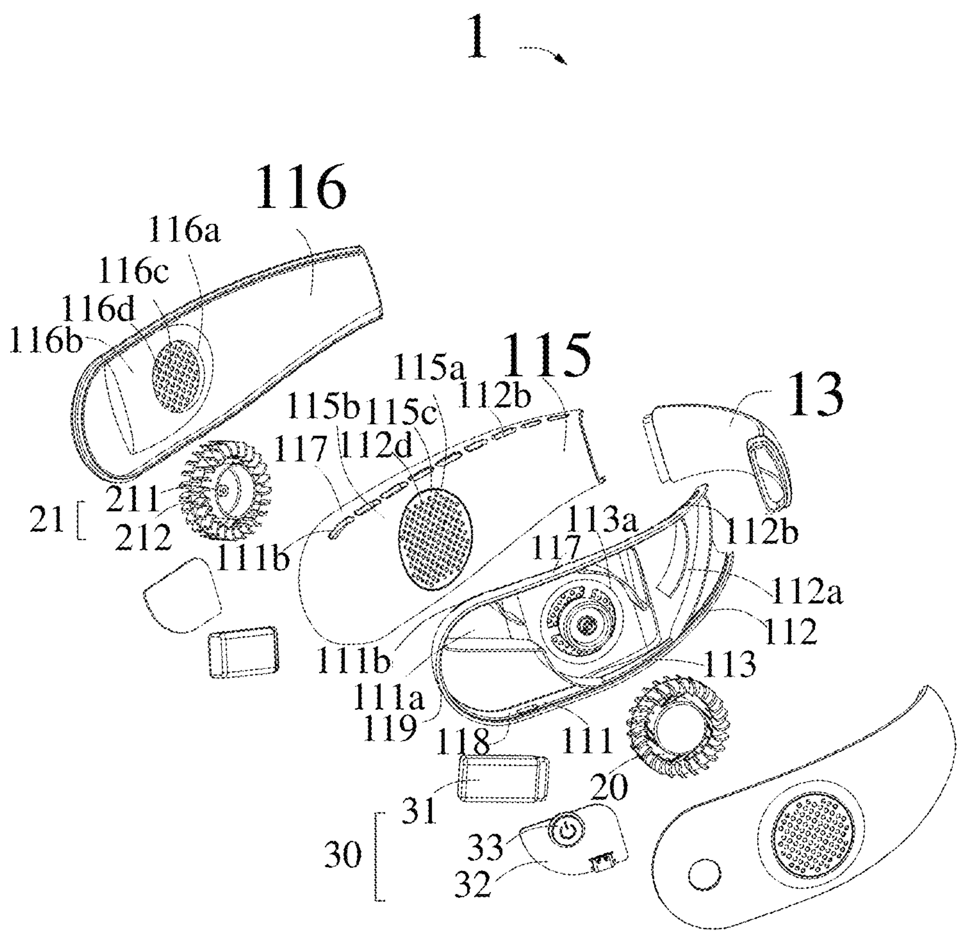
FIG. 19 is an enlarged view of the neck fan shown in FIG. 17.
Figure 20:
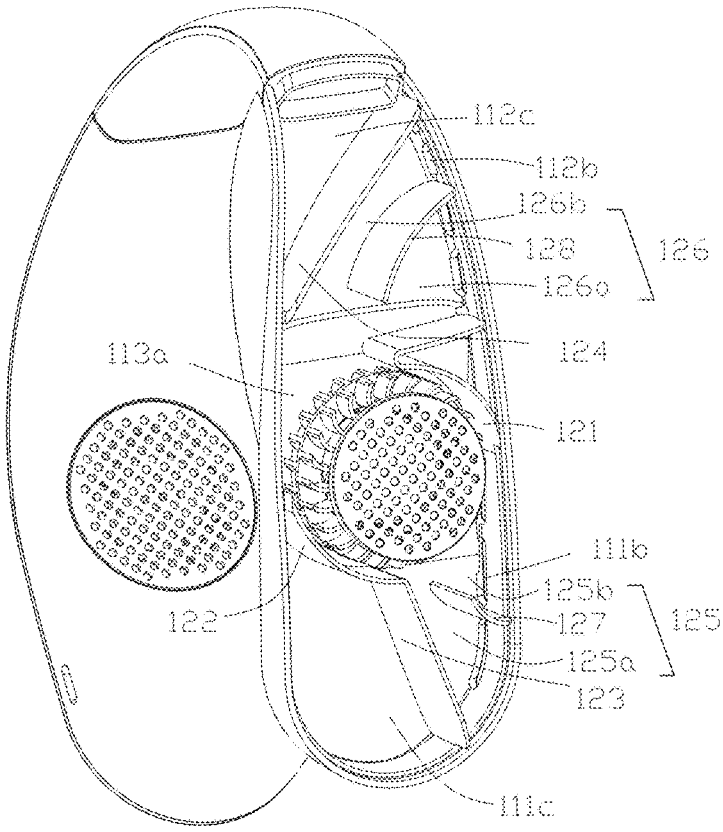
FIG. 20 is a schematic view of a portion of the neck fan shown in FIG. 17.
Figure 21:
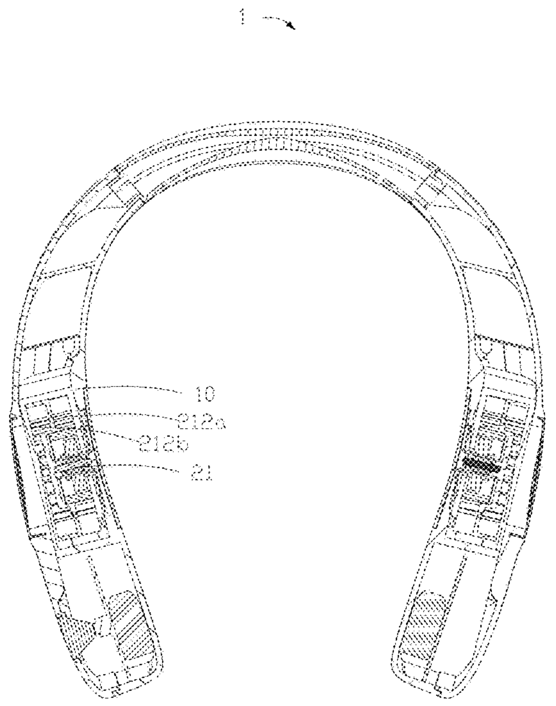
FIG. 21 is a cross section view of the neck fan shown in FIG. 17.

FIG. 19 is an enlarged view of the neck fan shown in FIG. 17, FIG. 20 is a schematic view of a portion of the neck fan shown in FIG. 17, and FIG. 21 a cross section view of the neck fan shown in FIG. 17. The shell 10 includes a first shell 11 and a second shell 12 opposite to the first shell 11. The first shell 11 and the second shell 12 may be configured at two opposite sides of the user's neck. At least one of the first shell 11 and the second shell 12 includes a first portion 111, a second portion 112 and a third portion 113. The third portion 113 is connected between the first portion 111 and the second portion 112. The first portion 111 defines a first receiving cavity 111*a* and a first air outlet 111*b* communicating with the first receiving cavity 111*a*. The second portion 112 defines a second receiving cavity 112*a* and a second air outlet 112*b* communicating with the second receiving cavity 112*a*. The third portion 113 defines a third receiving cavity 113*a*. The third receiving cavity 113*a* is between the first receiving cavity 111*a* and the second receiving cavity 112*a*, and is communicating with the first receiving cavity 111*a* and the second receiving cavity 112*a*. At least one of the first shell 11 and the second shell 12 defines an air inlet 114, communicating with at least one of the first receiving cavity 111*a*, the second receiving cavity 112*a*, and the third receiving cavity 113*a*. At least a portion of the fan assembly 20 is received in the third receiving cavity 113*a*, and is configured to guide the air from the air inlet 114 to the first air outlet 111*b* and the second air outlet 112*b*.

In the present embodiment, at least a portion of the fan assembly 20 is received in the third receiving cavity 113*a*, and the air is guided from the air inlet 114 to both the first air outlet 111*b* and the second air outlet 112*b*. Since the air flows to the outside of the fan through the first air outlet 111*b* and the second air outlet 112*b*, the amount of flowing air at the air outlets may be increased, and an air flowing efficiency may be increased, such that the user may be cooled rapidly. In addition, at least a portion of the fan assembly 20 is received in the third receiving cavity 113*a*, and wind generated from the fan assembly 20 is guided to both the first air outlet 111*b* and the second air outlet 112*b*. In this way, the wind generated from the fan assembly 20 may be utilized optimally, and a reduced wind efficiency caused by a large amount of wind flowing to an end of the shell may be avoided. In this way, noise of the neck fan may be reduced, and a loss in the amount of wind may be reduced, such that the air flowing efficiency may be increased. Further, the user's hair and other foreign matters may not be caught into the fan assembly 20 easily, such that the neck fan may be used safely and conveniently. Further, the fan assembly 20 is disposed between the first air outlet 111*b* and the second air outlet 112*b*. In this way, a reduced cooling effect of a neck fan in the art, which is caused by a free end of the neck fan being a wind-free zone E, may be solved. In the present embodiment, an end of the first portion 111 away from the third portion 113 defines the first air outlet 111*b*, enabling the air/wind to flow out of the fan through the first air outlet 111*b* to cover the user's face. Therefore, the user's mouth, nose, and so on may be cooled.

In some embodiments, the third portion 113 includes a wind-free region N. The wind-free region N locates between the first air outlet 111*b* and the second air outlet 112*b* and locates at a position corresponding to the fan assembly 20. The wind-free region N may not define any air outlet or define a blind-hole (such as a recess) that does not allow any air to flow out. Since the wind-free region N corresponds to the fan assembly 20, the wind generated by the fan assembly 20 may be distributed to the first air outlet 111*b* and the second air outlet 112*b*, which are defined at two sides of the fan assembly 20. In this way, the air flowing efficiency is increased, and the wind may be flowing gently. In addition, the wind-free region N prevents the wind from blowing towards the user's face directly. The wind-free region N separates the first air outlet 111*b* and the second air outlet 112*b*, such that the wind may be scattered to two sides, preventing an excessively large amount of wind from flowing towards the user's face hardly (which may be caused by the wind flowing through a single air outlet), such that facial paralysis may be avoided. Further, in the present embodiment, a position where the wind-free region N is arranged corresponds to the user's ear, such that the wind may not flow towards the user's ear directly, reducing wind noise and protecting the user's hearing.

Further, in the present embodiment, each of the first shell 11 and the second shell 12 includes the first portion 111, the second portion 112, and the third portion 113. Two fan assemblies 20 may be arranged. One of the two fan assemblies 20 may be received in the third receiving cavity 113*a* of the first shell 11 and may be configured to guide the air from the air inlet 114 of the first shell 11 to flow to the first air out let 111*b* and the second air outlet 112*b* of the first shell 11. The other one of the two fan assemblies 20 may be received in the third receiving cavity 113*a* of the second shell 12, and may be configured to guide the air from the air inlet 114 of the second shell 12 to flow to the first air out let 111*b* and the second air outlet 112*b* of the second shell 12. It shall be understood that the first shell 11 and the second shell 12, which may be arranged at two opposite sides of the user's neck, may be structurally symmetric with each other. That is, each of the first shell 11 and the second shell 12 is arranged with the first portion 111, the second portion 112, and the third portion 113. One fan assembly 20 is received in each of the third portion 113 of the first shell 11 and the third portion 113 of the second shell 12. While the neck fan 1 is working, the two fan assemblies 20, which are arranged at two opposite sides of the user's neck, may guide the air from the air inlet 114 of the first shell 11 to flow to the first air out let 111*b* and the second air outlet 112*b* of the first shell 11 and guide the air from the air inlet 114 of the second shell 12 to flow to the first air out let 111*b* and the second air outlet 112*b* of the second shell 12. Since each of the first shell 11 and the second shell 12 includes the first portion 111, the second portion 112, and the third portion 113, and the fan assembly 20 is received in each of the third portion 113 of the first shell 11 and the third portion 113 of the second shell 12, air flowing from the air inlet 114 of the first shell 11 to the first air outlet 111*b* and the second air outlet 112*b* of the first shell 11 and air flowing from the air inlet 114 of the second shell 12 to the first air outlet 111*b* and the second air outlet 112*b* of the second shell 12 may occur simultaneously. In this way, the amount of air flowing to the inside of the neck fan and the amount of air flowing out of the neck fan may be increased, such that the user may be cooled rapidly. Further, the wind may be blown to two sides of the user's neck, improving the user's experience.

In more detail, the fan assembly 20 includes a turbine fan 21. The turbine fan 21 includes a fan shaft 211 and a plurality of turbine blades 212 surrounding the fan shaft 211. An air flowing direction of the turbine fan 21 is perpendicular to an extending direction of the fan shaft 211. In this way, a large amount of wind may be generated by occupying a relatively small space, such that the air flowing efficiency of the neck fan 1 may be increased. By configuring the turbine fan 21 for the fan assembly 20, noise generated while the neck fan is being in use may be reduced effectively, and at the same time, the air flowing efficiency of the neck fan 1 may be increased.

In detail, the plurality of turbine blades 212 may include a first end face 212*a* and a second end face 212*b*, and the first end face 212*a* and the second end face 212*b* are disposed along the extending direction of the fan shaft 211. A distance from the first end face 212*a* to the shell 10 may be in a range of 1 mm to 6 mm, and/or a distance from the second end face 212*b* to the shell 10 may be in a range of 1 mm to 6 mm. A diameter of the turbine fan 21 may be in a range of 35 mm to 45 mm. A thickness of the turbine fan 21 along the extending direction of the fan shaft 211 may be in a range of 10 mm to 25 mm. In some embodiments, the distance from the first end face 212*a* to the shell 10 may be 1 mm, and/or the distance from the second end face 212*b* to the shell 10 may be 1 mm. The air flowing efficiency of the fan assembly 20 may be increased by setting three parameters for the neck fan. The three parameters may include: the distance from the first end face 212*a* to the shell 10 being in a range of 1 mm to 6 mm and/or the distance from the second end face 212*b* to the shell 10 being in a range of 1 mm to 6 mm; the diameter of the turbine fan 21 being in a range of 35 mm to 45 mm; and the thickness of the turbine fan 21 along the extending direction of the fan shaft 211 being in a range of 10 mm to 25 mm. In some embodiments, the distance from the first end face 212*a* to the shell 10 may be 1 mm, and/or the distance from the second end face 212*b* to the shell 10 may be 1 mm, and in this way, the air flowing efficiency of the neck fan 1 may be increased.

Further, each of the first portion 111, the second portion 112, and the third portion 113 may include a first inner plate 115, a first outer plate 116, a first connection plate 117, and a second connection plate 118. The first inner plate 115 may be disposed near the user's neck. The first outer plate 116 may be opposite to the first inner plate 115. The first connection plate 117 may be connected between the first inner plate 115 and the first outer plate 116, and may be disposed near the user's head. The second connection plate 118 may be opposite to the first connection plate 117. The first portion 111 may further include a first end plate 119 disposed between the first inner plate 115, the first outer plate 116, the first connection plate 117, and the second connection plate 118. The air inlet 114 may be defined in at least one of the first inner plate 115 and the first outer plate 116 of the third portion 113. The first air outlet 111*b* may be defined in the first inner plate 115 of the first portion 111. The second air outlet 112*b* in the first inner plate 115 of the second portion 112. The first end face 212*a* may correspond to the first inner plate 115 of the third portion 113. The second end face 212*b* may correspond to the first outer plate 116 of the third portion 113. The fan shaft 211 may extend along a direction from the first inner plate 115 to the fists outer plate 116. In the present embodiment, the air inlet 114 is defined in at least one of the first inner plate 115 of the third portion 113 and the first outer plate 116 of the third portion 113, the first air outlet 111*b* may be defined in the first inner plate 115 of the first portion 111, and the second air outlet 112*b* in the first inner plate 115 of the second portion 112. In this way, the fan assembly 20 is disposed between the first air outlet 111*b* and the second air outlet 112*b*. The fan assembly 20 may drive the air/wind to flow from the air inlet 114 to the first air outlet 111*b* and the second air outlet 112*b*, which are defined at two opposite sides of the fan assembly 20. Air flowing through the first air outlet 111*b* does not interfere air flowing through the second air outlet 112*b*. In this way, the loss in the air flowing may be reduced, improving the air flowing efficiency of the neck fan 1.

Further, the air inlet 114 may be defined each of the first inner plate 115 and the first outer plate 116 of the third portion 113. In this way, wind stifling caused by only one of the first inner plate 115 and the first outer plate 116 defining the air inlet 114 may be avoided, allowing the air to fluently flow through any air duct between any air inlet and any air outlet, such that the wind may flow more fluently, and wind noise may be reduced. The first inner plate 115 of the third portion 113 may include a first body portion 115*b* and a first cover plate 115*c*. The first body portion 115*b* defines a first opening 115*a*. The first cover plate 115*c* is mounted at the first opening 115*a*. The air inlet 114 may include a plurality of first air inlets 115*d* defined in the first cover plate 115*c*. Each of the first opening 115*a* and the first cover plate 115*c* may be circular. The plurality of first air inlets 115*d* may be evenly distributed in the first cover plate 115*c*. The first outer plate 116 of the third portion 113 may include a second body portion 116*b* and a second cover plate 116*c*. The second body portion 116*b* defines a second opening 116*a*. The second cover plate 116*c* is mounted at the second opening 116*a*. The air inlet 114 may include a plurality of second air inlets 116*d* defined in the second cover plate 116*c*. Each of the second opening 116*a* and the second cover plate 116*c* may be circular. The plurality of second air inlets 116*d* may be evenly distributed in the second cover plate 116*c*. It shall be understood that, in the present embodiment, the fan assembly 20 includes the turbine fan 21, air flowing in/out of the turbine fan 21 may be in a toroidal turbine manner. Therefore, the first opening 115*a*, the first cover plate 115*c*, the second opening 116*a*, and the second cover plate 116*c* may be configured be circular, such that the openings and the cover plates may be optimally adapted with the air flowing of the turbine fan 21, reducing the loss in the air flowing. Furthermore, the plurality of first air inlets 115*d* are evenly distributed in the first cover plate 115*c*, and the plurality of second air inlets 116*d* are evenly distributed in the second cover plate 116*c*, such that air out of the turbine fan 21 may flow more fluently and evenly, and the air flowing efficiency of the neck fan 1 may be improved.

Further, the neck fan 1 may further include a first partition portion 121, a second partition portion 122, a first wind guide portion 123, and a second wind guide portion 124. The first partition portion 121 is at least partially received in the third receiving cavity 113*a* and covers a side of the fan assembly 20 near the user's face and the second portion 112. The second partition portion 122 covers an outer periphery of the fan assembly 20 and is opposite to the first partition portion 121. The first wind guide portion 123 is connected to the second partition portion 122 and is received in the first receiving cavity 111*a*. The second wind guide portion 124 is received in the second receiving cavity 112*a*. The first wind guide portion 123 divides the first receiving cavity 111*a* into a first sub-cavity 111*c* and a first air duct 125 communicating with the first air outlet 111*b* of the first portion 111. The second wind guide portion 124 divides the second receiving cavity 112*a* into a second sub-cavity 112*c* and a second air duct 126 communicating with the second air outlet 112*b* of the second portion 112. It shall be understood that the first partition plate 121 and the second partition plate 122 are disposed at two opposite sides of the fan assembly 20, the wind generated from the fan assembly 20 may be guided by the first partition plate 121 and the second partition plate 122 to flow to the first wind guide portion 123 and the second wind guide portion 124, and subsequently, the wind may be guided by the first wind guide portion 123 and the second wind guide portion 124 to flow to the first air duct 125 and the second air duct 126 to reach the first air outlet 111*b* and the second air outlet 112*b* respectively. By arranging the first partition portion 121, the second partition portion 122, the first wind guide portion 123, and the second wind guide portion 124, the first receiving cavity 111*a* is divided, the first air duct 125 is defined to communicate with the first air outlet 111*b* of the first portion 111, the second receiving cavity 112*a* is divided, and the second air duct 126 is defined to communicate with the second air outlet 112*b* of the second portion 112. The first air duct 125 and the second air duct 126 may be defined to guide the wind generated from the fan assembly 20 to the first air outlet 111*b* and the second air outlet 112*b* respectively, reducing the loss in the air flowing, allowing the air to flow to various positions of the user accurately, and increasing the air flowing efficiency.

Further, the neck fan 1 may include a first auxiliary guide plate 127 and a second auxiliary guide plate 128. The first auxiliary guide plate 127 is configured to divide the first air duct 125 into a first sub-duct 125*a* and a second sub-duct 125*b*. More than one first air outlets 111*b* may be defined, and more than one second air outlets 112*b* may be defined. The first sub-duct 125*a* may communicate with a portion of the more than one first air outlets 111*b* of the first portion 111, and the second sub-duct 125*b* may communicate with another portion of the more than one first air outlets 111*b* of the first portion 111. The second auxiliary guide plate 128 is configured to divide the second air duct 126 into a third sub-duct 126*a* and a fourth sub-duct 126*b*. The third sub-duct 126*a* may communicate with a portion of the more than one second air outlets 112*b* of the second portion 112, and the fourth sub-duct 26*b* may communicate with another portion of the more than one second air outlets 112*b* of the second portion 112. By arranging the first auxiliary guide plate 127, the first air duct 125 is divided into the first sub-duct 125*a* and the second sub-duct 125*b*. By arranging the second auxiliary guide plate 128, the second air duct 126 is divided into the third sub-duct 126*a* and the fourth sub-duct 126*b*. In this way, the wind may be evenly distributed to the first air outlets 111*b* and the second air outlets 112*b*, reducing the loss in the air flowing, allowing the air to flow to various positions of the user accurately, and increasing the air flowing efficiency.

Further, an end portion of the first auxiliary guide plate 127 near the air outlets 111*b* and 112*b* and an end portion of the second auxiliary guide plate 128 near the air outlets 111*b* and 112*b* may be substantially perpendicular to a wall of the shell defining the air outlets 111*b* and 112*b*. In this way, after the wind is guided by the first auxiliary guide plate 127 and the second auxiliary guide plate 128, the wind may be blown out of the neck fan along a direction substantially perpendicular a plane where the first connection plate 117 is arranged. In this way, the wind may be blown to the user's face straightly. In the art, the wind may be blown to the user's face non-straightly, and the wind from various air outlets may interfere with each other. Therefore, in the present embodiment, a force of the wind may not be reduced.

Further, the neck fan 1 may further include an electronic control assembly 30. The electronic control assembly 30 may include at least one of a battery 31, a circuit board 32, and a control switch 33. At least a portion of the electronic control assembly 30 is received in the first sub-cavity 111*c* or the second sub-cavity 112*c*. The electronic control assembly 30 is configured to supply power for the neck fan 1, allowing the neck fan 1 to be portably used. In addition, by receiving at least a portion of the electronic control assembly 30 in the first sub-cavity 111*c* and the second sub-cavity 112*c*, the neck fan 1 may be used safely.

Further, the shell 10 may further include a connection member 13. The connection member 13 may be connected between the first shell 11 and the second shell 12. The connection member 13 may be a flexible connection member that can be bent manually. By arranging the connection member 13 to be connected between the first shell 11 and the second shell 12, and by allowing the flexible connection member 13 to be bent manually and fixed at a certain bending angle, the user may wear the neck fan 1 more comfortably, since the user may adjust the bending portion of the neck fan based on the size of the user's neck. To be noted that, in some embodiments, the connection member 13 may be omitted. That is, the first shell 11 may be connected to the second shell 12 directly; alternatively, the first shell 11 and the second shell 12 may be integrally formed as one piece, the first inner plate 115 and the first outer plate 116 may be uncoverable, and the neck fan 1 may be assembled and used through the uncoverable first inner plate 115 and the uncoverable first outer plate 116; alternatively, the first inner plate 115 of the first shell 11 and the first inner plate 115 of the second shell 12 may be integrally formed as one piece, and the first outer plate 116 may be uncoverable; alternatively, the first outer plate 116 of the first shell 11 and the first outer plate 116 of the second shell 12 may be integrally formed as one piece, and the first inner plate 115 may be uncoverable.

To be noted that, in the present embodiment, the electronic control assembly 30 is received in the first sub-cavity 111*c*. While using the neck fan 1, the end portion of the first portion 111 may be suspended. Therefore, heat generated by the electronic control assembly 30 may be prevented from transferring to the user, improving the user experience.

Figure 22:
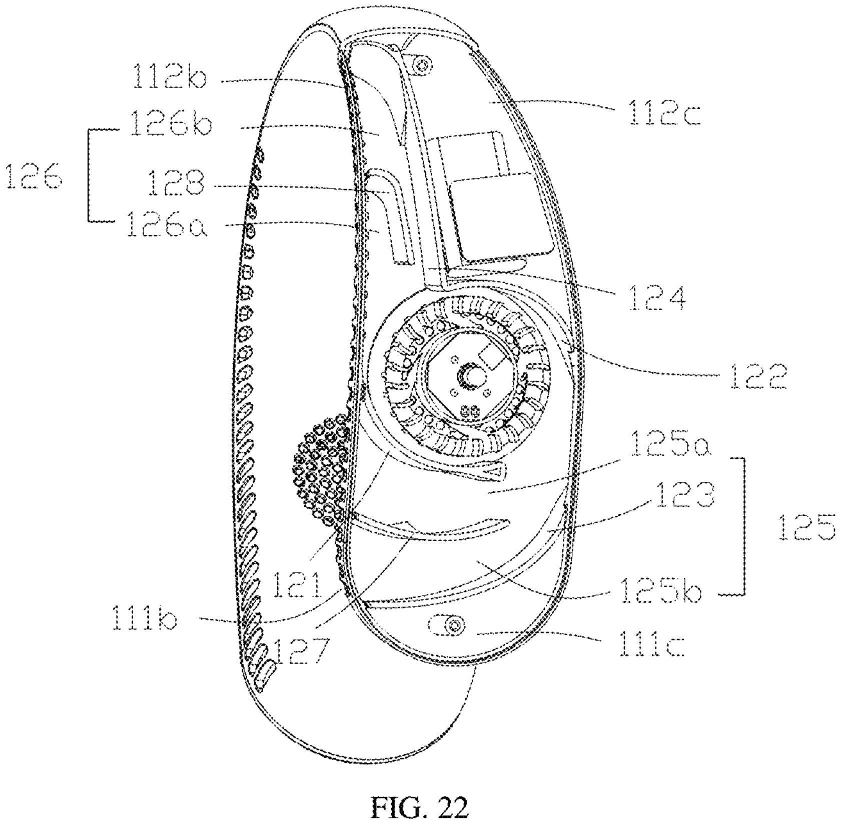
FIG. 22 is a cross section view of a neck fan shown according to another embodiment of the present disclosure.

As shown in FIG. 22, in the present embodiment, the first partition plate 121 is at least partially received in the third receiving cavity 113*a* and covers the side of the fan assembly near the user's face and the first portion 111. The second partition portion 122 covers the outer periphery of the fan assembly 20 and is opposite to the first partition portion 121. The first wind guide portion 123 is received in the first receiving cavity 111*a*. The second wind guide portion 124 is received in the second receiving cavity 112*a* and is connected to the second partition portion 122. The first wind guide portion 123 divides the first receiving cavity 111*a* into the first sub-cavity 111*c* and the first air duct 125 communicating to the first air outlet 111*b* of the first portion. The second wind guide portion 124 divides the second receiving cavity 112*a* into the second sub-cavity 112*c* and the second air duct 126 communicating to the second air outlet 112*b* of the second portion.

In particular, to the extent understandable to those in the centrifugal fan technical field, as shown in FIG. 22, the second partition portion 122 serves as the pressurizing plate 271 shown in FIG. 4, the second wind guide portion 124 serves as the wind guiding plate 272 shown in FIG. 4, and the second partition portion 122 and the second wind guide portion 124 cooperatively form the vortex tongue structure 27 shown in FIG. 4.

The first auxiliary guide plate 127 is configured to divide the first air duct 125 into the first sub-duct 125*a* and the second sub-duct 125*b*. The first sub-duct 125*a* communicates with a portion of the more than one air outlets 111*b* of the first portion 111. The second sub-duct 125*b* communicates with another portion of the more than one air outlets 111*b* of the first portion 111. The second auxiliary guide plate 128 is configured to divide the second air duct 126 into the third sub-duct 126*a* and the fourth sub-duct 126*b*. The third sub-duct 126*a* communicates with a portion of the more than one air outlets 112*b* of the second portion 112. The fourth sub-duct 126*b* communicates with another portion of the more than one air outlets 112*b* of the second portion 112. By arranging the first auxiliary guide plate 127, the first air duct 125 is divided into the first sub-duct 125*a* and the second sub-duct 125*b*. By arranging the second auxiliary guide plate 128, the second air duct 126 is divided into the third sub-duct 126*a* and the fourth sub-duct 126*b*. In this way, the wind may be evenly distributed to the first air outlets 111*b* and the second air outlets 112*b*, reducing the loss in the air flowing, allowing the air to flow to various positions of the user accurately, and increasing the air flowing efficiency.

In the present embodiment, as shown in the cross section of FIG. 22, the fan assembly 20 may rotate clockwise. The wind may flow out of the fan assembly 20 from a position near the second connection plate 118 along a tangent direction. Subsequently, the wind may be driven to the second air duct 126 due to rotational inertia. Further, the wind may flow along the second wind guide portion 124 and the second auxiliary guide plate 128, and the curved second auxiliary guide plate 128 may further accelerate a speed of the wind. At last, the wind may flow out of the neck fan through the first air outlet 111*b* away from the second connection plate 118. In this way, the wind flowing out of the first air outlet 111*b* may be different from the wind flowing out of the second air outlet 112*b*, where the wind is compressed to flow out of the second air outlet 112*b*. In this way, a speed and a force of the wind flowing out of the air outlets may be improved.

In some embodiments, the neck fan may include the fan assembly 20 and a shell portion 11 or 12. The shell portion 11 or 12 may include the first portion 111, the second portion 112, and the third portion 113. The third portion 113 is connected between the first portion 111 and the second portion 112. The first portion 111 defines the first receiving cavity 111 and the first air outlet 111*b* communicating with the first receiving cavity 111*a*. The second portion 112 defines the second receiving cavity 112*a* and the second air outlet 112*b* communicating with the second receiving cavity 112*a*. The third portion 113 defines the third receiving cavity 113*a*. The third receiving cavity 113*a* is between the first receiving cavity 111*a* and the second receiving cavity 112*a*, and communicates with the first receiving cavity 111*a* and the second receiving cavity 112*a*. The shell portion 11 or 12 defines the air inlet 114 communicating with at least one of the first receiving cavity 111*a*, the second receiving cavity 112*a*, and the third receiving cavity 113*a*. The fan assembly 20 is at least partially received in the third receiving cavity 113*a* and is configured to guide the air from the air inlet 114 to flow to the first air outlet 111*b* and the second air outlet 112*b*.

In the present embodiment, the fan assembly 20 is at least partially received in the third receiving cavity 113*a* and is configured to guide the air from the air inlet 114 to flow to the first air outlet 111*b* of the first portion 111 and the second air outlet 112*b* of the second portion 112 respectively. Since the air is flowing out of the first air outlet 111*b* and the second air outlet 112*b*, the amount of air flow is increased, the air flowing efficiency is increased, and the user may be cooled rapidly. Further, the wind generated from the fan assembly 20 is flowing to two opposite sides of the fan assembly to the first air outlet 111*b* and the second air outlet 112*b* respectively, avoiding a reduced air flowing efficiency caused by a large amount of air flowing to the end portion of the shell, such that the wind noise may be reduced, the wind loss may be reduced, and the air flowing efficiency may be increased. In addition, the user's hair may not be caught by the fan assembly 20 easily, enabling the user to use the neck fan safely. Further, the fan assembly 20 is disposed between the first air outlet 111*b* and the second air outlet 112*b*. A reduced cooling effect of a neck fan in the art, which is caused by a free end of the neck fan being a wind-free zone E, may be solved. In the present embodiment, the end of the first portion 111 away from the third portion 113 defines the first air outlet 111*b*, enabling the air/wind to flow out of the fan through the first air outlet 111*b* to cover the user's face completely. Therefore, the user's mouth, nose, and so on may be cooled.

Figure 23:
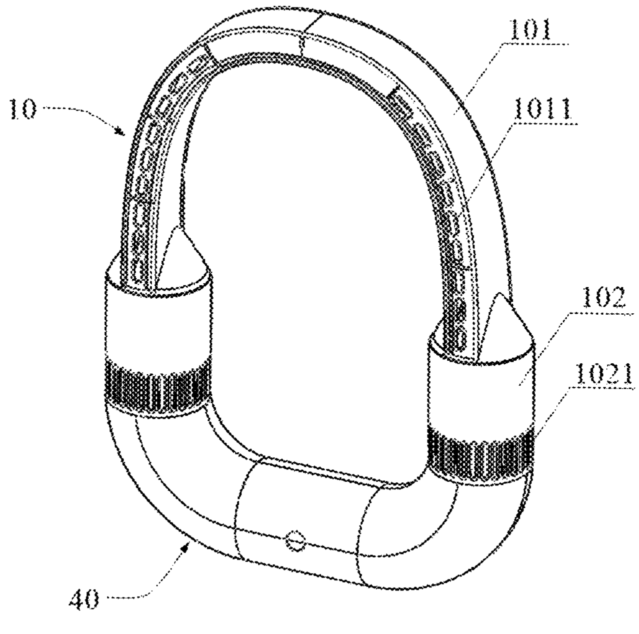
FIG. 23 is a structural schematic view of a neck fan according to an embodiment of the present disclosure.
Figure 24:
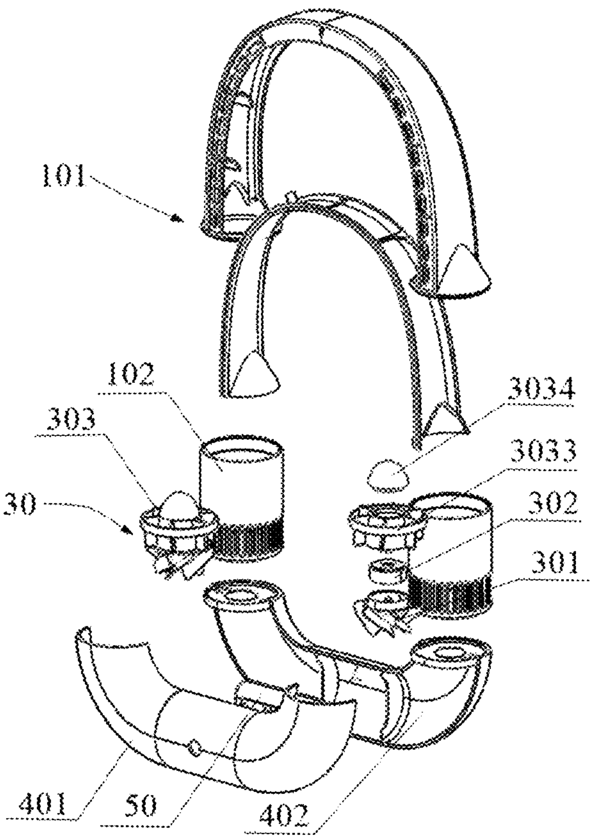
FIG. 24 is an exploded view of a neck fan according to an embodiment of the present disclosure.
Figure 25:
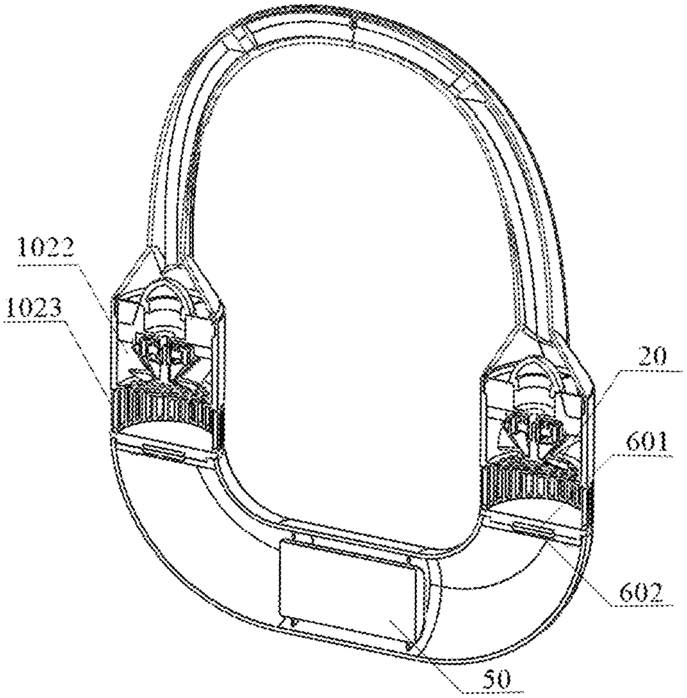
FIG. 25 is a cross section view of a neck fan according to an embodiment of the present disclosure.

As shown in FIGS. 23-25, the neck fan includes an arc-shaped shell 10 and a diagonal fan assembly 30. The shell 10 includes an air inlet portion shell 102 and an air outlet portion shell 101 connected to the air inlet portion shell 102. In the present embodiment, the air outlet portion shell 101 may be adapted to and worn to the user's neck. The air inlet portion shell 102 is connected to each of two ends of the air outlet portion shell 101. The air inlet portion shell 102 defines a receiving space. The air outlet portion shell 101 defines an air outlet 1011. A partition plate 20 is received inside the air inlet portion shell 102. The partition plate 20 defines a plurality of through holes 201. A side wall of the air inlet portion shell 102 is disposed between the partition plate 20 and an end face of the air inlet portion shell 102 away from the air outlet portion shell 101. The side wall defines an air inlet 1021. The diagonal fan assembly 30 is received in the air inlet portion shell 102 and is configured to guide the external air to flow through the through holes 201 to the air outlet 1011.

The air may enter the diagonal fan assembly 30 along a direction inclined to an axis of the diagonal fan assembly. The diagonal fan assembly 30 may drive the air, which flows along the direction inclined to the axis of the diagonal fan assembly 30, to flow along a radial direction. In this way, the loss of air flowing may be reduced, and the amount of air flowing may be improved. Further, a wind pressure and a wind speed at the air outlet 1011 may be uniform, improving the user's experience. The external air may enter the neck fan through the through holes 201 of the partition plate 20, such that the air may flow into the neck fan uniformly, reducing the wind noise.

As shown in FIGS. 23-25, the air outlet portion shell 101 and the air inlet portion shell 102 may be detachably connected, through a buckle or magnetics. Detachable connection allows the diagonal fan assembly 30 in the air inlet portion shell 102 to be maintained easily.

As shown in FIGS. 23-25, the partition plate 20 may be disposed at a middle portion of the air inlet portion shell 102, dividing the air inlet portion shell 102 into a placement portion 1022 and an air inlet portion 1023. A side wall of the air inlet portion 1023 defines the air inlet 1021. Defining the air inlet 1021 in the side wall may reduce the wind noise.

The diagonal fan assembly 30 may guide the air from the air inlet 1021 to flow through the through holes 201 to the air outlet 1011. The partition plate 20 allows the air to flow from the air inlet 1021 through the through holes, enabling the air to uniformly enter the neck fan, reducing the wind noise.

The placement portion 1022 and the air inlet portion 1023 may be integrally formed as one piece.

In some embodiments, the placement portion 1022 and the air inlet portion 1023 may be detachably connected. The partition plate 20 is disposed on an end face of the air inlet portion 1023 near the placement portion 1022 or disposed on an end face of the placement portion 1022 near the air inlet portion 1023.

In some embodiments, the diagonal fan assembly 30 is at least partially arranged in the placement portion 1022 and is configured to guide the air from the air inlet 1021 to flow through the through holes 201 to the air outlet 1011. The diagonal fan assembly 30 may include an impeller 301 and a motor 302 driving the impeller 301 to rotate. The impeller 301 may include a first wind guide cone 3011 and diagonal blades 3014 arranged on the first wind guide cone 3011. The first wind guide cone 3011 is configured to guide the air.

Figure 26:
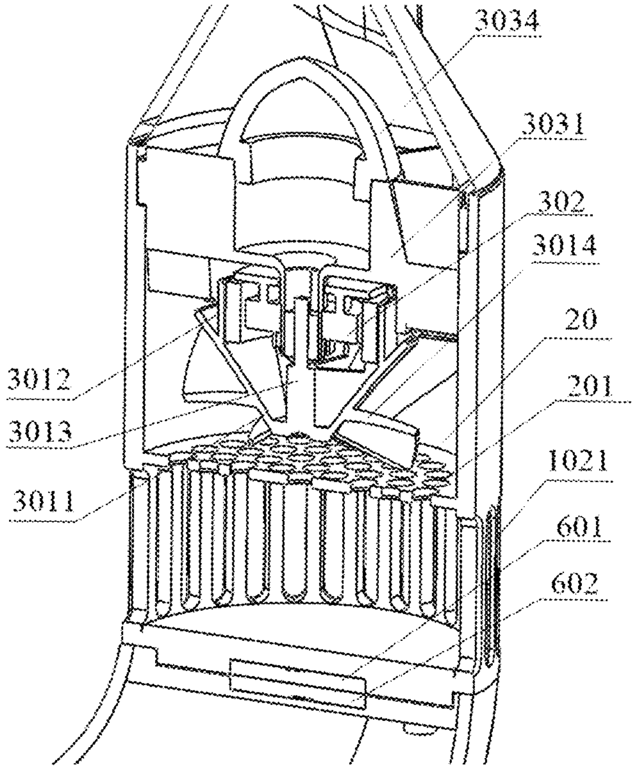
FIG. 26 is a cross section view of a diagonal fan of a neck fan according to an embodiment of the present disclosure.
Figure 27:
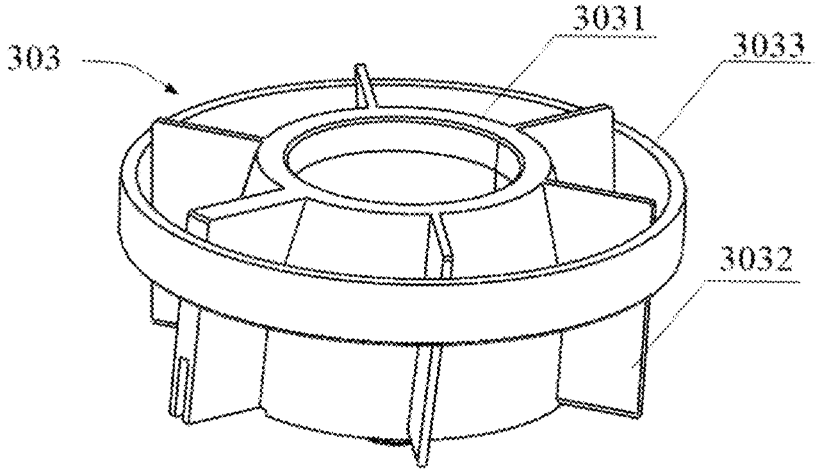
FIG. 27 is a structural schematic view of a wind guide portion of a neck fan according to an embodiment of the present disclosure.

In some embodiments, as shown in FIGS. 25-27, an inner wall of the first wind guide cone 3011 facing the motor 302 may extend along a loop to form a placement column 3012. A rotation shaft 3013 is arranged inside the first wind guide cone 3011. A diameter of the placement column 3012 is less than a diameter of a sleeve 3031. The placement column 3012 is at least partially received in the sleeve 3031 and surrounds an outer periphery of the motor 302.

As shown in FIGS. 24-26, the diagonal fan assembly 30 may further include a wind guide member 303. The wind guide member 303 may include the sleeve 3031, stator blades 3032, a wind guide ring 3033, and a second wind guide cone 3034. The stator blades 3032 are arranged on an outer wall of the sleeve 3031. The wind guide ring 3033 is connected to the stator blades 3032 along a circumferential direction. The second wind guide cone 3034 is arranged at an end face of the sleeve 3031 and faces the air outlet portion shell 101. The motor 302 may be received in the sleeve 3031.

The second wind guide cone 3034 may collect the air, which has entered the neck fan, and guide the air to flow into the air outlet portion shell 101. In this way, the air may flow into the air outlet portion shell 101 uniformly, reducing the wind noise. After receiving the motor 302 into the sleeve 3031, the sleeve 3031 may be sealed, improving air tightness of the neck fan. In this way, the motor 302 may be protected, and the motor may be safe while the neck fan is being used.

In some embodiments, the diagonal fan assembly 30 may be completely received in the air inlet portion shell 102.

In some embodiments, a portion of the diagonal fan assembly 30 may be received in the air inlet portion shell 102, and another portion of the diagonal fan assembly 30 may extend to be received in the air outlet portion shell 101. For example, the impeller 301 and the motor 302 may be received in the air inlet portion shell 102, and the wind guide member 303 may extend to be received in the air outlet portion shell 101.

In some embodiments, when the second wind guide cone 3034 of the wind guide member 303 extends to be received in the air outlet portion shell 101, the end face of the air outlet portion shell 101 near the air inlet portion shell 102 defines an expansion opening, such that the air outlet portion shell 101 may be adaptively connected to the air inlet portion shell 102 and receive the second wind guide cone 3034.

As shown in FIGS. 23-25, the neck fan may further include an external shell 40 detachably connected to the air inlet shell portion 102. A power assembly 50 may be received in the external shell 40 and/or the air outlet portion shell 101. The power assembly 50 may be electrically connected to the diagonal fan assembly 30. The power assembly 50 may be a USB port and/or a rechargeable battery.

In some embodiments, a control plate may be received in the external shell 40 and/or the air outlet portion shell 101. The battery may be connected to the control plate. The control plate may b connected to the diagonal fan assembly 30. In this way, the control plate and the battery may be received inside the arc-shaped shell 10.

The rechargeable battery may be received in the external shell 40. A rechargeable battery having a relatively large capacity may be arranged, based on actual demands. In this way, the neck fan may operate for a relatively long period of time. While manufacturing, the battery may be received in the arc-shaped shell 10 only or in the external shell 40 only; alternatively, one battery may be received in both the arc-shaped shell 10, and another battery may be received in the external shell 40. In this way, when the battery in the arc-shaped shell 10 is out of power, the battery in the external shell 40 may supply the power, such that the neck fan may operate for a relatively long period of time.

In some embodiments, the external shell 40 may be arc shaped. The external shell 40 may include a first shell 401 and a second shell 402 fastened with the first shell 401. The power assembly 50 and/or the control plate may be disposed between the first shell 401 and the second shell 402.

Since the external shell 40 is detachably connected to the air inlet portion shell 102, the power assembly 50 in the external shell 40 may be maintained or recharged easily. When the rechargeable battery is received in the arc-shaped shell 10, the rechargeable battery in the external shell 40 may serve as a backup battery, such that the neck fan may operate for a relatively long period of time.

The external shell 40 may be detachably connected to the air inlet portion shell 102 through a buckle or the like.

Figure 28:
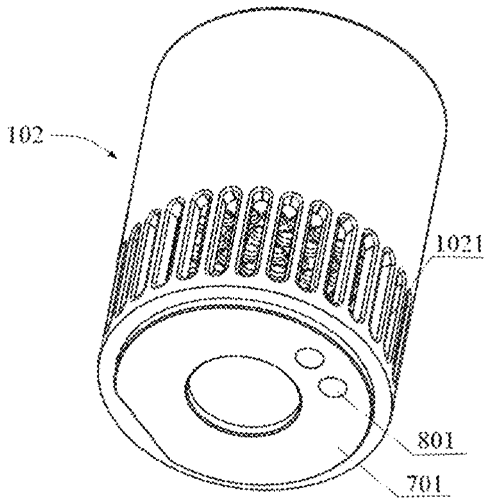
FIG. 28 is a structural schematic view of an air inlet section of a neck fan according to an embodiment of the present disclosure.
Figure 29:
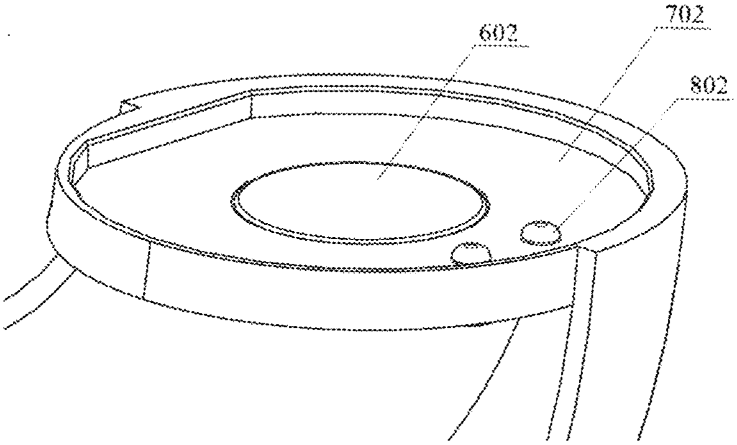
FIG. 29 is a structural schematic view of an end of an external shell of a neck fan according to an embodiment of the present disclosure.

In some embodiments, as shown in FIGS. 28 and 29, the air inlet portion 1023 may include two end walls away from two placement portions 1022. A first magnetic member 601 may be arranged on each of the two end walls, and a second magnetic member 602 may be arranged on each of two end faces of the external shell 40. The first magnetic member 601 may be align to and attracted to the second magnetic member 602.

Each of the first magnetic member 601 and the second magnetic member 602 may be a magnet. Alternatively, one of the first magnetic member 601 and the second magnetic member 602 may be the magnet, and the other one of the first magnetic member 601 and the second magnetic member 602 may be a metal (such as iron, iron alloy, and the like) that can be attracted by the magnet.

Magnetic attraction between the first magnetic member 601 and the second magnetic member 602 allows the external shell 40 to be detachably connected to the air inlet portion shell 102, such that the external shell 40 may be connected quickly, and may be detached easily.

As shown in FIGS. 26, 28 and 29, an end wall of the placement portion 1022 may extend downwardly to form a tab 701. An upper end of the external shell 40 may be recessed inwardly to define a slot 702 for adaptively receiving the tab 701. Receiving the tab 701 into the slot 702 allows the external shell 40 to be stably connected to the air inlet portion shell 102.

As shown in FIGS. 28 and 29, the external shell 40 is detachably connected to the air inlet portion shell 102. In the present embodiment, one of the end wall of the placement portion 1022 and the end face of the external shell 40 may be arranged with a probe 801, and the other one of the end wall of the placement portion 1022 and the end face of the external shell 40 may be arranged with a contact 802. When the external shell 40 is attractively connected to the air inlet portion shell 102, the contact 802 contacts the probe 801 for conducting. In this way, the rechargeable battery in the external shell 40 is electrically connected to the motor 302 of the diagonal fan assembly 30.

According to the present embodiment, the diagonal fan assembly 30 may guide the air, which enters the neck fan along the direction inclined to the axis of the fan assembly 30, to flow along the radial direction, such that the loss in the air flowing may be reduced, and the amount of air flowing may be increased. The wind pressure and the wind speed at the air outlet may be uniform. In addition, the battery may be received in at least one of the air outlet portion shell and the external shell 40, such that operation duration of the neck fan may be improved significantly.

FIGS. 30-37 show a neck fan according to another embodiment of the present disclosure.

Figure 30:
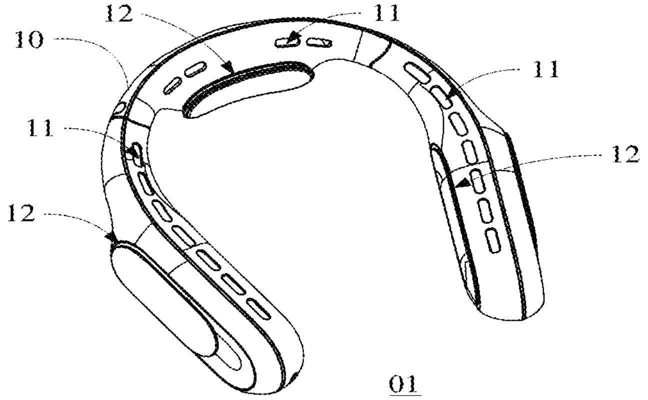
FIG. 30 is a structural schematic view of a neck fan according to an embodiment of the present disclosure.

FIG. 30 is a structural schematic view of a neck fan according to an embodiment of the present disclosure. In the present embodiment, a neck fan 01 includes a bracket assembly 10 and a wind turbine positioned arranged inside the bracket assembly 10. The bracket assembly 10 defines an air outlet 11 and an air inlet 12. The wind turbine drives external air to flow to an inside of the bracket assembly 10 through the air inlet 12, and to further flow to the air outlet 11, such that the air may flow to an outside of the neck fan through the air outlet 11.

In some embodiments, a plurality of air outlets 11 may be defined. Defining the plurality of air outlets 11 may increase a coverage area of air flowing of the neck fan 01. A plurality of air inlets 12 may be defined. Defining the plurality of air inlets 12 may increase an air intake rate of the neck fan 01.

The bracket assembly 10 is configured to hang the neck fan 01 around the user's neck. For example, in the present embodiment, the bracket assembly 10 is circular shaped, such that the bracket assembly 10 may well hang around the user's neck, and the air outlets 11 may face the user's cheek or neck. In this way, while the user is wearing the neck fan 01, the air out of the air outlets 11 may flow towards the user's cheek or neck.

Figure 31:
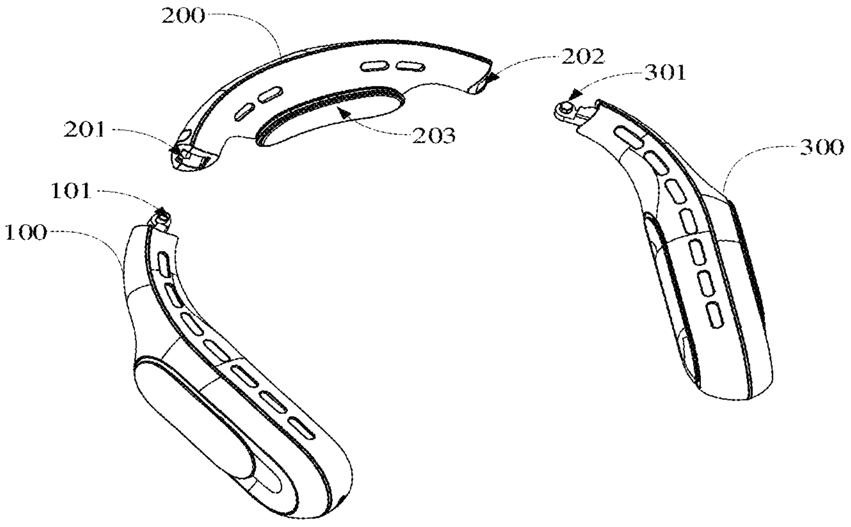
FIG. 31 is an exploded view of the neck fan shown in FIG. 30.

As shown in FIGS. 30 and 23, FIG. 30 is a structural schematic view of a neck fan according to an embodiment of the present disclosure, and FIG. 31 is an exploded view of the neck fan shown in FIG. 30.

The bracket assembly 10 may include a first bracket 100, a second bracket 200 and a third bracket 300. The second bracket 200 may be connected to the first bracket 100 and the third bracket 300. Each of the first bracket 100, the second bracket 200 and the third bracket 300 may be a curved bracket. When the first bracket 100, the second bracket 200 and the third bracket 300 are connected, the three curved brackets may cooperatively form a ring-shaped body, such that the neck fan 01 may hang around the user's neck. The second bracket 200 may be disposed between the first bracket 100 and the third bracket 300, and may face a back of the user's neck. The first bracket 100 and the third bracket 300 are connected to two opposite ends of the second bracket 200 and face two opposite sides of user's neck. An opening may be defined between the first bracket 100 and the third bracket 300, allowing the bracket assembly 10 to sleeve the user's neck.

In some embodiments, the second bracket 200 may be arranged with a cooling sheet 203. While the user is wearing the neck fan 01, the cooling sheet 203 may attach to the back of the neck, such that the back of the neck may be cooled, providing a better user experience.

In some embodiments, two ends of the second bracket 200 may define a first slot 201 and a second slot 202, respectively. An end of the first bracket 100 is arranged with a first buckle 101, and an end of the third bracket 300 is arranged with a second buckle 301. When the second bracket 200 is connected to the first bracket 100 and the third bracket 300, the first buckle 201 may be fastened to the first slot 101, and the second buckle 301 is fastened to the second slot 202. In addition, at least one of the first buckle 101 and the second buckle 301 may be arranged with a rotation shaft, and at least one of a wall of the first slot 201 and a wall of the second slot 202 may define a corresponding shaft hole. In this way, the first bracket 100 is rotatably connected to the second bracket 200, and the third bracket 300 is rotatably connected to the second bracket 200. In this way, a distance between the first bracket 100 and the third bracket 300 bracket may be adjustable to accommodate various neck sizes of various users.

In the present embodiment, the neck fan 01 may include at least three wind turbines. Each of the first bracket 100, the second bracket 200, and the third bracket 300 bracket define an air duct, the air outlets 11 and the air inlets 12. One wind turbine is received in each of the air duct of the first bracket 100, the air duct of the second bracket 200, and the air duct of the third bracket 300. The wind turbine generates an air flow for each air duct.

In some embodiments, the first bracket 100, the second bracket 200 and the third bracket 300 may be made of metal or plastics.

In other embodiments, the bracket assembly 10 may include a fourth bracket or more brackets, and each bracket defines a respective air duct and receives a respective wind turbine. The present disclosure does not limit the number of the brackets.

Figure 32:
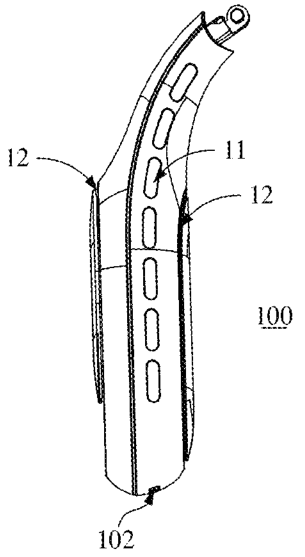
FIG. 32 is a structural schematic view of a first bracket of a neck fan according to an embodiment of the present disclosure.
Figure 33:
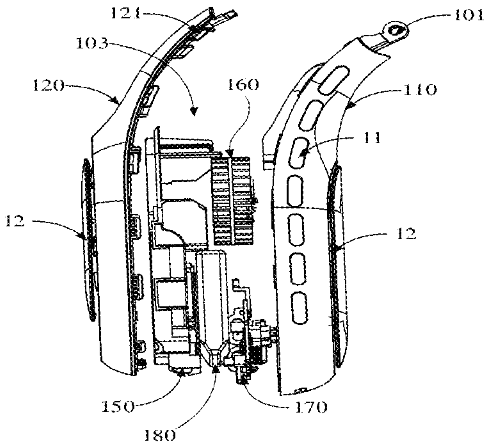
FIG. 33 is an exploded view of the first bracket and a wind turbine of the embodiment shown in FIG. 32.

As shown in FIGS. 32 and 33, FIG. 32 is a structural schematic view of a first bracket of a neck fan according to an embodiment of the present disclosure, and FIG. 33 is an exploded view of the first bracket and a wind turbine of the embodiment shown in FIG. 32.

An outer circumference of the first bracket 100 defines the plurality of air outlets 11. while the neck fan is being worn to the user, the plurality of air outlets 11 may face the user's face. The air inlets 12 are defined in two sides of the first bracket 100 and communicate with the air outlets 11. In some embodiments, the first bracket 100 may be arranged with a power supply interface 102. The power supply interface 102 may be configured to connect to a power source for charging the neck fan.

In detail, the first bracket 100 may include a first shell 110 and a second shell 120. The first shell 110 and the second shell 120 may be connected to cooperatively define a receiving slot 103. The wind turbine 160 may be received in receiving slot 103. That is, each of the first shell 110 and the second shell 120 is a shell having an opening. When connecting the two shells, the opening of the first shell 110 may align to and communicate with the opening of the second shell 120, such that the receiving slot 103 may be formed.

In some embodiments, a portion of the second shell 120 near the opening is arranged with a plurality of third buckles 121. The plurality of third buckles 121 may be arranged around a circumference of the opening of the second shell 120. A portion of the first shell 110 near the opening defines a plurality of third slots corresponding to the third buckles 121. When the first shell 110 and the second shell 120 are fastened, the plurality of third buckles 121 may be fastened with the plurality of third slots. In other embodiments, the first shell 110 may be connected to the second shell 120 by bonding, screwing, and the like.

In the present embodiment, each of the first shell 110 and the second shell 120 may be a curved shell. When the first shell 110 and the second shell 120 are fastened to each other, the first bracket may be well adapted to the user's neck. In other embodiments, the first shell 110 and the second shell 120 may be in other shapes, which will not be limited by the present disclosure.

Further, the neck fan may further include a battery 180 and a circuit board 170. The circuit board 170 may be electrically connected to the battery 180 and the wind turbine 160. The battery 180 may be a rechargeable battery. The battery 180 may be configured to store electrical energy and supply power to the wind turbine 160. The circuit board 170 may be configured to control a power of the wind turbine 160 and may further be arranged with a charging circuit for the battery 180.

In some embodiments, the first bracket 100 may further include a support frame 150. The support frame 150 may be fixedly arranged inside the first shell 110 or the second shell 120, and may be received in the receiving slot 103. The battery 180 and the circuit board 170 may be arranged inside the support frame 150.

The air inlets 12 may communicate with the receiving slot 103 and may be configured to allow the external air to be driven by the wind turbine 160 to flow into the receiving slot 103.

Each of the air inlets 12 may be a groove defined in the first shell 110 or the second shell 120. Alternatively, each of the air inlets 12 may be a through hole defined in the first shell 110 or the second shell 120.

Figure 34:
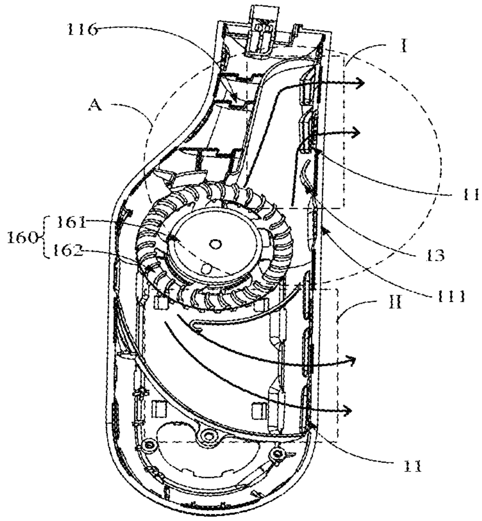
FIG. 34 illustrates an interior of the first bracket and the wind turbine of the embodiment shown in FIG. 33.

As shown in FIGS. 33 and 34, FIG. 34 illustrates an interior of the first bracket and the wind turbine of the embodiment shown in FIG. 33. In the present embodiment, arranging the air turbine 160 inside the first shell 110 and defining the air duct in the first shell 110 will be taken as an example to illustrate the neck fan. In other embodiments, the air turbine 160 and the air duct may also be arranged in the second shell 120. Arrows in the drawing indicate directions of the air flowing in the air duct.

In the present embodiment, the wind turbine 160 may include a bearing portion 161 and a fan portion 162 arranged around the bearing portion 161. The bearing portion 161 is fixedly arranged inside the first shell 110. The bearing portion 161 drives the fan portion 162 to rotate, generating the wind to flow to circumference of the fan portion 162. An electric motor may be arranged inside the bearing portion 161. The wind turbine 160 may drive the fan portion 162 to generate the wind by means of motor driving. The wind turbine 160 may rotate counterclockwise or clockwise.

In some embodiments, the first shell 110 may further define a wire slot 116 for receiving wires, such that circuit boards or wind turbines in other shells may be electrically connected.

In the present embodiment, the first shell 110 defines two air ducts, an air duct I and an air duct II. The air duct I and the air duct II locate on two opposite sides of the wind turbine 160. Since the fan portion 162 of the wind turbine 160 is able to generate the wind towards the circumference of the wind turbine 160, the wind turbine 160 is able to provide air flowing in various directions to the air duct I and the air duct II. In some embodiments, the first shell 110 may define three or more ducts therein.

A plurality of air outlets 11 may be defined. Each of the air duct I and the air duct II may communicate with a corresponding air outlet 11 to guide the air flowing in the air duct to the corresponding air outlet 11. In the present embodiment, an air flowing direction in the air duct I will be taken as an example to illustrate the present embodiment. Air flowing directions in other air ducts in the first bracket or air flowing directions in air ducts in other brackets may be referred to the following embodiment.

In the present embodiment, the air outlet 11 is defined in a first side wall 111 of the first shell 110. The first side wall 111 may be any of side walls of the first shell 110 configured to define the air duct I.

The wind turbine 160 is disposed adjacent to the first side wall 111. The wind turbine 160 provides air flowing to the air duct I. Further, an air flowing direction of the air, which is provided by the wind turbine 160, flowing in the air duct I is parallel to the first side wall 111. The plurality of air outlets 11 are distributed in the first side wall 111 and are spaced apart from each other along an extending direction of the first side wall 111. That is, the plurality of air outlets 11 are arranged on the first side wall 111 along the flowing direction of the air generated by the wind turbine 160.

In the art, the air generated by the wind turbine to the air duct may flow towards the extending direction of the first side wall. When the air flows past an air outlet near the wind turbine, the air may continue flowing, maintaining its original flowing direction, and this is because the air does not flow towards the air outlet. When the air flows to reach an end of the air duct, most of the air in the air duct may gather at the end, and an air pressure at the end of the air duct may increase. In this case, the air outlet at the end of the air duct may be impacted by the air significantly, and the air may generate resonance, producing the wind noise.

To solve the above technical problem, in the present disclosure, a wind guide member 13 may be arranged inside the first bracket 110. For example, the first bracket 110 defines the air duct, and the wind guide member 13 may be received in the air duct. When the air flows along the wind guide member 13, the Coanda Effect may be caused, and the original flowing direction of the air may be changed. In this way, the air may flow along a surface of the wind guide member 13, flowing towards the air outlet 11. For example, the wind guide member 13 may be disposed on a wall of the shell near the air outlet 11 or received in the air outlet 11. In this way, an air flowing intensity of the air outlet 11 may be increased, and an air flowing intensity of other outlets 11, which may be excessively large, may be reduced. In this way, the wind noise at the air outlet 11 which has the excessively large air flowing intensity may be reduced.

Figure 35:
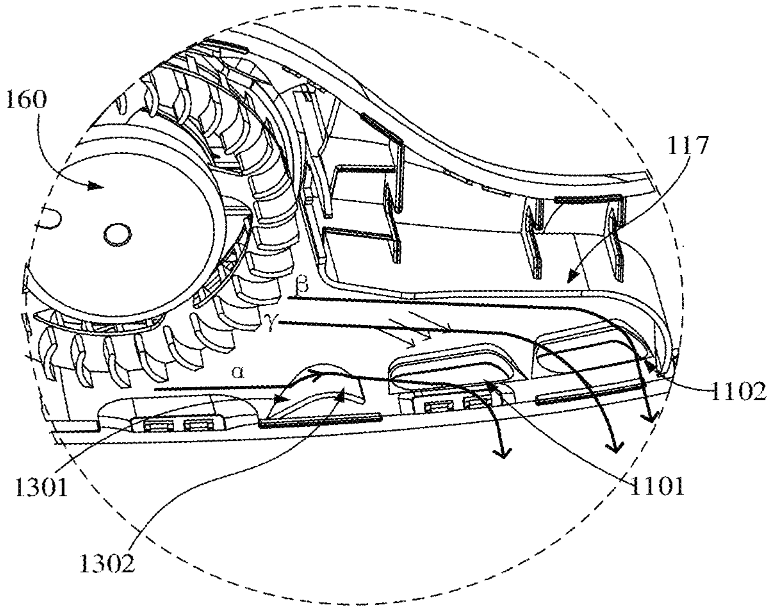
FIG. 35 is an enlarged view of a portion A of the embodiment shown in FIG. 34.

As shown in FIGS. 34 and 35, FIG. 35 is an enlarged view of a portion A of the embodiment shown in FIG. 34.

In the present embodiment, the air duct I may be communicated with at least two air outlets 11. The at least two air outlets 11 may include a first air outlet 1101 and a second air outlet 1102. The first bracket 100 may further include a wind guide plate 117, serving as another wind guide member. The wind guide plate 117 may be spaced apart from the wind guide member 13. For example, the wind guide plate 117 and the wind guide member 13 may be disposed at two sides of the air duct I. The wind guide plate 117 may be configured to direct the air generated by the wind turbine 160 to the first air outlet 1101 and the second air outlet 1102.

In some embodiments, the wind guide plate 117 may be a curved plate. An end of the wind guide plate 117 is connected to a shell wall that defines the first air outlet 1101. An end of the wind guide plate 13 is connected to a shell wall that defines the second air outlet 1102. When the air generated by the wind turbine 160 is flowing towards the wind guide plate 117, the air flowing direction may be affected by the wind guide plate 117, such that the air may flow towards the first air outlet 1101 and the second air outlet 1102.

In the present embodiment, the air flowing in the air duct I may include a first air flow α, a second air flow β and a third air flow γ. Curves and arrows in FIG. 35 indicate air flowing directions in the air duct. The first air flow α, the second air flow β and the third air flow γ are labeled for understanding the air flowing in various regions of the air duct. Actual air flows in the air duct I shall not be limited to the first air flow α, the second air flow β and the third air flow γ.

The first air flow α, the second air flow β and the third airflow γ may be parallel to each other.

The first air flow α is flowing near the wind guide member 13, and the second air flow β is flowing near the wind guide plate 117. The third air flow γ is flowing between the first air flow α and the second air flow β.

Since the second air flow β is flowing closest to the air guide 117, the second air flow β is easily affected by the wind guide plate 117, such that the second air flow β may flow out of the neck fan through the second air outlet 1102. When the wind guide member 13 is not arranged, the flowing direction of the first air flow α and the flowing direction of the third air flow γ do not change when passing the first air outlet 1101, but instead, the first air flow α and the third air flow γ continue flowing straightly towards the wind guide plate 117. This is because the first air flow α and the third air flow γ are distant from the wind guide plate 117. Only when the first air flow α and the third air flow γ encounter the wind guide plate 117, the flowing directions thereof may change, and the first air flow α and the third air flow γ may flow towards the second air outlet 1102. In this way, air flows in the second air outlet 1102 may include an air flow obtained by pressurizing the first air flow α, the second air flow β and the third air flow γ. The air flowing intensity in the second air outlet 1102 may be excessively large. An air flow that has an excessively large intensity may impact the second air outlet 1102, generating the wind noise and affecting the user experience.

In the present embodiment, the wind guide member 13 may be received in the air duct I. The wind guide member 13 may be disposed near the first air outlet 1101 and disposed on the first side wall 111. After flowing past the wind guide member 13, first air flow α may be affected by the wind guide member 13 to flow out of the neck fan through the first air outlet 1101. That is, the first air flow α does not flow out of the neck fan through the second air outlet 1102. In this way, the amount of air flowing through the second air outlet 1102 may be reduced, reducing the wind noise at the second air outlet 1102.

In detail, the wind guide member 13 may be a protrusion arranged on the first side wall 111 and protrudes towards the air duct I. The wind guide member 13 protruding from the first side wall 111 towards the air duct I allows the Coanda Effect to be caused while the first air flow α flowing past the protrusion. The wind guide member 13 may include a wind-ward portion 1301 and wind-guide portion 1302. The wind-ward portion 1301 may be connected to the wind-guide portion 1302. The wind-ward portion 1301 and the wind-guide portion 1302 may be fixedly arranged inside the first shell 110. The wind guide member 13 and the first shell 110 may be integrally arranged as one piece. Alternatively, the wind guide member 13 may be connected to the shell 110 by fastening or bonding.

The wind-ward portion 1301 may be opposite to the wind turbine 160. The first air flow α may flow directly towards the wind-ward portion 1301. The wind-guide portion 1302 is connected to the wind-ward portion 1301 to form a projection protruding towards the air duct I. That is, a certain angle is between the wind-guide portion 1302 and the wind-ward portion 1301. A face of a connected portion between the wind-guide portion 1302 and the wind-ward portion 1301 may be a convex face that has a certain curvature.

In some embodiments, the convex face of connected portion between the wind-guide portion 1302 and the wind-ward portion 1301 may be a curved face, a spherical face, or a cylindrical face.

When the first air flow α flows directly towards the wind-ward portion 1301, a surface friction may be generated between the first air flow α and the wind-ward portion 1301, an original flowing direction of the first air flow α may change, and the first air flow α may flow along surfaces of the wind-ward portion 1301 and the wind-guide portion 1302. The wind-guide portion 1302 is connected the wall of the shell that defines the first air outlet 1101. In this way, the first air flow α flows along the wind-guide portion 1302 to the first air outlet 1101, reducing the amount of the air flowing through the second air outlet 1102.

Since the first air flow α flows through the first air outlet 1101, an air pressure of a gap between the first air outlet 1101 and the second air flow β may be reduced. Therefore, the third air flow γ may flow towards the first air flow α to fill a space where the first air flow α originally flows. The third air flow γ may be affected by the wind-guide portion 1302 and may be appropriately shifted towards the first air flow α.

Similarly, the second air flow β may also be affected by the wind-guide portion 1302 and shifted towards the first air flow α. A portion of the second air flow β or the third air flow γ may be affected by the first air flow α shifting to shift towards the first air flow α, and may flow out of the neck fan through the second air outlet 1102. Another portion of the second air flow β or third air flow γ may be affected by the wind guide plate 117, the air flowing directions thereof may change, and the another portion of the second air flow β or third air flow γ may flow out of the neck fan through the second air outlet 1102. Therefore, the second air flow β and the third air flow γ in the present embodiment do not completely rush to the wind guide plate 117, changing flowing directions only after encountering the wind guide plate 117, but may shift towards the first side wall 111 since the first air flow α shifts. Compared to the neck fan in the art, noise generated by the air flow hitting the wind guide plate 117 may be reduced in the present embodiment.

Therefore, in the present embodiment, the wind guide member 13 may reduce the wind noise generated by the air flowing through the second air outlet 1102 by reducing the air flowing intensity near the second air outlet 1102. Further, the wind guide member 13 allows the air flowing direction at the second air outlet 1102 to be changed, such that the air may flow towards the second air outlet 1102 directly, instead of flowing out of the second air outlet 1102 only after rushing at and being cut by the second air outlet 1102.

Further, in the present embodiment, the wind guide member 13 reduces the wind noise generated by the neck fan, and further increases the amount of air flowing through the air outlet 11, which is an air outlet for a weak air flow. In this way, the amount of air flowing through each of the plurality of air outlets may be uniform.

When the wind guide member 13 is not arranged, the first air outlet 1101 is defined in the first side wall 111. The first side wall 111 is relatively parallel to the first air flow α. In this way, the first air flow α would not flow out through the first air outlet 1101 when passing the first air outlet 1101. Therefore, the air flowing intensity at the first air outlet 1101 may be weaker, and the air flowing intensity at other air outlets 11 may be excessively strong.

In the present embodiment, the first side wall 111 is arranged with the wind guide portion 13. The wind guide portion 13 may be closer to the wind turbine 160 compared to the first air outlet 1101. When the first air flow α flowing against the wind-ward portion 1301 of the wind guide member 13, the surface friction may be generated between the first air flow α and the wind-ward portion 1301, the air flowing direction of the first air flow α may change accordingly, and the first air flow α may flow along the surface of the wind-ward portion 1301 and the wind-guide portion 1302. The wind-guide portion 1302 is connected to the shell wall that defines the first air outlet 1101. At last, the first air flow α may flow along the wind-guide portion 1302 towards the first air outlet 110, increasing the amount of the air flowing at the first air outlet 1101.

In some embodiments, the air guide member 13 may further be arranged at the shell wall that defines other air outlets 11 to increase the air flowing intensities at corresponding air outlets 11.

According to the present embodiment, the wind guide member 13 may be arranged inside the first bracket 100 to change the flowing directions of the air in the air duct, and may be configured to direct air flows to corresponding air outlets 11. In this way, a problem of various air flowing efficiencies at various air outlets 11 may be solved, the wind noise at the air outlet 11 may be reduced, and the air flowing through each of the plurality of air outlets 11 may be uniform. User's experience may be improved, and a structure of the neck fan may be simple, such that the neck fan may be easily prepared.

Figure 36:
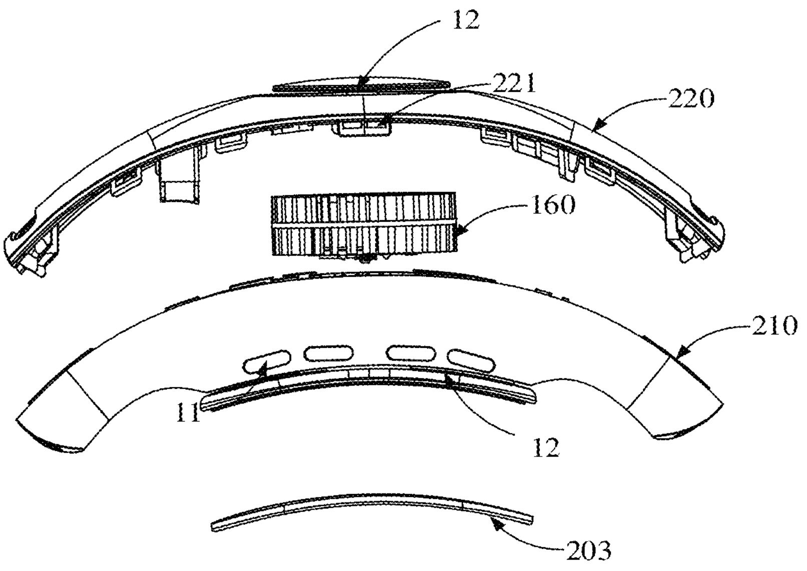
FIG. 36 is an exploded view of a second bracket and a wind turbine of a neck fan according to an embodiment of the present disclosure.

As shown in FIG. 36, FIG. 36 is an exploded view of a second bracket and a wind turbine of a neck fan according to an embodiment of the present disclosure.

The second bracket may include a third shell 210, a fourth shell 220, a wind turbine 160, and a cooling sheet 203. The third shell 210 may be fastened to the fourth shell 220. The air duct may be defined in the third shell 210 and the fourth shell 220. The wind turbine 160 may be received in the third shell 210 and the fourth shell 220. The cooling sheet 203 may be connected to the third shell 210 and configured to contact the back of the user's neck.

Each of two ends of the third shell 210 and two ends of the fourth shell 220 may define the air inlet 12. The third shell 210 may define the plurality of air outlets 11 communicating with the air duct. An inner side of the third shell 210 and the fourth shell 220 may further define the air inlet 12 communicating with the air duct. The wind turbine 160 may provide the air flowing to the air duct, and the air may further flow out of the fan through the air outlets 11. The air outlets 11 may be defined in the fourth shell 220.

Arrangement of the third shell 210, the fourth shell 220, and the wind turbine 160 may be referred to the arrangement for the first bracket as illustrated in the above, and will not be repeatedly described herein.

Figure 37:
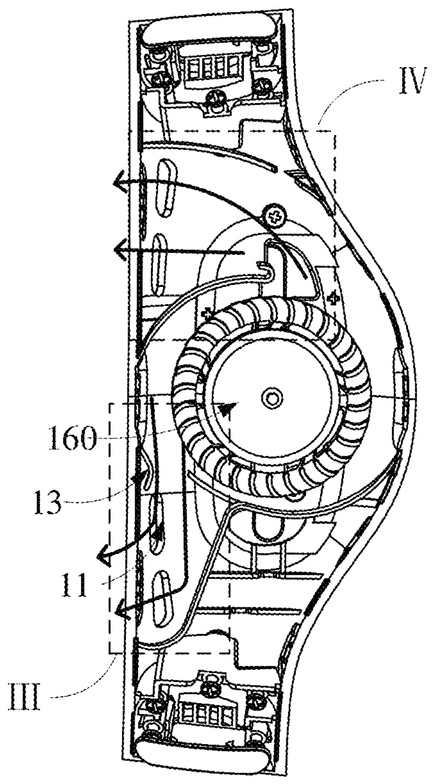
FIG. 37 illustrates an interior of a third shell of the embodiment shown in FIG. 36.

As shown in FIGS. 36 and 37, FIG. 37 illustrates an interior of a third shell of the embodiment shown in FIG. 36. Curves and arrows in FIG. 37 indicate air flowing directions in the air duct.

In the present embodiment, the air duct may be defined in the third shell 210, and the wind tuberin 160 may be arranged inside the third shell 210. The air duct in the third shell 210 may include an air duct III and a fourth air duct IV. The third air duct III and the fourth air duct IV may be defined at two opposite sides of the wind turbine 160. The air flows provided by the wind turbine to the air duct III and the air duct IV may flow along different directions. The air duct III and the air duct IV may communicate to corresponding air outlets 11.

In the present embodiment, the wind guide member 13 is arranged near the air outlet 11 that communicates with the air duct III. The wind flowing in the air duct III may be affected by the wind guide member 13 when flowing past the wind guide member 13, causing the Coanda Effect, such that the air may flow out of the fan through the air outlet 11, an air flowing intensity at the air outlet 11 may be increased, and an air flowing intensity and wind noise at other air outlets may be reduced.

Structures of the air duct and the wind guide member 13 in the third shell 210 may be similar to those of the first bracket, and may be referred to the above embodiments.

Therefore, in the present embodiment, the wind guide member 13 may be arranged inside the third shell 210, a problem of various air outlets having various air flowing efficiencies may be solved, and the wind noise at the air outlets may be reduced.

A structure of the third bracket may be similar to that of the first bracket, i.e., the wind guide member may be arranged in the third bracket. Therefore, the structure of the third bracket will not be repeatedly described herein.

According to the present embodiment, the wind guide member may be received in the air duct for guiding the air to flow to corresponding air outlets. The air flowing direction may be changed and may be directed to various air outlets. The wind noise caused by air rushing may be reduced. The air outlet, which has an excessively low air pressure in the art, may now have an increased air pressure, and the air outlet, which has an excessively high air pressure in the art, may now have a reduced air pressure. The problem of various air outlets having various air flowing efficiencies may be solved.

FIGS. 38-44 shows a neck fan according to another embodiment of the present disclosure.

An arrow X in the figures indicate a front-rear direction, i.e., a radial direction. An arrow Y in the figures indicate a horizontal direction, i.e., a left-right direction. An arrow Z in the figures indicate a vertical direction, i.e., an up-down direction.

Figure 38:
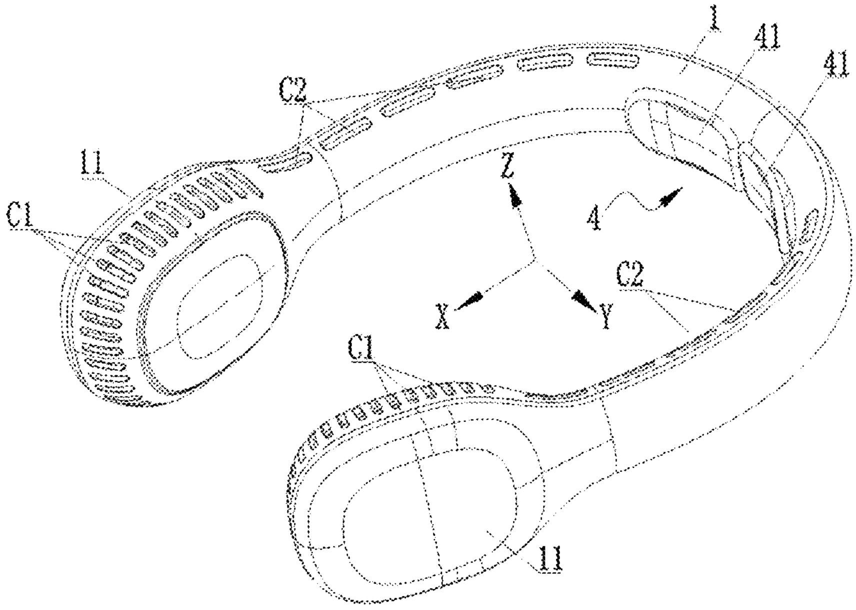
FIG. 38 is a schematic view of a neck fan according to an embodiment of the present disclosure.
Figure 39:
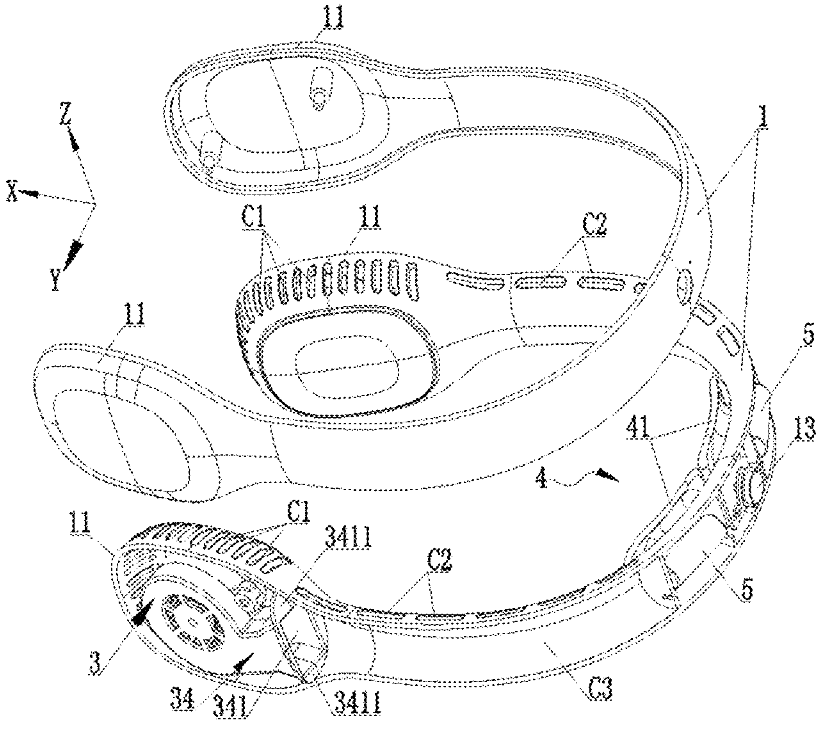
FIG. 39 is an exploded view of the neck fan shown in FIG. 38.
Figure 40:
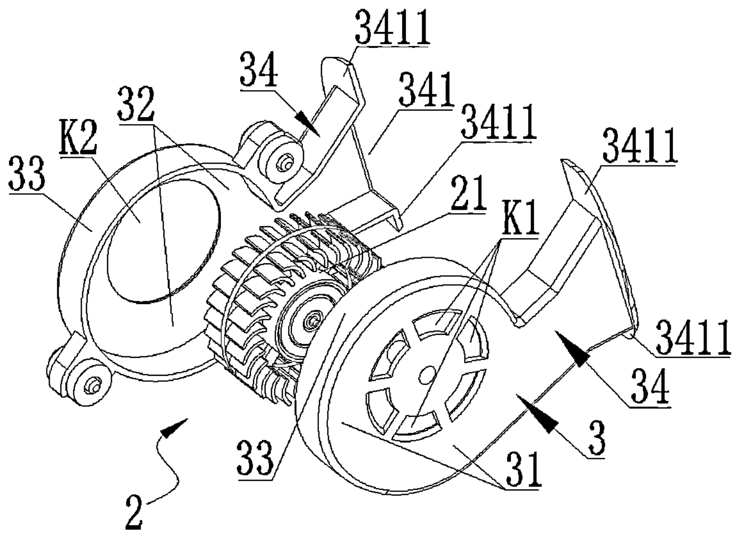
FIG. 40 is an exploded view of connection between an inner shell and a fan assembly of a neck fan according to another embodiment of the present disclosure.

As shown in FIGS. 38-40, the neck fan 1 may include a shell 1, a fan assembly 2, and an inner shell 3. The shell 1 may be configured to hang around the user's neck. The shell 1 may define an air inlet C1, an air outlet C2, and an air duct C3 between the air inlet C1 and the air outlet C2. The fan assembly 2 may be configured to guide the external air into the neck fan through the air inlet C1, and guide the air to flow through the air duct C3 to reach the air outlet C2. The inner shell 3 may be arranged inside the shell 1. The fan assembly 2 may be received in an inner space of the inner shell 3. The inner space of the inner shell 3 may communicate with the air inlet C1 and the air duct C3. The inner shell 3 may protect the fan assembly 2, preventing the fan assembly 2 from being damaged caused by being crushed by external forces. Further, the inner shell 3 may prevent the user's hair from entering the air inlet C1 to reach the fan assembly 2. In this way, the inner shell 3 prevents the hair from winding turning blades of the fan assembly, protecting the user.

In some embodiments, the fan assembly 2 may be a turbine fan. Two opposite sides of the turbine fan may be arranged with a first air inlet window 21 and a second air inlet window respectively. The two air windows are independent from each other, allowing the fan assembly to intake the air/wind from two opposite sides, such that the amount of air intaking may be increased, a wind stifling effect may not be caused, and the wind nose may be reduced. A position of the inner shell 3 corresponding to the first air inlet window 21 may be define a first inner air inlet K1, and a position of the inner shell 3 corresponding to the second air inlet window may be define a second inner air inlet K2. In this way, after the air enters the first inner air inlet K1 and the second inner air inlet K2, the air may quickly enter the first air inlet window 21 and the second air inlet window respectively. Further, fan blades of the turbine fan may drive the air to flow to air duct to reach the air outlet C2, such that the air may flow out of the neck fan. In this way, a contact speed between the air and the turbine fan may be increased, increasing the air flowing efficiency, ensuring the amount of air entering the fan, and increasing an efficiency of taking the air in the inner shell 3 to flow through. Further, a distance that the air flows to reach the fan assembly 2 may be reduced, noise generated by air flowing may be reduced effectively, that is, the wind noise may be reduced.

In some embodiments, the shell 1 may define a receiving chamber 11 for receiving the inner shell 3. In detail, the receiving chamber 11 may be defined in an end portion of the shell 1. A side wall of the receiving chamber 11 may include at least one air inlet region. The air inlet C1 is defined in the air inlet region. The air inlet C1 may communicate with the first inner air inlet K1 and the second inner air inlet K2. In this way, the air in the shell 1 may flow into the first inner air inlet K1 and the second inner air inlet K2.

In some embodiments, the inner shell 3 may include a first axial shell portion 31, a second axial shell portion 32, a radial shell portion 33. The first air inlet window 21 is arranged with the first axial shell portion 31. The second air inlet window is arranged with the second axial shell portion 32. The radial shell portion 33 is arranged along a radial direction of a rotation shaft of a fan of the turbine fan. The at least one air inlet region may be spaced apart from the radial shell portion 33. Further, the at least one air inlet region may be disposed away from the first inner air inlet K1 and the second inner air inlet K2. In this way, the hair may be prevented from entering the air inlet C1 to further reach an inside of the inner shell 3, such that the hair may be prevented from winding the fan assembly 2. Therefore, in the present embodiment, hair stranding caused by the hair reaching the inside of the inner shell may be avoided, protecting the user. In addition, in the present embodiment, the air that enters the neck fan through the air inlet C1 may not be completely compressed into the first inner air inlet K1 and the second inner air inlet K2. Since at least one air inlet region is away from the first inner air inlet K1 and the second inner air inlet K2, the air may be separated to the first inner air inlet K1 and the second inner air inlet K2 respectively, preventing air compression. Therefore, the wind may not be squeezed, and the wind noise may be reduced.

Figure 41:
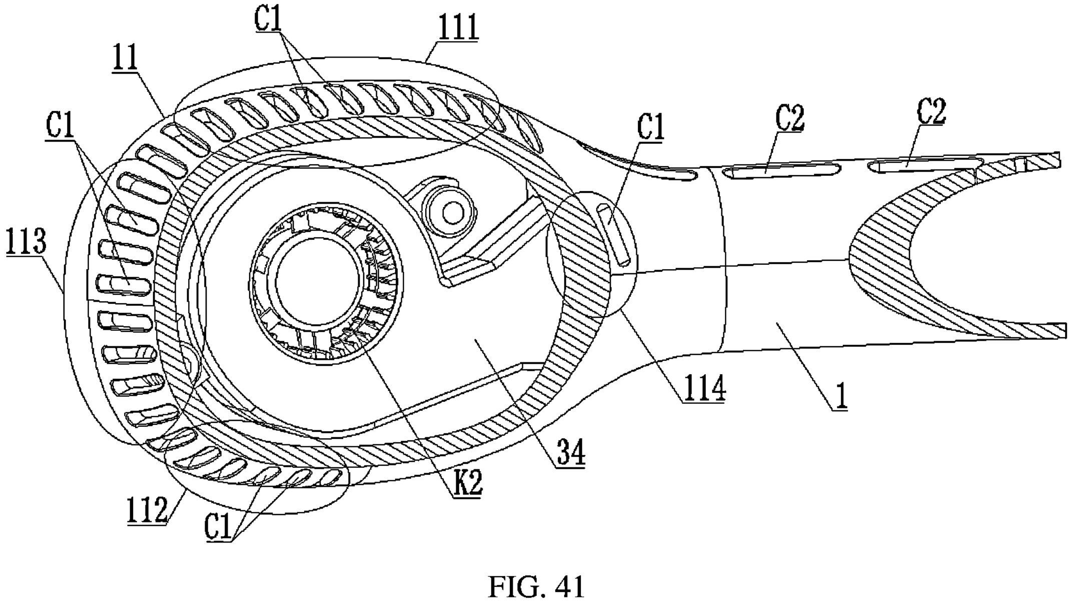
FIG. 41 is a cross section view of an end portion of an outer shell of a neck fan according to another embodiment of the present disclosure.

In some embodiments, as shown in FIG. 41, the shell 1 is configured to hang around the user's neck. The at least one air inlet region may include an upper air inlet region 111, a lower air inlet region 112, and/or an end air inlet region 113. The upper air inlet region 111 may operate cooperatively with the lower air inlet region 112 or the end air inlet region 113 to increase the amount of air inlet. Arranging the lower air inlet region 112 and the end air inlet region 113 allows the air inlets to be defined away from the user, such that the wind noise may propagate away from the user, reducing the wind noise. Further, positions where the lower air inlet region 112 and the end air inlet region 113 are arranged prevents the user's hair from entering the fan assembly 2 and winding the fan blades while the neck fan is worn to the user, ensuring the user's safety. In some embodiments, only the lower air inlet region 112 may be arranged. Since the air inlet defined in the lower air inlet region facing downwards, preventing the hair or other foreign matters from entering the air inlet due to the gravity. In some embodiments, only the end air inlet region 113 may be arranged. Since the air inlet defined in the end air inlet region 113 faces away from the user, noise of a fan motor or noise generated by the wind hitting a wall of the air duct may propagate through the air inlet of the end air inlet region 113, propagating away from the user, reducing the wind noise significantly. In some embodiments, only the lower air inlet region 112 and the end air inlet region 113 are arranged, ensuring the amount of air intaking to be adaptive to any fan in any power. A sufficient number of air ducts are defined, and a sufficient amount of air is taken in. Any combination of the upper air inlet region 111, the lower air inlet region 112, and the end air inlet region 113 may be arranged, as long as an application scenario can be satisfied.

In some embodiments, the external air may flow through the air inlet C1 of the air inlet region along a first air inlet direction. After the air reaches the receiving chamber 11 by flowing through the air inlet C1, the air may flow through the first inner air inlet K1 or the second inner air inlet K2 along a second air inlet direction. An angle between the first air inlet direction and the second air inlet direction may be in a range of 0° to 90°. In some embodiments, the angle between the first air inlet direction and the second air inlet direction may be in a range of 85°-90°. In some embodiments, the angle between the first air inlet direction and the second air inlet direction may be 90°. In this way, the fan assembly 2 intaking the external air and driving the air to flow from the air inlets to the air outlets may generate two different air inlet directions. The two air inlet directions may be perpendicular to each other. In this way, even if the hair enters the shell 1 along the first air inlet direction, the hair may not be able to enter the inner shell 3 along the second air inlet direction. Therefore, the hair may not wind the fan assembly 2, preventing hair stranding. Further, the first air inlet direction may be substantially perpendicular to the second air inlet direction, allowing fan blades of the fan assembly 2 to be blocked, such that the external dust or water may not enter the fan assembly 2, protecting the fan assembly 2.

In some embodiments, as shown in FIGS. 40 and 41, the inner shell 3 may further include a wind guide portion 34. The wind guide portion 32 may define a wind guide opening 341. The wind guide opening 341 may communicate with the first inner air inlet K1 and the second inner air inlet K2. In the present embodiment, the air inlet C1 is defined closely near the wind guide portion 34 and away from the fan assembly 2. As shown in FIG. 41, a rear air inlet region 114 is arranged, and the above mentioned air inlet C1 is defined in the rear air inlet region 114. In the present embodiment, the air inlet C1 may increase the amount of air inlet and increase an air intaking area, allowing the air that enters the shell 1 may be distributed inside the shell 1 more evenly, preventing the wind from being squeezed, and reducing the wind noise.

In some embodiments, as shown in FIGS. 38-42, an edge of the wind guide opening 341 may be bent outwardly and abut against an inner wall of the shell 1, such that a gap between the edge of the wind guide opening 341 and the inner wall of the shell 1 may be sealed. In this way, the air flowing out of the wind guide opening 341 may be prevented from flowing to the gap between the edge of the wind guide opening 341 and the inner wall of the shell 1. It shall be understood that, when the air flowing to the gap, the air may no flow along the air duct C3. By sealing the gap, the wind noise generated by disordered air circulation may be reduced, and the air flowing out of the wind guide opening 341 may be completely flow along the air duct C3, ensuring the total amount of air flowing for generating the wind, and improving an air flowing efficiency.

In some embodiments, a diameter of the wind guide opening 341 may gradually increase along a direction facing the air duct C3. Increasing the diameter allows the air to be separated, preventing the wind from being squeezed, and reducing the wind noise. Further, the air flowing diameter is increased, increasing the amount of air reaching the air duct C3, and increasing the amount of wind flowing out of the neck fan, improving the user's experience.

In some embodiments, at least three sets of the inner shell 3 and the fan assembly 2 may be arranged. One set of the inner shell 3 and the fan assembly 2 may be arranged at each of a first end portion of the shell 1, a second end portion of the shell 1, and a connection portion between the first end portion and the second end portion. The connection portion may be disposed at a middle of the shell 1. Arranging a plurality of fan assemblies 2 and the inner shells 3 may increase an area covered by the wind flowing out of the neck fan, improving the user's experience.

Figure 42:
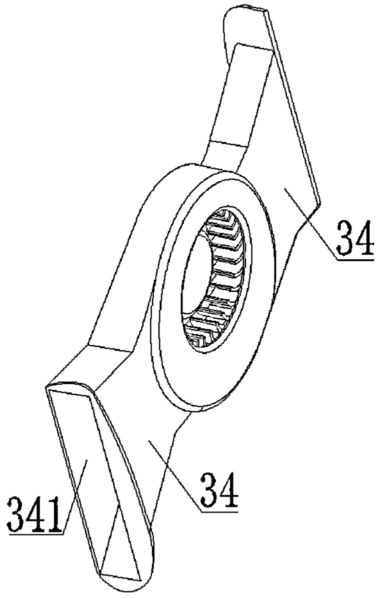
FIG. 42 is a schematic view of an inner shell of a neck fan according to another embodiment of the present disclosure.

In some embodiments, as shown in FIG. 42, two wind guide portions 34 may be arranged. The two wind guide portions 34 may guide the air to flow towards two opposite directions. In detail, a wind guide direction of the wind guide opening 341 of one of the two wind guide portions 34 may be opposite to a wind guide direction of the wind guide opening 341 of the other one of the two wind guide portions 34. For example, in the embodiment where two wind guide portions 34 are arranged, the fan assembly 2 may be arranged on the connection portion between the first end portion and the second end portion. In this way, arranging one fan assembly 2 may guide air towards the first end portion and the second end portion at the same time. In some embodiments, the fan assembly 2 may be arranged on one of the first end portion and the second end portion. The fan assembly may be arranged at a middle of the first end portion and guide the air to flow towards two ends of the first end portion.

In some embodiments, an inner middle portion of the first shell 1 may be arranged with an attaching portion 4 for attaching the user's neck. Arranging the attaching portion 4 allows the shell 1 to attach to the user's neck optimally. On one hand, the user may have a better hanging feeling. On the other hand, the shell 1 may be tightly attached to the user's neck, such that the neck fan may not fall off easily.

In some embodiments, the attaching portion 4 may include two attaching pads 41. Each of the two attaching pads 41 may be curved to fit with a curved shape of the user's neck. In this way, the curved shape of the pads may attach to the user's neck better, allowing the neck fan to hang to the neck more fixedly and stably.

In some embodiments, each of the two attaching pads 41 may be connected to the shell 1 through an elastic movable member. The elastic movable member may adjust the attaching pad 41 adaptively when the user is moving or when the user's neck is turning, such that the two attaching pads may attach to the user's neck at all times, allowing the neck fan to tightly attach to the user's neck, preventing the neck fan from falling off when the user is moving. In addition, when the user is moving, the elastic movable member prevents the attaching portion 4 from rubbing the user's neck, protecting the user's neck.

In some embodiments, the elastic movable member may be a spring and/or an elastic roller. The spring may provide a cushioning effect, allowing the attaching pads 41 to follow the user's neck in a movable manner. The elastic rolling may provide a rolling and sliding effect, allowing the attaching pads 41 to slide for a relatively short distance, such that the user's neck may not be rubbed easily. Further, the elastic rolling may be elastic, and therefore, the attaching pads 41 may follow the user's neck in the movable manner and may elastically slide for a tiny distance. In this way, the neck fan may be prevented from falling off from the user's neck, ensuring tight attachment between the neck fan and the user's neck. Further, the attaching pads 41 may not rub the user's neck, improving the user's experience.

In some embodiments, the attaching pads 41 may be made of soft and/or elastic material, preventing from rubbing the user's neck, and a relative moving between the user's neck and the attaching pads 41 may be buffered.

In some embodiments, the fan assembly 2 may include fan blades and a motor for driving the fan blades to rotate. Adjusting a rotating speed of the motor may control a rotating speed of the fan blades. In this way, an air flowing intensity and an amount of air flowing may be adjusted.

In some embodiments, the shell 1 may be curved and tubular and may be adapted to a shape of the user's neck. Electronic elements may be arranged in the shell 1, such as a circuit board, a battery, various modules, and the like.

In some embodiments, the air outlet C2 may be defined in an inner side and/or an upper face of the shell 1. In some embodiments, when the neck fan hangs around the user's neck, the inner side of the shell 1 faces the user's neck. Defining the air outlet C2 in the inner side allows the air to flow towards the neck directly, improving the user's experience optimally. The upper face of the shell 1 may face an upper portion of the neck, the user's face, and the user's head. Therefore, defining the air outlet C2 in the upper face allows the air to flow towards the above-mentioned portions of the user, and the air may flow to cover a large area of the user, improving the user's experience.

In some embodiments, at least one inner shell 3 is arranged at the end portion of the shell 1. Arranging the inner shell 3 at the end portion of the shell 1 may increase a weight of the end portion of the shell 1. In this way, when wearing the neck fan, a larger weight of the end portion of the shell 1 allows a gravitational center of the neck fan to be in a front portion of the neck fan. That is, the neck fan may be pendant to a front of the user, preventing the neck fan from fall off from a back of the user's neck. Therefore, arranging the inner shell 3 at the end portion of the shell 1 allows the neck fan to be stably worn to the user's neck.

In some embodiments, a battery 5 is arranged at an inner middle of the shell 1. The shell 1 is further arranged with a switch 13. The battery may supply power for the fan assembly 2, and the switch 13 may control the fan assembly to operate or stop operating.

Figure 43:
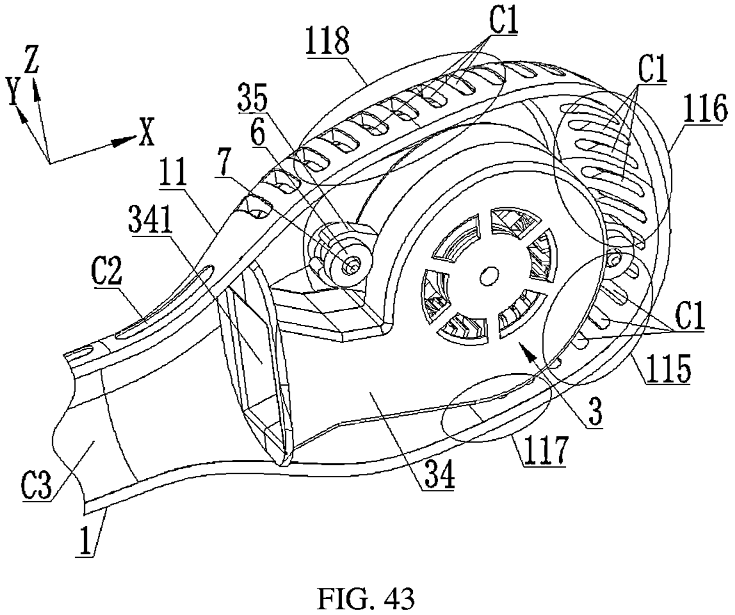
FIG. 43 illustrate an interior of an outer shell of a neck fan according to another embodiment of the present disclosure.
Figure 44:
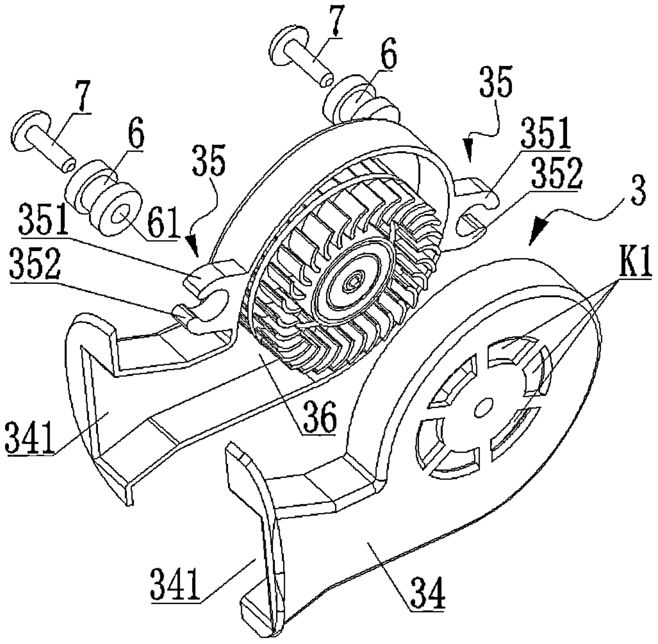
FIG. 44 is an exploded view of connection among an inner shell, a fan assembly, and a shaking absorption member of a neck fan according to another embodiment of the present disclosure.

As shown in FIGS. 43 and 44, in some embodiments, the neck fan may include the shell 1, the fan assembly 2, the inner shell 3 and a shaking absorption member 6. The shell 1 may hang around the user's neck. The shell 1 may define the air inlet C1, the air outlet C2, and an air duct C3 between the air inlet C1 and the air outlet C2. The air duct C3 may be configured for allowing air flowing. The fan assembly 2 may be configured to guide the external air into the neck fan through the air inlet C1, and guide the air to flow through the air duct C3 to reach the air outlet C2. The inner shell 3 may be arranged inside the shell 1. The fan assembly 2 may be received in the inner space of the inner shell 3. The inner space of the inner shell 3 may communicate with the air inlet C1 and the air duct C3. The shaking absorption member 6 may be arranged inside the shell 1 and configured to connect the inner shell 3 to the shell 1 for reducing shaking. In the present embodiment, arranging the shaking absorption member 6 prevents a direct contact between the inner shell 3 and the shell 1. That is, vibration may not be transmitted to the user's body, improving the user's experience. Further, since the inner shell and the shell do not directly contact each other, wear and tear between the inner shell and the shell may be eliminated, extending a service life of the shell 1 and the inner shell 3.

A clamping portion 35 may be arranged on the inner shell 3 for clamping the shaking absorption member 6. The shaking absorption member 6 may be connected to the shell 1 through a connection member 7. The clamping portion 35 may fix the shaking absorption member 6 and clamp the shaking absorption member 6. Therefore, the clamping portion 35 and the shaking absorption member 6 may be detachably connected, instead of being integrally formed as one piece. In this way, the shaking absorption member 6 may be replaced easily when being worn out or damaged.

In some embodiments, the shaking absorption member 6 may define a connection hole 61 for receiving the connection member 7. An end of the connection member 7 may be connected to the inner wall of the shell 1, ensuring the connection member 7 to fix the shaking absorption member 6.

In some embodiments, the shaking absorption member 6 may be a cylindrical elastic member, such that, the shaking absorption member 6 may be stably clamped by the clamping portion 35. The connection member 7 may be rod-shaped, such that the connection member 7 may easily inserted into the shaking absorption member 6.

In some embodiments, the shaking absorption member 6 may be made of silicon. Rigidity and softness of the shaking absorption member 6 may be appropriate for reducing shaking, such that shaking absorption may be achieved.

In some embodiments, the clamping portion 35 may include a first clamping arm 351 and a second clamping arm 352, and the first clamping arm 351 and the second clamping arm 352 may extend to gradually approach to each other. The first clamping arm 351 and the second clamping arm 352 may be arranged on a surface of the inner shell 3. The first clamping arm 351 and the second clamping arm 352 gradually approaching to each other may allow a clamping force to increase gradually, ensuring the clamping portion 35 to fixedly clamp the shaking absorption member 6, preventing the shaking absorption member 6 from falling off from the clamping portion 35.

In some embodiments, the end portion of the shell 1 may define the receiving chamber 11 for receiving the inner shell 3. The receiving chamber 11 may be ellipsoid. A plurality of air inlets C1 may be defined in a radial face of the receiving chamber 11. Defining the plurality of air inlets C1 in the radial face of the receiving chamber 11 may prevent the first inner air inlet K1 to from corresponding to the second inner air inlet K2. In this way, when the hair enters the air inlet C1, the hair may be prevented from entering the first inner air inlet K1 and the second inner air inlet K2 to further contact the fan assembly 2, preventing hair stranding. Therefore, user's safety may be ensured.

In some embodiments, the radial face of the receiving chamber 11 has an air inlet region. The air inlet C1 is defined in the air inlet region. The air inlet region includes a first air inlet region 115, a second air inlet region 116, a third air inlet region 117 and a fourth air inlet region 118. The first air inlet region 115 is located below a front side of the receiving chamber 11. The second air inlet region 116 is located at the front side of the receiving chamber 11. The third air inlet region 117 is located at a lower side of the receiving chamber 11. The fourth air inlet region 118 is located at an upper side of the receiving chamber 11. The above-mentioned plurality of air inlet regions cooperate with each other to increase the amount of air intaking, increase the amount of air flowing, and improving the user's experience. Arranging the first air inlet region 115 and the second air inlet region 116 as described in the above allows the air inlets to be far away from the user, allowing generated noise to propagate away from the user, reducing the wind noise. Positions at which the first air inlet region 115, the second air inlet region 116 and the third air inlet region 117 are arranged prevents the hair from being sucked into the fan blades of the fan assembly 2, such that hair stranding may be prevented, ensuring the user's safety.

In some embodiments, the inner shell 3 may include a receiving portion 36 and the wind guide portion 34 connected to the receiving portion 36. The receiving portion 36 is configured to receive the fan assembly 2. The receiving portion 36 defines an air inlet window for intaking the air. A structure of the air inlet window of the receiving portion 36 is similar to that of the first inner air inlet K1 and the second inner air inlet K2 as described above and will not be repeated here. The wind guide portion 34 may define the wind guide opening 341. The wind guide opening 341 extends and faces towards the air duct C3. The receiving portion 36 protects the fan assembly 2 from being affected by the external rain or dust. Further, if the hair enters from the air inlet C1, the receiving portion 36 prevents the entered hair from further entering the inner shell 3 to be stranded by the fan assembly 2, ensuring the user's safety.

In some embodiments, the edge of the wind guide opening 341 may be turned outwardly to abut against the inner wall of the shell 1 to seal the gap between the edge of the wind guide opening 341 and the inner wall of the shell 1. Details may be referred to the above embodiments, and will not be repeatedly described herein.

According to the present embodiment, the neck fan may include a shell, a fan assembly and an inner shell. The shell is configured to hang around the user's neck. The shell defines the air inlet, the air outlet and the air duct between the air inlet and the air outlet. The fan assembly is configured to drive the external air to flow through the air inlet and to guide the air to flow to the air outlet through the air duct. The inner shell is arranged inside the shell, and the fan assembly is arranged inside the inner shell. An inner space of the inner shell is communicated to the air inlet and the air duct. The neck fan is able to intake the air from a large area and blow out the air to a large area. Further, hair stranding caused by the hair entering the shell may be prevented, ensuring the user's safety.

Figure 45:
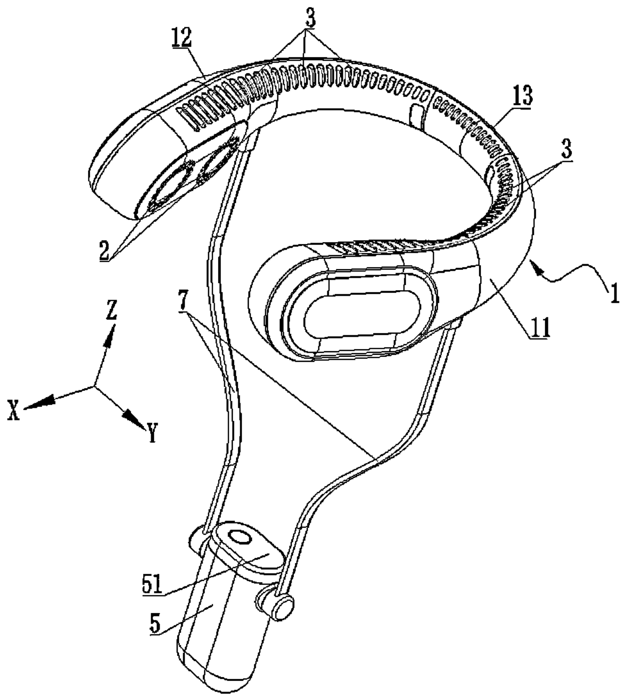
FIG. 45 is a schematic view of a neck fan according to an embodiment of the present disclosure.
Figure 46:
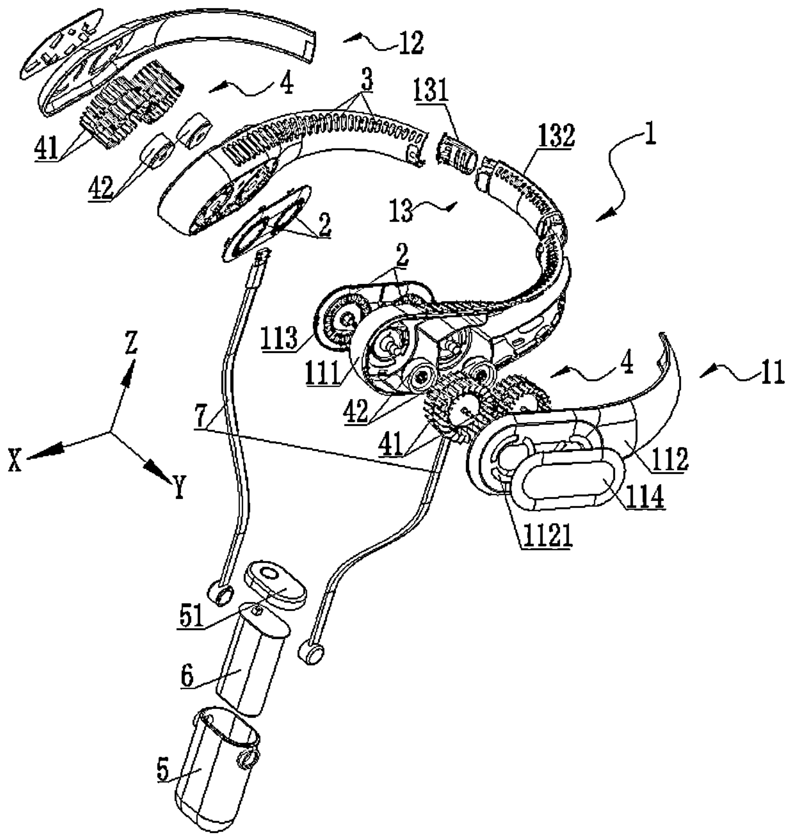
FIG. 46 is an exploded view of the neck fan shown in FIG. 45.
Figure 47:
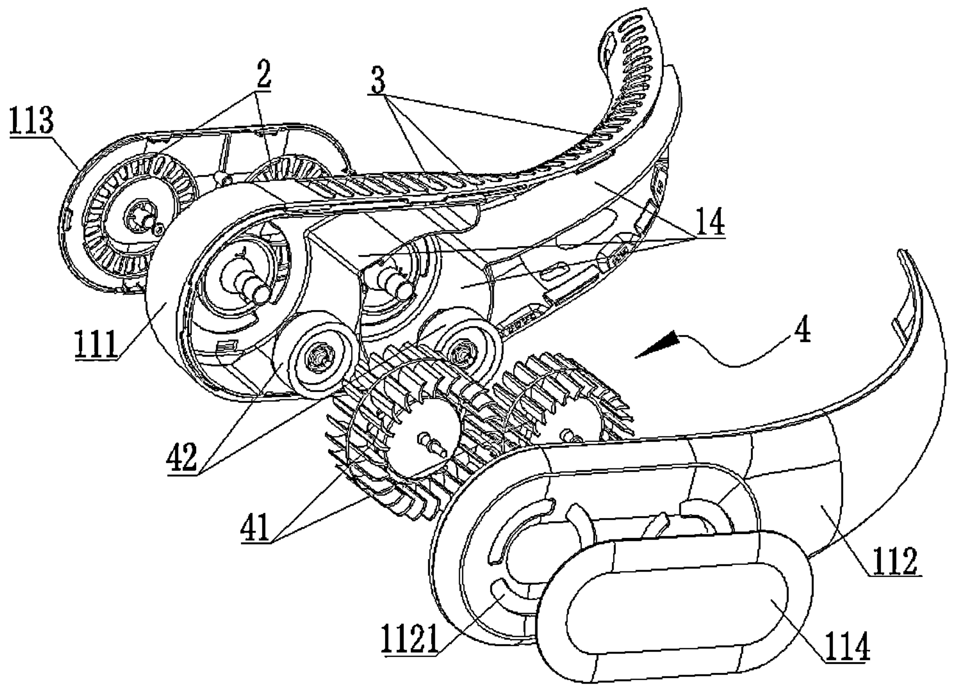
FIG. 47 is an exploded view of a left head portion of a neck fan according to another embodiment of the present disclosure.

FIGS. 45-47 show a neck fan according to another embodiment of the present disclosure.

An arrow X in the figures indicate a front-rear direction. An arrow Y in the figures indicate a horizontal direction, i.e., a left-right direction. An arrow Z in the figures indicate a vertical direction, i.e., an up-down direction.

As shown in FIGS. 45 and 46, the neck fan may include following components.

The shell 1 is configured to hand around the user's neck. The shell 1 defines an air inlet 2 and an air outlet 3. The air inlet 2 is defined to allow the external air to flow into the neck fan. The air outlet 3 is defined to allowing the air to flow out of the neck fan.

A fan assembly 4 is arranged to drive the external air to enter the neck fan through the air inlet 2 and to drive the air to flow out of the neck fan through the air outlet 3. The fan assembly 4 is arranged inside the shell 1. The shell 1 may protect the fan assembly 4.

A battery receiver 5 is configured to receive a battery 6. The battery receiver 5 is disposed outside the shell 1 and is independently of the shell 1. In this way, the battery 6 may be disposed out of the shell, and the battery 6 may not be placed inside the shell 1, such that the battery 6 may be prevented from being blown by the air constantly. Constantly blowing the battery 6 may generate moisture for the battery 6, which may seriously affect the service life of the battery 6. Further, the weight applied to the neck caused by the battery may be reduced, relieving a pressure on the neck. Further, the battery receiver 5 protects the battery 6 from the external dust or rain, and the battery 6 may be replaced more easily, i.e., the battery 6 may be replaced by opening a cover 51 of the battery receiver 5, a replacement operation may be simple.

In some embodiments, the shell 1 may be curved to fit a shape of the user's neck, such that the shell may fit firmly with the user's neck, preventing the fan from shaking while being worn, such that the air flowing may be not affected. The fan assembly 4 is arranged in each of two end portions of the shell 1. In this way, weights of the two ends of the shell 1 may be increased. A certain downward traction for the neck fan may be generated at a front of the user when the neck fan is being worn, allowing the neck fan to fit firmly on the neck.

In some embodiments, as shown in FIGS. 46 and 47, the shell 1 may include a left head portion 11, a right head portion 12 and a connection portion 13. Two ends of the connection portion 13 may be connected to the left head portion 11 and the right head portion 12 respectively. In this way, the shell 1 may be easily assembled and disassembled.

In some embodiments, the connection portion 13 is a tubular structure having a plurality of tubes sleeving each other. That is, the connection portion 13 comprises a first connection portion 131 and a second connection portion 132. The first connection portion 131 is partially embedded in the second connection portion 132. An overall length of the connection portion 13 may be adjusted (extended or retracted) by adjusting a length of the first connection portion 131 embedded into the second connection portion 132. In this way, the connection part 13 connects to the left head portion 11 and the right head portion 12. The length of the connection portion 13 is adjusted based on a size of the neck, such that an overall length of the shell 1 is adjusted to suit various neck sizes of various users.

In some embodiments, the left head portion 11, the right head portion 12 and the connection portion 13 may be made of soft material. In this way, a size of the shell 1 may be adjusted based on the size of the user's neck, and the shell 1 may be adapted to various neck sizes.

In some embodiments, an upper face of the left head 11 portion and/or the right head portion 12 that defines the air outlet 3 is inclined at a predetermined angle towards an inner side, which is curved and arced, such that an area of the user that can be covered by the air flowing out of the neck fan may be increased.

In some embodiments, the predetermined angle may be in a range of 5° to 30° with respect to the vertical direction.

In some embodiments, the predetermined angle may be 10°, 15°, 20° or 25°. In detail, when the predetermined angle is 10°, an area covered by the air flowing out of a side of the neck fan may be maximum, but a wind force may be minimum. When the predetermined angle is 15°, the area covered by the air flowing out of the side of the neck fan may be a second maximum, and the wind force may be a second minimum. When the predetermined angle is 20°, the area covered by the air flowing out of the side of the neck fan may be relatively small, and the wind force may be relatively large. When the predetermined angle is 25°, the area may be straightforwardly covered by the air flowing out of the side of the neck fan, and the wind force may be maximum. The predetermined angle may be adjusted to generate various wind blowing experiences, situations that require various amounts of air flowing and cooling effects may be adapted.

In some embodiments, the left head portion 11 and the right head portion 12 may be structurally symmetrical. In the present embodiment, only the left head portion 11 may be described. The left head portion 11 may include an inner side shell 111 and an outer side shell 112 engaged with the inner side shell 111. The fan assembly 4 may be disposed between an end portion of the inner side shell 111 and an end portion of the outer side shell 112. An inner side cover 113 may be arranged on an inner face of the inner side shell 111. The air inlet 2 may be defined in the inner side cover 113. The air inlet 2 may be circular. An outer side cover 114 may be arranged on an outer face of the outer side shell 112. The inner side cover 113 and the outer side cover 114 may be arranged for protection. Further, a through hole may be defined in each of the inner side cover 113 and the outer side cover 114 for dissipating heat, increasing air circulation, and ensuring heat generated when the fan assembly 4 is operating to be dissipated out of the neck fan.

In some embodiments, at least two turbine fans may be arranged in the left head portion 11 and/or the right head portion 12. Each of the at least two turbine fans may intake the air from two opposite sides of the fan. Further, each of the two opposite side of each turbine fan in the shell 1 for intaking the air may correspond to a corresponding air inlet, such that the amount of air intake may be increased.

In some embodiments, a position of the outer side shell 112 corresponding to the fan assembly 4 may define an auxiliary air inlet 1121. On one hand, the auxiliary air inlet 1121 may correspond to the air inlet 2 in the inner side cover 113, allowing the air to enter the neck fan from two opposite sides, preventing wind stifling and wind noise generated by intaking the air from only one side, and ensuring the fan assembly to intake a sufficient amount of the air. On the other hand, the heat generated by the fan assembly 4 may be dissipated from the auxiliary air inlet 1121, and a weight of the entire structure may be reduced.

In some embodiments, the air inlet 2 may be defined in two end portions of the shell 1 and may correspond to the fan assembly 4. In one case, when the neck fan is hanging around the user's neck, the end portions of the shell 1 may not attach the user's skin or clothes. More specifically, an inner face of the end portions and an outer face of the end portions do not attach to the user's skin. A middle portion or portions near the middle portion of the shell 1 may attach to the user's skin or clothes. Therefore, defining the air inlet 2 in the end portions of the shell 1 allows the air to enter the shell 1 fluently. A case where the air inlet 2 is blocked by the user's skin or clothes, preventing the air from flowing through the air inlet 2, may be prevented. Further, a position of the air inlet 2 corresponding to a position of the fan assembly 4 minimizes a distance that the air flows from the air inlet 2 to the fan assembly 4, such that the fan assembly 4 may generate the wind in real time. The air outlet 3 may be defined in an inner face or an upper face of the shell 1. In one case, when the neck fan is hanging around the user's neck, the inner face of the shell 1 may attach to the user's skin to allow the skin to be covered by the wind optimally. Therefore, the air outlet 3 is defined in the inner face of the shell 1. Defining the air outlet 3 in the upper face of the shell 1 allows the air out of the neck fan may flow along the user's neck to reach the user's head, due to the air flowing, areas of the user's neck and the user's head covered by the wind may be maximized.

In some embodiments, the fan assembly 4 may include a fan impeller, a motor for driving the fan impeller to rotate, and a control board for controlling a rotating speed of the motor. The control board may be connected to the motor. The amount of the air flowing out of the neck fan can by adjusted by adjusting the rotating speed of the motor.

In some embodiments, the fan impeller may include fan blades 41 and a rotating wheel 42. The fan blades 41 may be arranged around a wheel face of the rotating wheel 42. A gap may be defined between the fan blades 41 and the inner wall of the shell 1. The gap may be in a range of 2 mm to 5 mm. Defining the gap may reduce a distance between the fan blades 41 and the inner wall of the shell 1, such that wind stifling may be prevented, and the wind noise may be reduced. Further, the gap may not be excessively small, such that when the neck fan is shaken, friction may be prevented between the fan blades 41 and the inner wall of the shell 1, and a structural damage may be prevented.

In some embodiments, as shown in FIGS. 46 and 47, the inner wall of the shell 1 may extend to form a wind guide plate 14. The wind guide plate 14 may extend along an outer circumference surface of the fan blades towards an inner middle of the shell 1. The wind guide plate 14 separates the fan assembly 4 and the air duct from the control board. The air duct refers to a gap between components inside the shell 1 for the air to flow through. In this way, the air and/or the water flowing in the air duct may not erode the control board. The wind guide plate 14 may guide the wind generated by the fan assembly 4 and guide the air to flow from the end portion of the shell 1 to the middle of the shell 1, allowing the entire space inside the shell 1 to be covered by the wind. In this way, the air may flow out through various air outlets 3, allowing the space covered by the air flowing out of the neck fan to be maximized.

In some embodiments, the plurality of air outlets 3 may be spaced apart from each other and arranged along the extending direction of the wind guide plate 14. In this way, the air outlets 3 may optimally cover a route along which the wind guide plate 14 extends, such that the wind may be blown out of the shell 1 uniformly from various air outlets, and an air blowing effect may be increased.

In some embodiments, as shown in FIGS. 46 and 47, two fan impellers may be arranged at each of two end portions of the shell 1. One of the two impellers near the end portion of the shell 1 may be surrounded by the wind guide plate 14, and the wind guide portion 14 extends upwardly to reach the inner wall of the shell 1, such that a first air duct may be defined. The other one of the two impellers away from the end portion of the shell 1 may be partially surrounded by the wind guide portion 14, and the wind guide plate 14 extends towards the middle portion of the shell 1, such that a second air duct may be defined. The first air duct does not communicate with the second air duct. In this way, wind generated by one of the two impellers and wind generated by the other one of the two impellers may not compressed with each other, such that wind stifling may be prevented, and the wind noise may be prevented. In detail, the air in the first air duct may flow out of the shell 1 from the air outlet 3 in the end portion of the shell 1, and the air in the second air duct may flow out of the shell 1 from the air outlets 3 in other portions of the shell 1. In this way, the air in the first air and the air in the second air duct may not be communicated or compressed with each other, such that the wind noise may be reduced.

In some embodiments, the battery receiver 5 may be connected a first end of a wire 7. A second end of the wire 7 may be inserted into the shell 1 and connected to the control board. That is, the battery receiver 5 and the shell 1 may be detachably connected with each other via the wire 7, such that the neck fan may be more portable.

In some embodiments, a position of the second end of the wire 7 that connects the shell 1 may be near the end portion of the shell 1. In this way, a traction force generated by the battery receiver 5 is applied to the end portion of the shell 1. When the neck fan is worn to the user's neck, the gravitational center of the neck fan may be moved to a front of the neck fan, allowing the shell 1 to attach to the user's neck more properly. When the user is moving, the neck fan may not move backwards, such that the shell 1 may not depart away from the user's neck. That is, the neck fan may be attached to the user's neck more stably.

In some embodiments, an end of the wire 7 may be rotatably connected to the battery receiver 5. That is, a position at which the battery receiver 5 is disposed may be adjusted by rotating. A fixing portion may be arranged on a side of the battery receiver 5 to fixedly clamp the battery receiver 5. In detail, the fixing portion may be an adhesive layer arranged on a surface of the battery receiver 5, enabling the battery receiver 5 to b adhesively fixed to clothes of the user. The fixing portion may alternatively be a clamping plate arranged on the surface of the battery receiver 5, enabling the battery receiver 5 to clamp the clothes of the user, such that the battery receiver 5 may be fixed.

According to the present embodiment, the neck fan may include a shell, a fan assembly, and a battery receiver. The shell may define the air inlet and the air outlet. The fan assembly may be configured to drive the external air to enter the neck fan through the air inlet, and drive the air to flow out of the neck fan through the air outlet. The fan assembly may be arranged inside the shell. The battery receiver may be configured to receive the battery. The battery receiver may be disposed out of the shell, and may be independent from the shell 1. In this way, the neck fan may blow the wind towards the user's neck, and the battery of the neck fan may not be affected by the wind.

FIGS. 48-52 show a neck fan according to another embodiment of the present disclosure.

Figure 48:
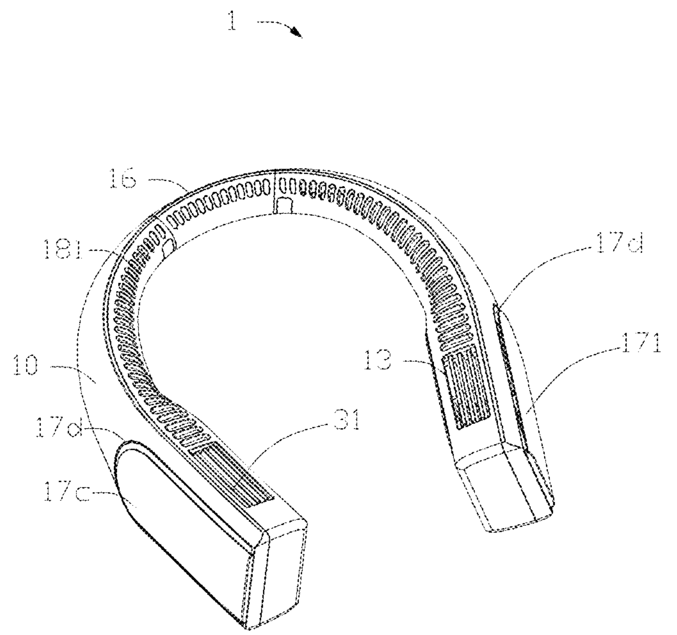
FIG. 48 is a schematic view of a neck fan according to an embodiment of the present disclosure.
Figure 49:
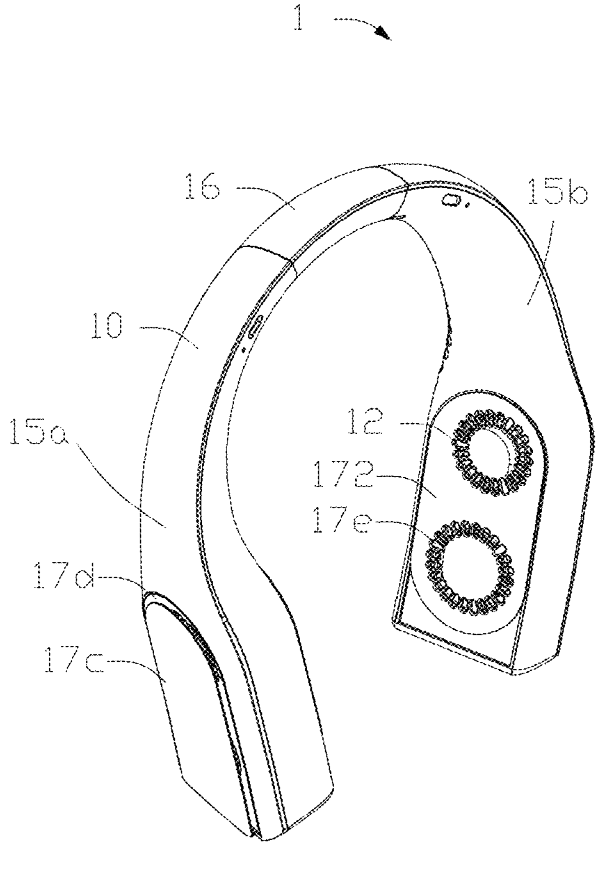
FIG. 49 is a schematic view of the neck fan shown in FIG. 48 from another view angle.

FIG. 48 is a schematic view of a neck fan according to an embodiment of the present disclosure, and FIG. 49 is a schematic view of the neck fan shown in FIG. 48 from another view angle. The neck fan 1 may include a shell 10, a fan assembly 20 and an outlet adjustment assembly 30.

Figure 50:
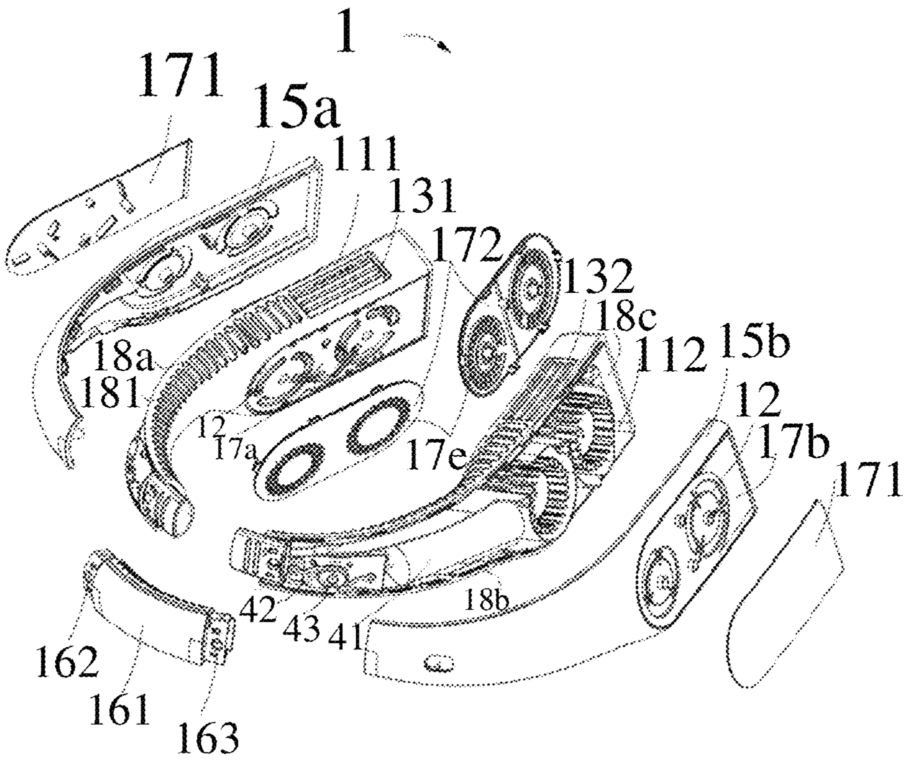
FIG. 50 is an exploded view of the neck fan shown in FIG. 48.
Figure 51:
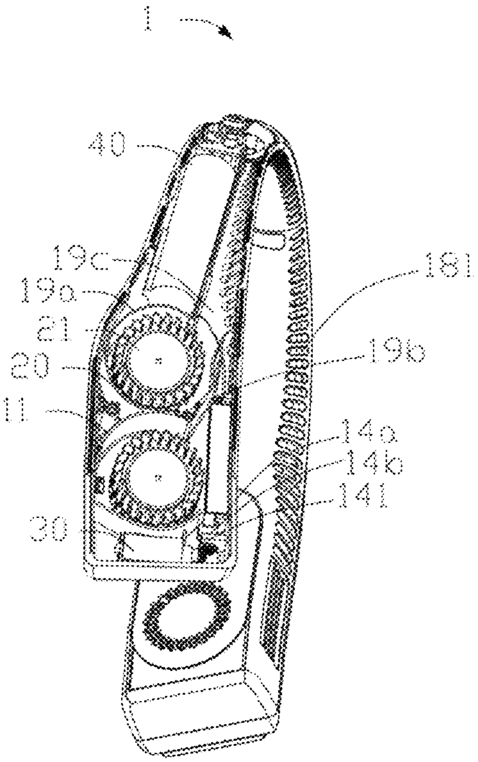
FIG. 51 is a schematic view of a portion of the neck fan shown in FIG. 48.
Figure 52:
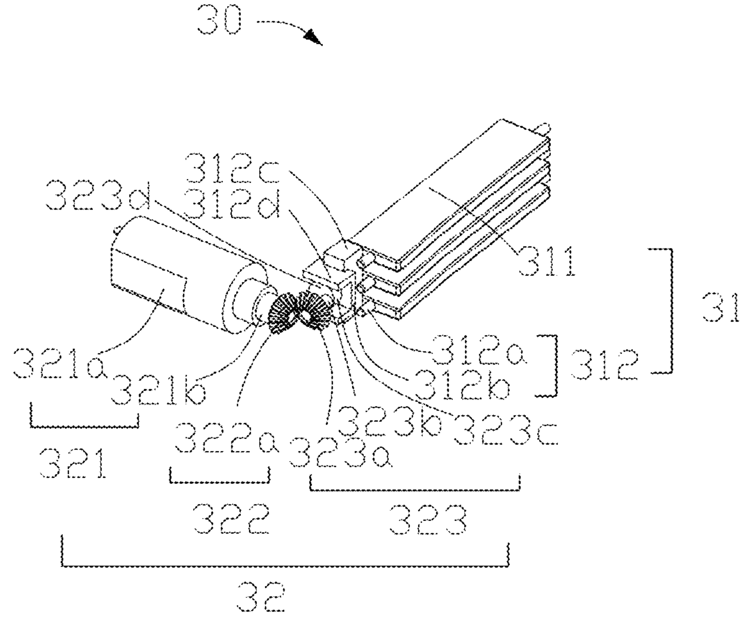
FIG. 52 is a schematic view of an outlet adjustment assembly of the neck fan shown in FIG. 48.

FIG. 50 is an exploded view of the neck fan shown in FIG. 48, FIG. 51 is a schematic view of a portion of the neck fan shown in FIG. 48, and FIG. 52 is a schematic view of an outlet adjustment assembly of the neck fan shown in FIG. 48. The shell 10 may extend along a predetermined direction and define a receiving chamber 11, an air inlet 12, an air outlet 13. The receiving chamber 11 extends along a predetermined direction. The air inlet 12 may communicate with the receiving chamber 11. The air outlet 13 may communicate with the receiving chamber 11. The fan assembly 20 may be received in the receiving chamber 11, and configured to guide the air from the air inlet 12 to flow to the air outlet 13. The outlet adjustment assembly 30 may include an outlet adjustment plate 31 and a driving assembly 32. The outlet adjustment plate 31 may be disposed near the air outlet 13 and may be movably connected to the shell 10. The driving assembly 32 may be received in the receiving chamber 11 and may be connected to the outlet adjustment plate 31. When the user is wearing the neck fan 1, and when the user needs to adjust an air outlet angle of the neck fan 1, a remote control, a switch, and the like may be taken to control the driving assembly 32 to operate, and the driving assembly 32 may drive the outlet adjustment plate 31 to move relative to the shell 10 to change an angle between the outlet adjustment plate 31 and the shell 10. In this way, the air outlet angle out of the air outlet 13 may be adjusted, and the amount of air out of the air outlet 13 may be adjusted.

In the neck fan 1 of the present embodiment, the outlet adjustment plate 31 near the air outlet 13 and movably connected to the shell 10 may be driven by the control assembly 32 to move relative to the shell 10 to adjust the air flowing out of the air outlet 13. In this way, while using the neck fan, the air flowing out of the fan may be adjusted, meeting various requirements of the user. Further, the driving assembly 32 is taken to adjust the outlet adjustment plate 31, and therefore, the air outlet may be adjusted accurately without manual operations. The neck fan may be used conveniently, improving the user's experience. In addition, the fan assembly 20 may be received in the receiving chamber 11, and the air at the air inlet 12 may be guided to the air outlet 13. In this way, the hair and other foreign matter may not wind around the fan assembly 20, the neck fan may be used safely and conveniently. Further, the wind noise may be reduced, the loss in the air flowing may be reduced, and the air flowing efficiency of the neck fan 1 maybe improved.

Further, the outlet adjustment plate 31 may include at least two plate portions 311 spaced apart from each other and a connection portion connected to the at least two plate portions. The at least two plate portions 311 may be received in the air outlet 13 to divide the air outlet 13 into at least two sub-outlets. The number of the plate portions 311 may be determined appropriately based on a size of air outlet 13. In the present embodiment, three plate portions 311 may be arranged. The connection portion 312 may include a first connection portion 312*a* and a second connection portion 312*b*. The shell 10 may include a third connection portion 14*a* near the air outlet 13. The third connection portion 14*a* may be movably connected to the first connection portion 312*a*. the second connection portion 312*b* may be connected to the driving assembly 32. Arranging at least two plate portions 311 spaced apart from each other and disposing the at least two plate portions 311 in the air outlet 13 to divide the air outlet 13 into the at least two sub-outlets, allows the air to flow out of the neck fan 1 more uniformly, and enables an air out flowing direction from the air outlet 13 to be adjusted. In addition, the third connection portion 14*a* of the shell 10 may be movably connected to the first connection portion 312*a* of the outlet adjustment plate 31. The second connection portion 312*b* of the outlet adjustment plate 31 may be connected to the driving assembly 32. In this way, the driving assembly 32 may drive the plate portions 311 through the second connection portion 312*b*, such that the air out flowing direction of the air outlet 13 may be adjusted. Further, the movable connection between the third connection portion 14*a* and the first connection portion 312*a* allows the outlet adjustment plate 31 to be stably connected to the shell 10, ensuring the neck fan 1 to be stable and safe while the air out flowing direction is being adjusted.

In detail, the third connection portion may be rotatably connected to the first connection portion 312*a*. One of the third connection portion 14*a* and the first connection portion 312*a* may include a pivot, and the other one of the third connection portion 14*a* and the first connection portion 312 may define a pivot hole. In the present embodiment, the first connection portion 312*a* includes the pivot, and the third connection portion 14*a* defines the pivot hole. The pivot is at least partially received in the pivot hole to achieve rotation connection between the third connection portion 14*a* and the first connection portion 312*a*. Since one of the third connection portion 14*a* and the first connection portion 312*a* includes the pivot, and the other one of the third connection portion 14*a* and the first connection portion 312 defines the pivot hole, the pivot is at least partially received in the pivot hole to achieve rotation connection between the third connection portion 14*a* and the first connection portion 312*a*, the structural connection may be simple, and the connection may be reliable.

Further, the driving assembly 32 may include a driving member 321, a first transition member 322, and a second transition member 323. The first transition member 322 may be connected to the driving member 321. The second transition member 323 may be connected between the first transition member 322 and the second connection portion 312*b*. The driving member 321 may include a driving body 321*a* and a driving shaft 321*b* connected to the first driving body 321*a*. The first transition member 322 may include a first cone gear 322*a*. The first cone gear 322*a* may sleeve on the driving shaft 321*b*. The second transition member 323 may include a second cone gear 323*a* engaged with the first cone gear 322*a*, a transition shaft 323*b* connected to the second cone gear 323*a*, and a transition portion 323*c* connected between the transition shaft 323*b* and the second connection portion 312*b*. The driving body 321*a* drives the driving shaft 321*b* to rotate, such that the first cone gear

322*a* rotates. Further, the engagement drives the second cone gear 323*a* that engages with the cone gear 322*a* to rotate, such that the outlet adjustment plate 31 may be driven to rotate to adjust the air out flowing direction, the structure may be simple and reliable.

In detail, an extending direction of the driving shaft 321*b* may be perpendicular to an extending direction of the transition shaft 323*b*. the transition portion 323*c* may include a circular plate 323*d*. the transition shaft 323*b* may be eccentrically connected to a plate surface of the circular plate 323*d* away from the second connection portion 312*b*. When the driving body 321*a* drives the driving shaft 321*b* to rotate to drive the transition shaft 323*b* to rotate, since the transition shaft 323*b* is eccentrically connected to the circular plate 323*d*, the second transition member 323 may drive the outlet adjustment plate 31 to rotate around the pivot shaft while the outlet adjustment plate 31 is swinging to the left and to the right. In this way, an adjustment range of the air out flowing direction may be increased. The second connection portion 312*b* may include a first portion 312*c* connected to the plate portions 311 and a second portion 312*d* connected to the first portion 312*c*. A cross section of the second portion 312*d* may be U shaped, and the second portion 312*d* may define a receiving space. That is, the second portion 312*d* defines a U-shaped receiving space. The opening of the receiving space of the second portion 312*d* may face the transition portion 323*c*. The transition portion 323*c* may be received in the U-shaped receiving space. The shell 10 may further include a fourth connection portion 14*b*. The fourth connection portion 14*b* may be connected to a body of the shell 10 and may be disposed between the third connection portion 14*a* and the second cone gear 323*a*. The fourth connection portion 14*b* may define a guide hole 141. The transition shaft 323*b* may extend through the guide hole 141 and may be movable in the guide hole. The guide hole 141 may be a strip-shaped hole and may communicate with an external of the neck fan. Arranging the transition shaft 323*b* to be eccentrically connected to the plate face of the circular plate 323*d* away from the second connection portion 312*b* increases the adjustment range of the air out flowing direction. Further, the transition portion 323*c* is received in the U-shaped receiving space, such that the transition portion 323*c* may be stably connected to the second connection portion 312*b* while rotating, and the transition portion 323*c* may not be detached easily. In addition, arranging the fourth connection portion 14*b*, defining the guide hole 141 in the fourth connection portion 14*b*, and defining the guide hole 141 to be strip-shaped and communicating with the external, allows the second transition member 323 to be assembled easily, and a position of the second transition member 323 may be limited and supported stably.

Further, the shell 10 may include a first shell 15*a* arranged near a side of the user's neck and a second shell 15*b* arranged near another side of the user's neck. The receiving chamber 11 may include a first sub-chamber 111 defined in the first shell 15*a* and a second sub-chamber 112 defined in the second shell 15*b*. The air inlet 12 may include a first air inlet 12 defined in the first shell 15*a* and a second air inlet 12 defined in the second shell 15*b*. The air outlet 13 may include a first air outlet 131 defined in the first shell 15*a* and a second air outlet 132 defined in the second shell 15*b*. Two fan assemblies 20 may be arranged, and two outlet adjustment assemblies 30 may be arranged. One of the two fan assemblies 20 may be received in the first sub-chamber 111, and configured to guide the air from the first air inlet 12 to flow to the first air outlet 131. The other one of the two fan assemblies 20 may be received in the second sub-chamber 112, and configured to guide the air from the second air inlet 12 to flow to the second air outlet 132. One of the two outlet adjustment assemblies 30 may be received in the first sub-chamber 111 and configured to adjust the air flowing out through the first air outlet 131. The other one of the two outlet adjustment assemblies 30 may be received in the second sub-chamber 112 and configured to adjust the air flowing out through the second air outlet 132. In the present embodiment, the two fan assemblies 20 may be received in the first sub-chamber 111 of the first shell 15*a* and the second sub-chamber 112 of the second shell 15*b* respectively. In this way, the air may flow out of the neck fan from two opposite sides of the user's neck at the same time, cooling the user quickly. Since the first shell 15*a* and the second shell 15*b* are arranged, and each of the first shell 15*a* and the second shell 15*b* corresponds to one fan assembly 20, an air flowing efficiency out of the neck fan 1 may be increased. Further, the two fan assemblies 20 are received in the first sub-chamber 111 and the second sub-chamber 112 respectively, the air flowing caused by the two fan assemblies may not interfere each other, the air flowing efficiency out of the neck fan 1 may further be increased.

Further, the shell 10 may further include a connection assembly 16 connected between the first shell 15*a* and the second shell 15*b*. The connection assembly 16 may include a connection shell 161, a first connection member 162 and a second connection member 163. The connection shell 161 may be a curved hollow tube. An end of the first connection member 162 may be connected to and arranged inside an end of the connection shell 161, and the other end of the first connection member 162 may be connected to and arranged inside an end of the first shell 15*a*. An end of the second connection member 163 may be connected to and arranged in the other end of the connection shell 161, and the other end of the second connection member 163 may be connected to and arranged inside the other end of the second shell 15*b*. In the present embodiment, the connection assembly 16 is configured to connect the first shell 15*a* to the second shell 15*b*, such that the neck fan 1 may hang around the user's neck, the structure of the neck fan may be simple, the neck fan may be easily manufactured, and may be easily assembled.

Further, the fan assembly 20 may include turbine blades 21. The fan assembly 20 in each of the first sub-chamber 111 and the second sub-chamber 112 may include at least two turbine blades. The at least two turbine blades 21 may be arranged along a predetermined direction. An air flowing direction generated by the turbine fans may be perpendicular to an extending direction of the rotation shaft of the fan. In this way, an increased air volume may be generated while a reduced space may be occupied, such that the amount of air flowing out of the neck fan 1 may be increased, the user may be cooled quickly. The neck fan 1 may further include an electric control assembly 40, received in one of the first sub-chamber 111 and the second sub-chamber 112. The electric control assembly 40 may include a battery 41, a circuit board 42, and a control switch 43. The circuit board 42 may be electrically connected to the battery 41 and the control switch 43. The neck fan 1 may be supplied with power by the battery 41. The user may carry and user the neck fan at anytime and anywhere. In the present embodiment, the fan assembly 20 includes the turbine blades 21, the fan assembly 20 in each of the first sub-chamber 111 and the second sub-chamber 112 includes at least two turbine blades, and the at least two turbine blades 21 are arranged along the predetermined direction, such that the air flowing efficiency of the neck fan 1 may be improved effectively.

Further, the shell 10 may include an inner plate 17 near the user's neck, an outer plate 17*b* opposite to the inner plate 17*a*, a first connection plate 18*a*, a second connection plate 18*b*, and an end plate 18*c*. The first connection plate 18*a* may be connected to a side of the inner plate 17*a* and a side of the outer plate 17*b*, and may be arranged near the user's face. The second connection plate 18*b* may be connected to another side of the inner plate 17*a* and another side of the outer plate 17*b*. The end plate 18*c* may be connected to the inner plate 17*a*, the outer plate 17*b*, the first connection plate 18*a* and the second connection plate 18*b*. The air inlet 12 may be defined in at least one of the inner plate 17*a* and the outer plate 17*b*. The air outlet 13 may be defined in the first connection plate 18*a*. The first connection plate 18*a* may define a plurality of air outlets 18*a* communicating with the receiving chamber 11. Sizes of the plurality of air outlets 181 may be gradually decreased along a direction away from the air outlet 13. In the present embodiment, each of the inner plate 17*a* and the outer plate 17*b* defines the air inlet 12, such that the amount of air flowing into the neck fan 1 may be increased, an air intaking efficiency of the neck fan 1 may be increased. The plurality of air outlets 181, which are defined in the first connection plate 18*a* and communicating with the receiving chamber 11, may be arranged around an outer periphery of the user's neck. In this way, the plurality of air outlets 181 and the air outlet 13 may cooperatively allow the air to flow out of the neck fan, enabling the user to feel comfortable. The driving assembly 32 is disposed between the end plate 18*c* and the fan assembly 20. The shell 10 may further include a first partition plate 19*a* and a second partition plate 19*b*. The first partition plate 19*a* is arranged to surround an outer side of the fan assembly 20. The second partition plate 19*b* may be connected to the first partition plate 19*a* and extend towards a side away from the end plate 18*c*. The second partition plate 19*b* and the first connection plate 18*a* may define an air duct 19*c* communicating with the air outlets 181, such that the fan assembly 20 may drive the air from the air inlet 12 to flow along the air duct 19*c* to the air outlets 181. In the present embodiment, the air inlet is defined in at least one of the inner plate 17*a* and the outer plate 17*b*, and the air outlet 13 is defined in the first connection plate 18*a*. In this way, the air inlet and the air outlet may not be communicated and interfere with each other. The plurality of air outlets 181 are defined in the first connection plate 18*a* and communicating with the receiving chamber 11, such that the amount of air flowing out of the neck fan 1 may be increased, increasing the air flowing efficiency out of the neck fan. The second partition plate 19*b* and the first connection plate 18*a* define the air duct 19*c* communicating with the air outlets 181, such that the fan assembly 20 may drive the air from the air inlet 12 to flow along the air duct 19*c* to the air outlets 181. In this way, the loss of the wind of the fan assembly 20 while flowing in the receiving chamber 11 may be reduced, further increasing the air flowing efficiency out of the neck fan.

Further, the shell 10 may further include an air inlet cover 17*c*. A position at which the air inlet cover 17*c* is arranged may correspond to the air inlet 12. Further, an inlet gap 17*d* may be defined between the air inlet cover 17*c* and an outer surface of the shell 10 and may communicate with the air inlet 12. In this way, the air out of the neck fan 1 may enter the receiving chamber 11 by flowing through the inlet gap 17*d* and the air inlet 12. Each of the inner plate 17*a* and the outer plate 17*b* may define the air inlet 12. The air inlet cover 17*c* may include a first inlet cover 171 and a second inlet cover 172. The first inlet cover 171 may be arranged on a side of the outer plate 17*b* away from the inner plate 17*a*. The second inlet cover 172 may be arranged on a side of the inner plate 17*a* away from the outer plate 17*b*. The inlet gap 17*d* may be defined between the first inlet cover 171 and the outer surface of the outer plate 17*b*, and may communicate with air inlet 12 of the outer plate 17*b*. In this way, the air out of the neck fan 1 may enter the receiving chamber 11 through the inlet gap 17*d* and the air inlet 12 of the outer plate 17*b*. The second inlet cover 172 may define a plurality of air inlets 17*e* corresponding to the air inlet 12 of the inner plate 17*a*, such that the air out of the neck fan 1 may enter the receiving chamber 11 through the air inlets 17*e* and the air inlet 12 of the inner plate 17*a*. It shall be understood that, the inlet gap 17*d* may compress the air flowing into the neck fan and allow an air pressure near the air inlet 12 to be greater than an air pressure in the receiving chamber 11. In this way, a negative pressure is generated to push the air out of the neck fan 1 towards the air inlet 12, increasing an air flowing speed, maximizing an air intaking efficiency of the neck fan 1. Further, the efficiency of the air flowing out of the neck fan 1 may be increased, and the user may be cooled quickly. By arranging the air inlet cover 17*c*, the hair or the foreign matters may not wind to the fan assembly easily, allowing the neck fan to be used safely and conveniently, and reducing the wind noise.

FIGS. 53-57 show a neck fan according to an embodiment of the present disclosure.

An arrow X in the figures indicate a front-rear direction, i.e., a front side-rear side direction. An arrow Y in the figures indicate a horizontal direction, i.e., a left-right direction. An arrow Z in the figures indicate a vertical direction, i.e., an up-down direction.

Figure 53:
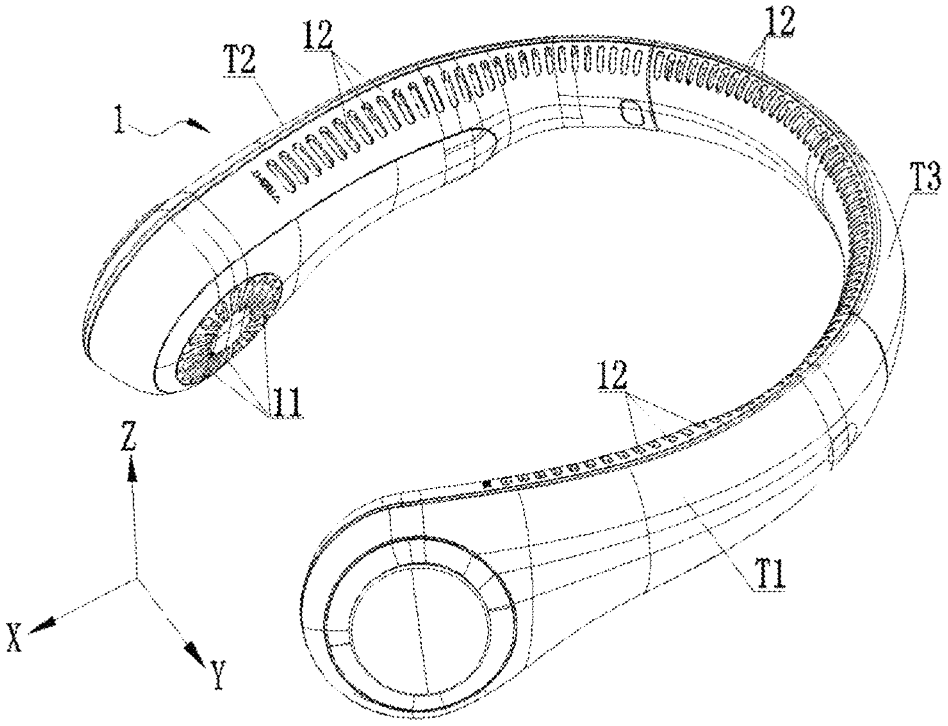
FIG. 53 is a schematic view of a neck fan according to an embodiment of the present disclosure.
Figure 54:
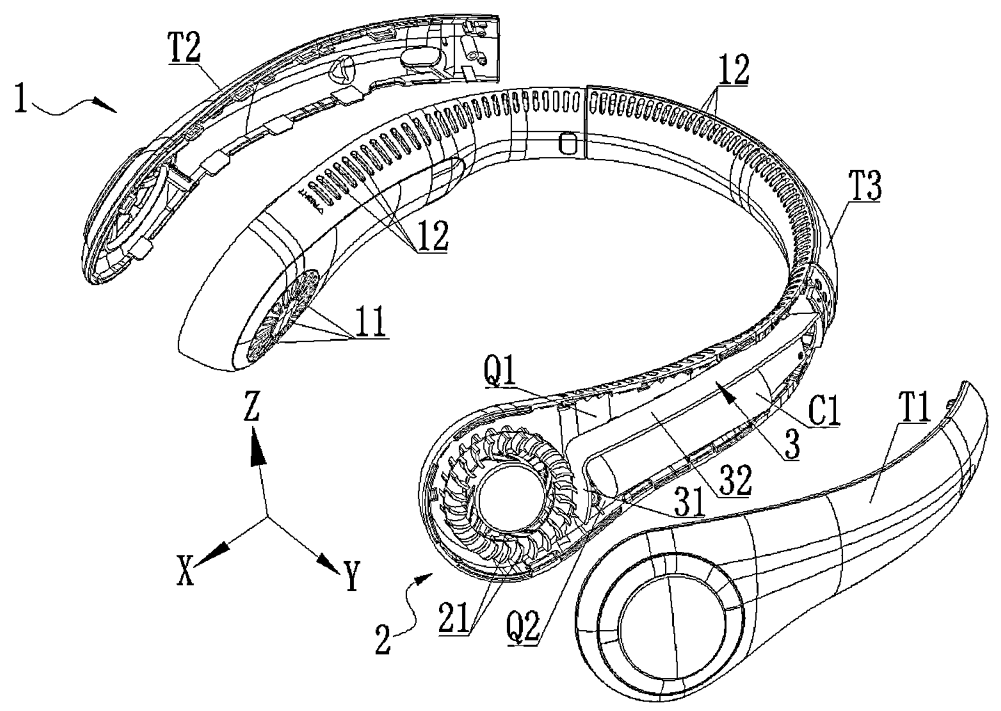
FIG. 54 is an exploded view of the neck fan shown in FIG. 53.
Figure 55:
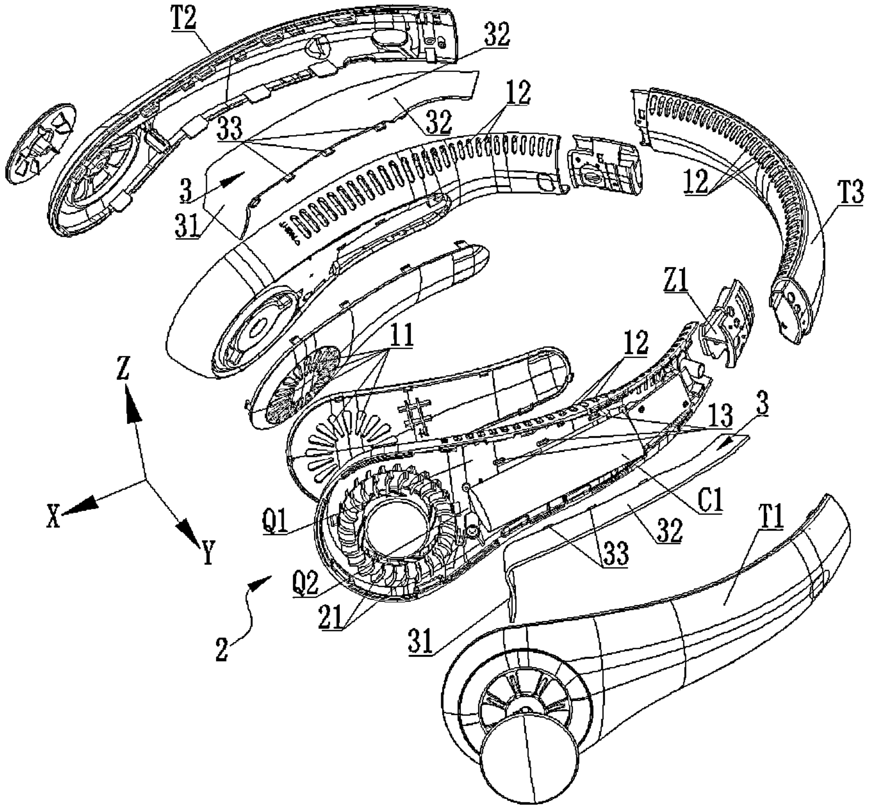
FIG. 55 is an exploded view of the neck fan shown in FIG. 53.

As shown in FIGS. 53-55, the neck fan may include a shell 1, a fan assembly 2, and a wind guide member 3. The shell 1 may be configured to hang around the user's neck. The shell 1 may define an air inlet 11, an air outlet 12, and an air duct defined in the shell 1. The air duct may communicate with the air inlet 11 and the air outlet 12. The fan assembly 2 may be arranged inside the shell 1 and configured to guide the external into the neck fan through the air inlet 11, and drive the air to flow along the air duct to the air outlet 12. The wind guide member 3 may be detachably received in the air duct and configured to guide and separate the air flowing in the air duct. The wind guide member 3 may extend from the fan assembly 2 towards the air duct. The wind guide member 3 may divide the air duct, such that the air may flow along predetermined tracks, and the air may be collectively transported to the divided air duct. In this way, the air may flow to approach the air outlet 12, allowing the air flowing out of the neck fan more uniformly. Further, the speed of the air flowing out of the neck fan may be increased, improving the user's experience. Further, the wind guide member 3 is detachably received in the air duct, the wind guide member may be assembled and detached quickly, and may be easily replaced in the future.

In some embodiments, the wind guide member 3 may be a curved wind separation plate. A first end 31 of the wind separation plate may be curved and bent and may be disposed near the fan assembly 2. A plate face 32 of the wind separation plate may correspond to the air outlet 12. The plate face 32 of the wind separation plate may separate the air duct to define a first air chamber Q1 and a second air chamber Q2. The first air chamber Q1 may communicate with the air outlet 12. In detail, the first air chamber Q1 is defined above the wind separation plate, and the second air chamber Q2 is defined below the wind separation plate. That is, the first air chamber Q1 may be above the second air chamber Q2. The first air chamber Q1 is defined to allow the air to flow along, enabling the air to flow to the air outlet 12. The second air chamber Q2 is defined to receive an electronic element, such as a battery C1, a circuit board of the neck fan, and so on.

In some embodiments, a cross section area of the first air chamber Q1 may be gradually decreased along a direction away from the fan assembly 2. In this way, a cross section area of the air duct away from the fan assembly 2 may be decreased gradually, compressing the air in the air duct, such that an air flowing speed may be increased, and an amount of air flowing out of the neck fan may be increased. In this way, the amount of air flowing out of the neck fan at a position away from the fan assembly 2 may be the same as the amount of air flowing out of the neck fan at a position near the fan assembly 2. The user may feel that the amount of air flowing out of the neck fan through various air outlets are uniform, improving the user's experience.

In some embodiments, a curved and bent contour of the first end 31 of the wind separation plate may fit with a contour of an outer circumference of the fan assembly 2. In this way, the wind generated from the fan assembly 2 may flow by touching the plate face 32 of the wind separation plate, reducing a resistance against the air flowing, optimally maintaining the air flowing speed.

Figure 56:
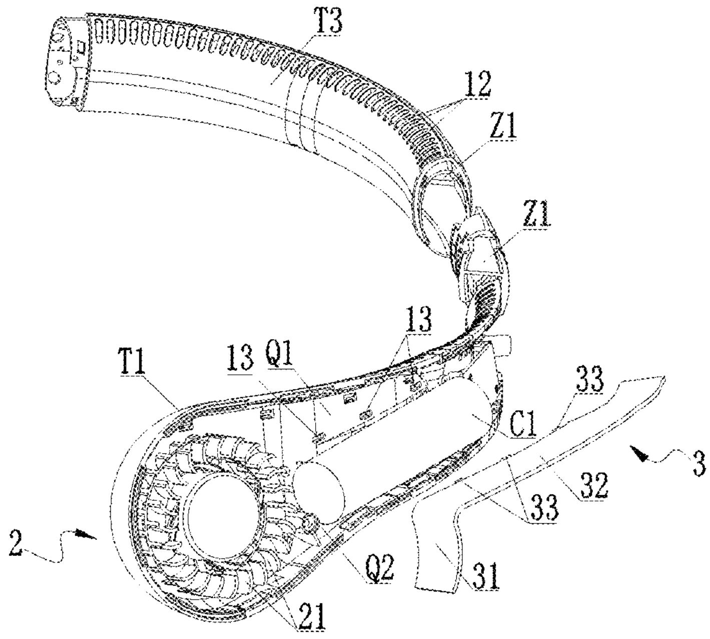
FIG. 56 is an exploded view of connection between a middle connection portion and a first end head portion of a neck fan according to an embodiment of the present disclosure.
Figure 57:
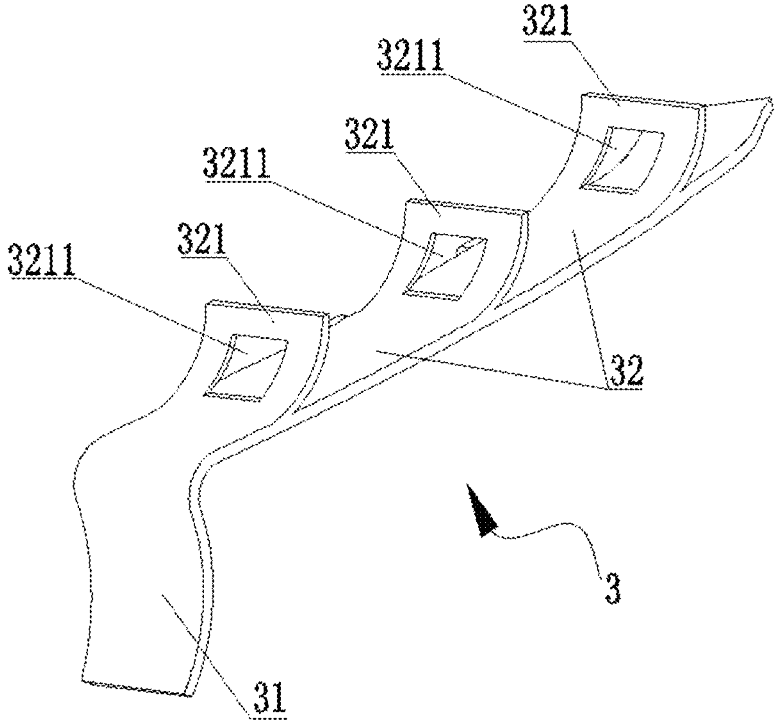
FIG. 57 is a schematic view of a wind guide member of a neck fan according to an embodiment of the present disclosure.

In some embodiments, as shown in FIGS. 56 and 57, at least one wind equalizing plate 321 may extend out from the plate face 32 of the wind separation plate and may face the air outlet 12. The wind equalizing plate 321 may define a through hole 3211 to allow the air to flow through. The wind equalizing plate 321 allows the air in the first air chamber Q1 to flow out of the air outlet 12 uniformly. In some embodiments, after the wind is generated by the fan blades 21 of the fan assembly, most of the air may flow along the wind separation plate towards the air duct, but may not saturate to flow upwardly towards the air outlet 12. Arranging the wind equalizing plate 321 may facilitate the air flowing directions to be changed, such that the air flowing through each air outlet 12 may be uniform, and each air outlet 12 may be saturated by the air. Further, the rest of the air that does not flow out through the air outlet 12 may continue flowing along the wind separation plate deeply to the air duct.

In some embodiments, the wind equalizing plate 321 may be curved. A tangent of a curved face of the wind equalizing plate 321 may be obtained. An angle between the tangent and the plate face of the wind separation plate may be in a range of 30° to 90°. In this way, when the air contacts the wind equalizing plate 321, the resistance against the air flowing along the wind equalizing plate 321 to the air outlet 12 may be relatively small. Therefore, the air flowing speed may be maintained optimally, and the resistance against the wind may be reduced.

In some embodiments, the shell 1 may include a first end head portion T1, a second end head portion T2, and a middle connection portion T3. The middle connection portion T3 may be connected between the first end head portion T1 and the second end head portion T2. At least one fan assembly 2 may be arranged inside at least one of the first end head portion T1 and/or the second end head portion T2. An auxiliary wind separation plate Z1 may be arranged inside the middle connection portion T3. An end portion of the auxiliary wind separation plate Z1 may align to an end portion of the wind separation plate in the first end head portion T1 and/or the second end head portion T2. In this way, the air duct in each of the first end head portion T1, the second end head portion T2, and the middle connection portion T3 is divided. Further, when the air in the first air chamber Q1 of the first end head portion T1 and/or the second end head portion T2 flows to the middle connection portion T3, the air may also flow along the auxiliary wind separation plate Z1 to further reach the middle portion of the shell 1. Therefore, in the present embodiment, the air in the entire may flow through the air ducts defined in the entire shell 1 to reach the air outlet 12 to exit the neck fan, further enabling the air flowing out of various outlets to be uniform, improving the user's experience.

In some embodiments, the fan assembly 2 may include fan blades 21 and a motor driving the fan blades 21 to rotate. The air inlet 11 may be defined a side face of the first end head portion T1 and the second end head portion T2. A position in which the air inlet 11 is defined may correspond to a position at which the fan assembly 2 is arranged. The air outlet 12 is defined in an inner surface and/or an upper surface of the shell 1, such that the wind may be blown towards the user's neck. When the air outlet 12 is defined in the upper surface of the shell 1, the air may be blown out of the neck fan straightforwardly, and the air may flow upwards along the user's neck, such that the user's face, rear of the user's ears, and the user's head may be blown by the air. An area covered by the air may be increased, improving the user's experience.

In some embodiments, the wind guide member 3 may be inserted or embedded into the inner wall of the shell 1, such that the wind guide member 3 may be assembled and detached easily.

In some embodiments, the wind guide member may be arranged in a protrusion 33 protruding side-ward. The inner wall of the shell 1 may define a slot 13 for receiving the side-ward protrusion 33.

According to the present embodiment, the neck fan may include the shell, the fan assembly, and the wind guide member. The shell may be configured to hang around the user's neck. The shell may define the air inlet, the air outlet, and the air duct defined in the shell. The air duct may communicate with the air inlet and the air outlet. The fan assembly may be arranged inside the shell and configured to drive the external air to flow through the air inlet, and drive the air to flow along the air duct to reach the air outlet. The wind guide member may be detachably received in the air duct and configured to separate and guide the air in the air duct. The wind guide member may extend from the fan assembly towards the air duct. The neck fan of the present embodiment may divide the air duct, allowing the air to uniformly flow out of various air outlets. Further, the wind guide member may be easily assembled and detached.

FIGS. 58-66 show a neck fan according to some embodiments of the present disclosure.

An arrow X in the figures indicate a front-rear direction. An arrow Y in the figures indicate a left-right direction. An arrow Z in the figures indicate an up-down direction.

Figure 58:
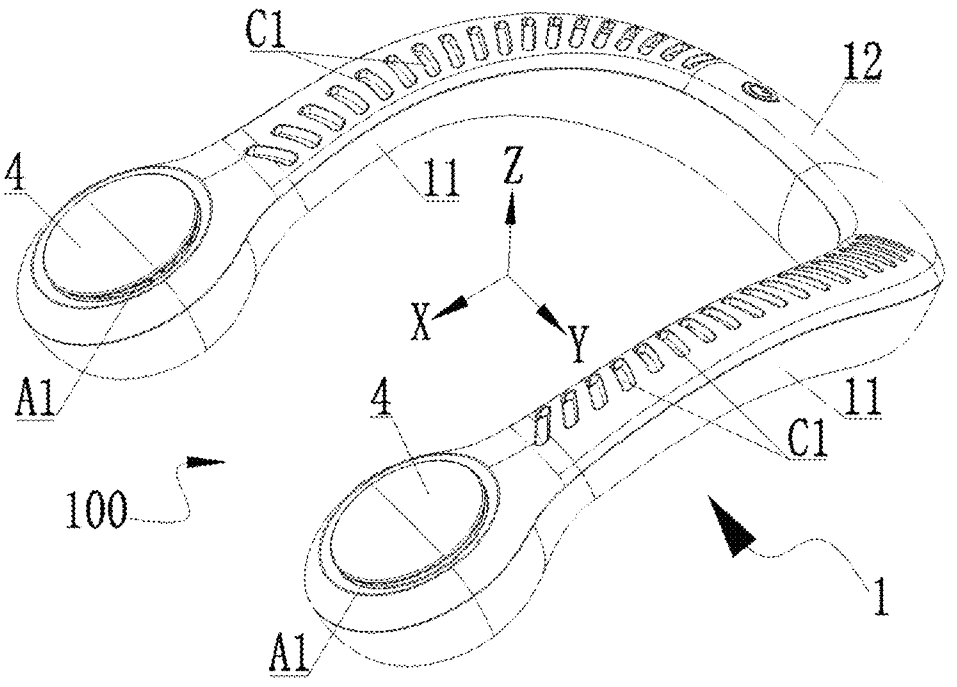
FIG. 58 is a schematic view of a neck fan according to a first embodiment of the present disclosure.
Figure 59:
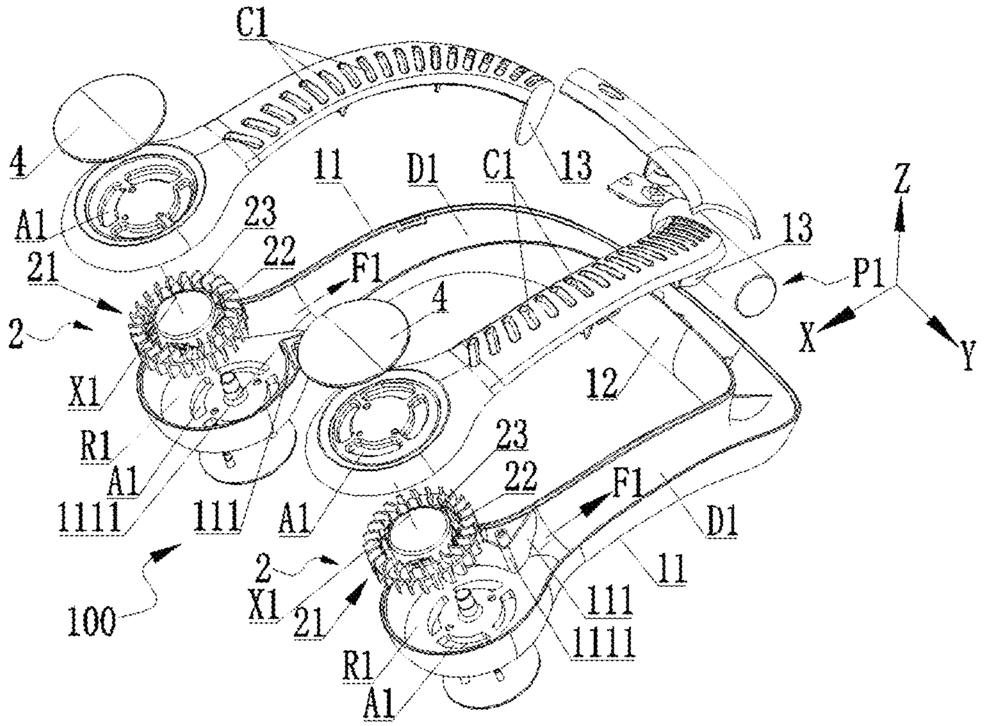
FIG. 59 is an exploded view of the neck fan according to the first embodiment of the present disclosure.
Figure 60:
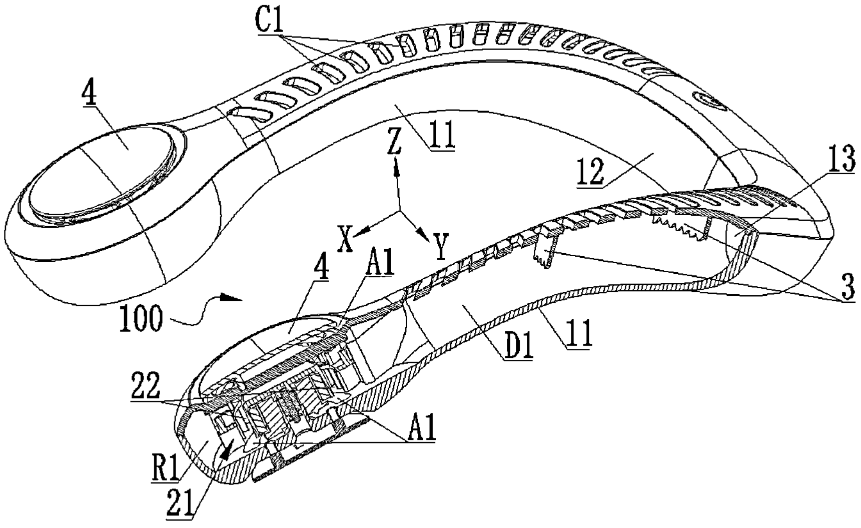
FIG. 60 is a cross section view of the neck fan according to the first embodiment of the present disclosure.

As shown in FIGS. 58-60, the neck fan 100, according to a first embodiment of the present disclosure, may include a shell 1. The shell 1 may include two first portions 11 and a second portion 12 connected to the two first portions 11. The two first portions 11 may be symmetrically disposed at two opposite sides of the second portion 12. The shell 1 (in other words, one of the two first portions 11) may be arranged with a first air inlet portion A1 and a first air outlet portion C1 and may define a receiving chamber R1 and an air duct D1. The neck fan 100 may further include a fan assembly 2. The fan assembly 2 may be received in the receiving chamber R1. The fan assembly 2 may be configured to drive the external air to flow through the first air inlet portion A1, further flow along the receiving chamber R1 and the air duct D1, and to flow out of the neck fan through the first air outlet portion C1. The fan assembly 2 may include a fan 21 and a motor driving the fan 21 to rotate. The motor may drive the fan 21 to rotate around a rotation shaft. A central axis of the rotation shaft X1 may be perpendicular to an orthographic projection of the first air inlet portion A1. When the neck fan 100 is worn to the user, the second portion 12 may correspond to the back the user's neck. The two first portions 11 may correspond to a left neck and a right neck respectively and correspond to a front of the user's chest. The two first portions 11 may extend from the second portion 12, extending upwardly and front-wardly, and further extending downwardly towards the user's chest. Along extending directions of the two first portions 11, the two first portions 11 may partially correspond to the user's shoulders. Further, along a gravitational direction, a wider face of the first portion 11 and a wide face of the second portion 12 contact the user. In this way, neck fan 100 may lay on the user's shoulders, which may be ergonomically friendly, allowing the user to be more comfortable when wearing the neck fan. It shall be understood that, shapes of the first portion 11 and the second portion 12 may not be limited by the above embodiments, as long as the neck fan 100 may be worn to around the user's neck. In other embodiments, one first portion 11 may be used independently. One first portion 11 may serve as a hand-held fan, a clamping fan, a fan worn to other portions of the user (such as a wrist).

Figure 61:
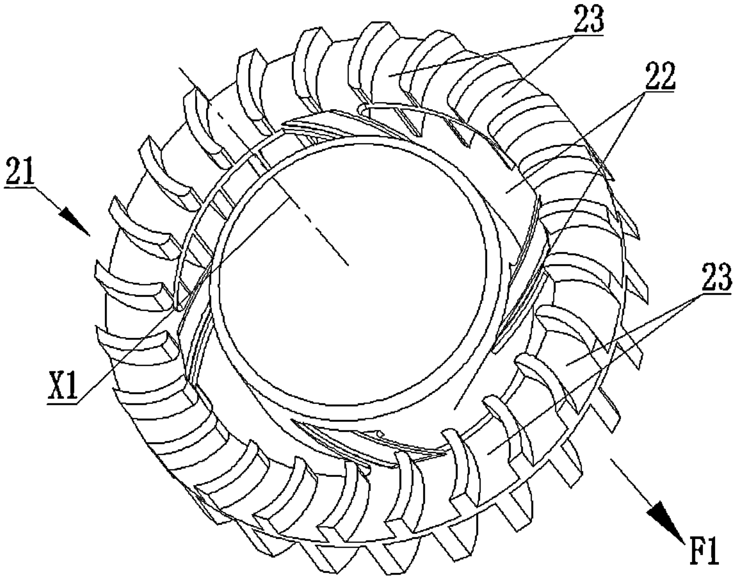
FIG. 61 is a schematic view of a fan of the neck fan according to the first embodiment of the present disclosure.

As shown in FIGS. 59-61, the fan 21 may have a second air inlet portion 22 and a second air outlet portion 23. The air may flow past the first air inlet portion A1, the second air inlet portion 22, the second air outlet portion 23, and the air duct D1, and the air may flow out of the neck fan through the first air outlet portion C1. At least a portion of the second air inlet portion 22 may extend through the fan 21. The central axis X1 of the rotation shaft may be perpendicular to the orthographic projection of the second air inlet portion 22. The air may flow to leave the second air outlet portion 23 along a first direction F1 (indicated by the arrow shown in FIG. 63). The first direction F1 may be perpendicular to the central axis X1 of the rotation shaft. In other words, the motor drives the fan to rotate, generating a rotation plane. The first portion 11 may include a first wall defining the air outlet and a second wall defining the air inlet. The first wall and the second wall may be arranged on a same side of the rotation plane.

In the present embodiment, the fan 21 may be a turbine fan. The turbine fan may occupy a relatively small space but generate a proper amount of air. Therefore, a space utilization rate may be high. Further, for the turbine fan, the air is taken in along an axial direction, and the air is output along a radial direction. The fan 21 may lay on the shoulders, and the central axis of the rotation shaft is perpendicular to the orthographic projection of the first air inlet portion A1. The shell 1 is arranged with two first air inlet portions A1 on two opposite sides of the fan 21. The fan 21 may define the air inlets in an upper side and a lower side of the fan 21. That is, the air may be taken in from the upper side and the lower side at the same time. In this way, an air inlet demand of the fan 21 may be satisfied. Further, intaking the air from the upper side and the lower side at the same time may not intake the hair at left and right sides of the fan, ensuring the user's safety. In other embodiments, the fan 21 may not be limited to the turbine fan, but may be a fan in other types, as long as the fan can be driven by the motor to generate the wind.

As shown in FIGS. 59 and 60, the receiving chamber R1 is defined in an end of the first portion 11 away from the second portion 12. That is, the fan assembly 2 is arranged at the end away from the second portion 12, such that a relatively large range of regions may be available to correspondingly arrange the first air inlet portion A1. The second portion 12 is configured to receive an electronic control assembly P1. The electronic control assembly P1 may include a battery, a circuit board and a switch, and the like. A partition 13 may be arranged inside the shell 1 to separate the first portion 11 from the second portion 12. The air duct D1 is defined between the receiving cavity R1 and the partition plate 13. The partition plate 13 prevents the flowing air from affecting operation of the electronic control assembly P1, ensuring the safety of using the neck fan 100. In addition, the air duct D1 is defined only in the first portion 11, such that the generated wind may not be consumed in an excessively long air duct D1, allowing the air flowing out of the first air outlet portion C1 to be more stable and comfortable. It shall be understood that wires may be arranged between the electronic control assembly P1 and the motor, such that the electronic control assembly P1 may supply power to the motor, and such the structure may be available in the art and will not be described in detail herein.

In some embodiments, the shell 1 may not be arranged with the partition plate 13. The electronic control assembly P1 may be arranged out of the shell 1. The air duct D1 may further extend to the second portion 12. Arranging the electronic control assembly P1 out of the shell 1 allows the neck fan 100 to be more slim. Similarly, the receiving chamber R1 may be defined in other components of the shell 1, such as in the second portion 12. Only one fan assembly 2 may be arranged. The present disclosure does not limit the number of the fan assemblies 2, as long as the fan assembly 2 can drive the external air into the shell 1, transfer the air into a wind, and drive the wind to flow out of the neck fan from the first air outlet C1.

As shown in FIGS. 58-60, the central axis of the rotation shaft is perpendicular to the orthographic projection of the first air outlet portion C1. In detail, the first air outlet portion C1 extends through the first portion 11 and extends diagonally upwards. When the neck fan 100 is worn, the first air outlet portion C1 corresponds to a side of the neck and blows the air in an upward direction. In this way, the air from the first air outlet portion C1 does not flow directly towards the neck, improving the user's experience. The position of the first air outlet portion C1 is not limited by the present disclosure. The central axis of the rotation shaft may alternatively be parallel to the orthographic projection of the first air outlet portion C1. For example, the first air outlet portion C1 may be arranged on a side of the first portion 11 near the user's neck. Alternatively, an angle may be formed between the central axis of the rotation shaft and the orthographic projection of the first air outlet portion C1.

As shown in FIG. 60, in the air duct D1, the wind guide member 3 extends from the inner wall of the first portion 11 where the first air outlet portion C1 is arranged in a direction away from the first air outlet portion C1. In this way, the air guide 3 may guide a portion of the air to flow out of the neck fan from the first air outlet portion C1 at a front side of the neck fan, and at the same time, the air guide 3 may guide the remaining air to flow out of the neck fan from the first air outlet portion C1 at a rear of the neck fan. In the present embodiment, two wind guide portions 3, which are spaced apart from each other, may be received in the air duct D1 in a direction of extending from the receiving chamber R1 and the second portion 12. A slope difference and a height difference may be present between the two wind guide portions 3. In this way, the air flowing out of the first air outlet portion C1, which is divided by the two wind guide portions 3, may be uniform, improving the user's experience. The number of wind guide portions 3 is not limited by the present disclosure, as long as the air is evenly flowing through each part of the first air outlet portion C1, which is divided by the wind guide portions 3. An edge of a free end of the wind guide portion 3 may be wavy or serrated to reduce the wind noise, and the shape of the edge shall not be limited by the present disclosure.

Figure 62:
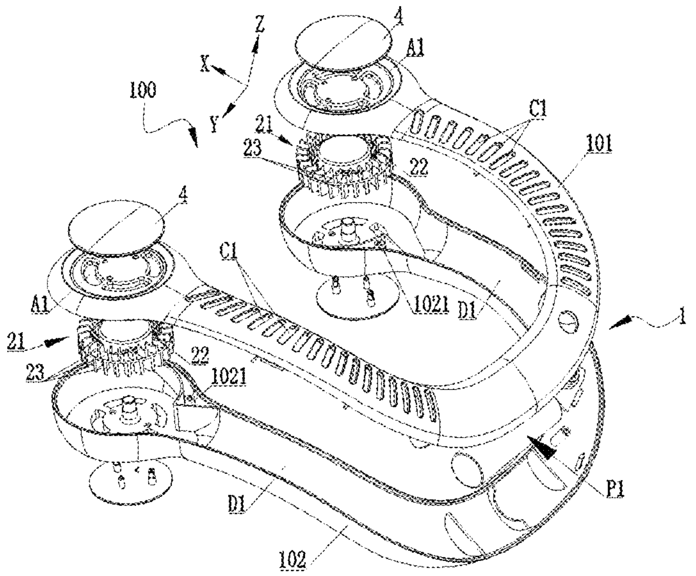
FIG. 62 is an exploded view of the neck fan according to the first embodiment of the present disclosure from another view angle.

As shown in FIGS. 58-59 and 62, the shell 1 includes a first shell 101 and a second shell 102 that can be engaged with each other. A first engaging portion may be arranged inside the first shell 101, and a second engaging portion 1021 may be arranged inside the second shell 102. The first engaging portion and the second engaging portion 1021 may be snapped or embedded or bolted or magnetically connected to each other, based on the actual situation. A connection manner between the first engaging portion and the second engaging portion 1021 is not limited by the present disclosure. A fan partition plate 111 extends from the inner wall of the first portion 11 and surrounds a part of the fan 21. A space cooperatively defined between the fan partition plate 111 and the shell 1 may be suitable to receive the second engaging portion 1021. Further, the fan partition plate 111 extends towards a width direction of the receiving chamber R1 to form a corner 1111, and the corner 1111 may serve as a turning tongue of a turbine fan. The corner 11111 formed from the fan partition plate 111 reduces a width of the air outlet, resulting in a more effective air flowing.

As shown in FIGS. 58-60, an air inlet cover 4 is arranged on an outer side of the first air inlet portion A1, prevent the rain or external dust from entering the shell 1 and affecting operation of the fan assembly 2. A gap is defined between the air inlet cover 4 and the first air inlet portion A1 facilitating the air to enter the shell 1. The air inlet cover 4 further prevents the hair from being sucked when the neck fan is operating, ensuring the user's safety.

Figure 63:
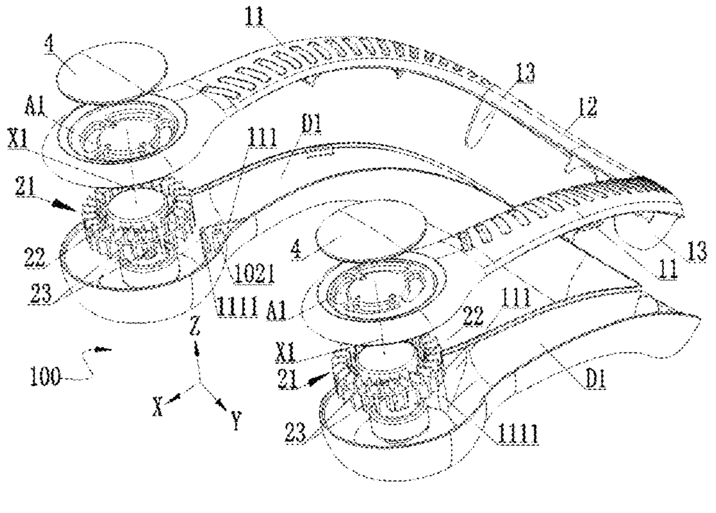
FIG. 63 is an exploded view of a neck fan according to a second embodiment of the present disclosure from another view angle.

As shown in FIG. 63, a second embodiment of the neck fan 100 of the present disclosure is provided. In the present embodiment, the shell 1 is arranged with one first air inlet portion A1 corresponding to only one of two opposite sides of the fan 21. In detail, the shell 1 is arranged with one first air inlet portion A1 corresponding to an upper side of the fan 21. In this way, the amount of air intaking may be reduced, but the amount of air flowing out of the neck fan may be more suitable for people who have a low requirement about the amount of air flowing but require the air flowing to be comfortable. Alternatively, the shell 1 may be arranged with one first air inlet portion A1 corresponding to a lower side of the fan 21 only. Other structure and properties of the present embodiment may be referred to the above first embodiment and will not be repeated here.

Figure 64:
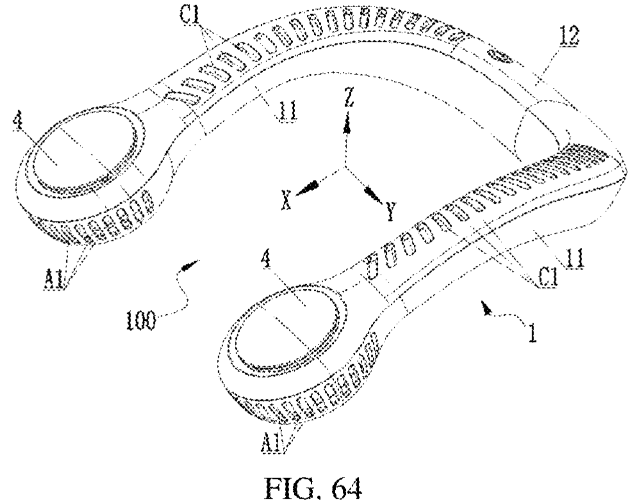
FIG. 64 is a schematic view of a neck fan according to a third embodiment of the present disclosure from another view angle.
Figure 65:
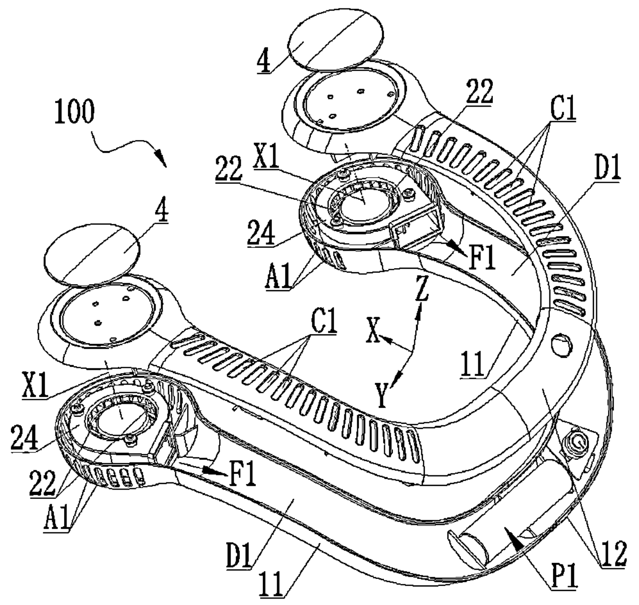
FIG. 65 is an exploded view of the neck fan according to the third embodiment of the present disclosure from another view angle.
Figure 66:
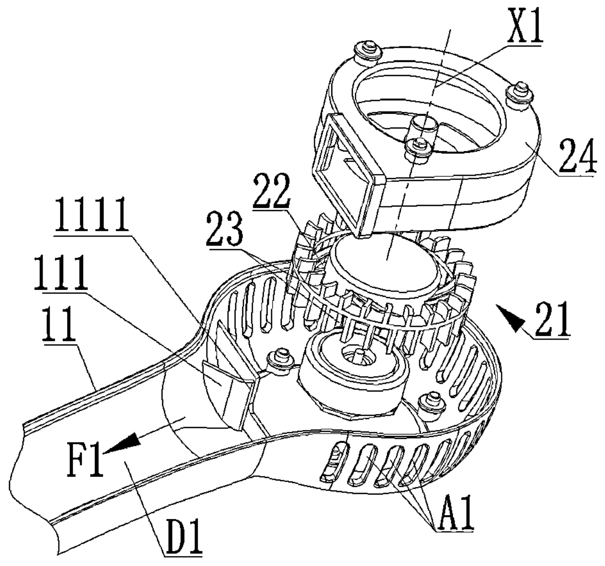
FIG. 66 is an exploded view of a portion of the neck fan according to the third embodiment of the present disclosure from another view angle.

As shown in FIGS. 64-66, a third embodiment of the neck fan is shown. In the present embodiment, the shell 1 is arranged with the first air inlet portion A1 corresponding to a radial outer side of the fan 21. The central axis X1 of the rotation shaft is parallel to the orthographic projection of the first air inlet portion A1. The fan 21 is arranged at the end of the first portion 11 away from the second portion 12. The first air inlet portion A1 may be arranged on a large half circle of the end of the first portion 11. In this way, a relatively large area may be available to arrange the first air inlet portion A1, increasing the air intaking volume and a range for intaking the air. At the same time, since the fan 21 is the turbine fan, the fan may intake the air along the axial direction and outputs the wind along the radial direction. In order to avoid the air coming out of the second air outlet portion 23 of the fan 21 from colliding with the air entering the neck fan from the first air inlet portion A1 (which corresponds to radial outside of the fan), a fan shell 24 is arranged on the outside of the fan 21 to guide the air inlet and the air outlet of the fan 22. In this way, the air inlet and the air outlet may be achieved smoother. Other structures and properties of the present embodiment may be the same as those of the first embodiment and will not be repeated here.

In other embodiments, a first angle is present between the central axis X1 of the rotation shaft and the orthographic projection of the first air inlet portion A1. The first air inlet portion A1 and the first air outlet portion C1 may be arranged at other positions, as long as the first angle can be generated between the central axis X1 of the rotation shaft and the first air inlet portion A1, a second angle can be generated between the central axis X1 of the rotation shaft and the first air outlet portion C1, and each of the first angle and the second angle is in a range of 0-90 degrees (including the 0 degree and the 90 degrees). When the air inlet of the first air inlet portion A1 conflicts with the air outlet of the second air outlet portion 23 of the fan 22, the fan shell 24 may be arranged at the outside of the fan 22 to guide the air inlet and the air outlet of the fan 22. Compared to the art, positions of the neck fan 100 in the present embodiment available for arranging the first air inlet portion A1 and the second air outlet portion C1 may be increased.

FIGS. 67-73 show a neck fan according to another embodiment of the present disclosure.

Figure 67:
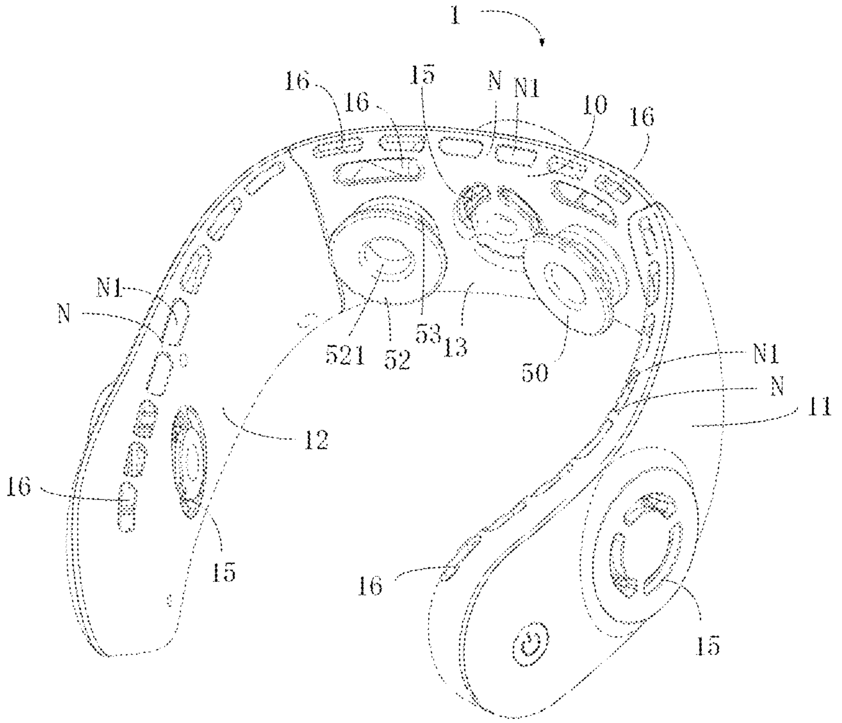
FIG. 67 is a schematic view of a neck fan according to an embodiment of the present disclosure.
Figure 68:
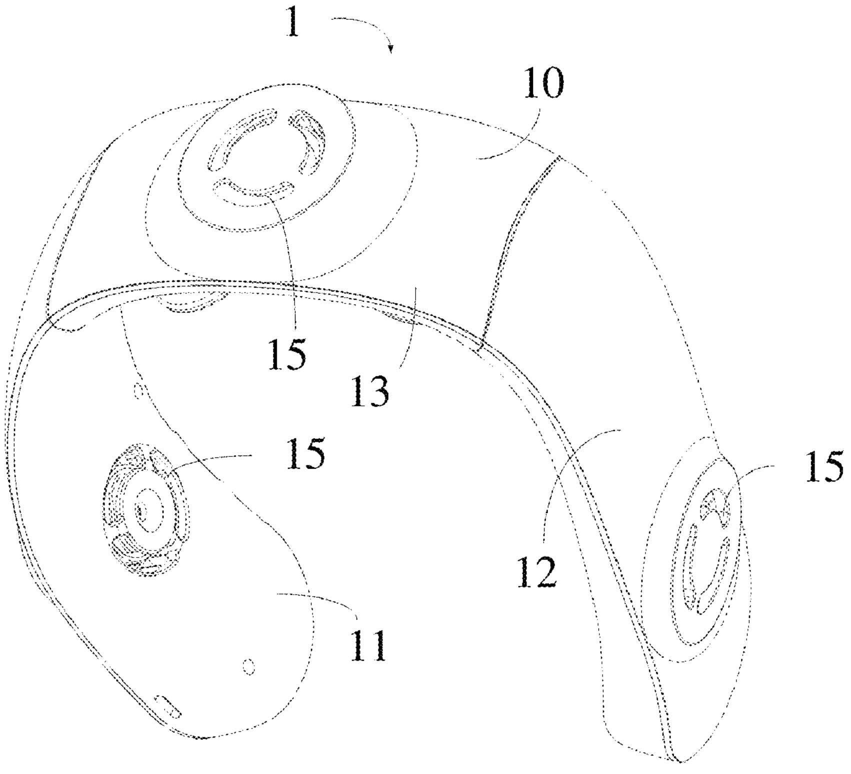
FIG. 68 is a schematic view of the neck fan shown in FIG. 67 from another view angle.

As shown in FIGS. 67 and 68, FIG. 67 is a schematic view of a neck fan according to an embodiment of the present disclosure, and FIG. 68 is a schematic view of the neck fan shown in FIG. 67 from another view angle. The neck fan 1 includes a shell 10, serving as a neck piece that hangs around the user's neck. When the neck fan is worn at the neck, the user's hands may be released and may perform other operations while using the neck fan. It shall be understood that, in the present embodiment, in order to allow the neck fan 1 to be worn more closely to the neck, the shell 10 may be curved.

Figure 69:
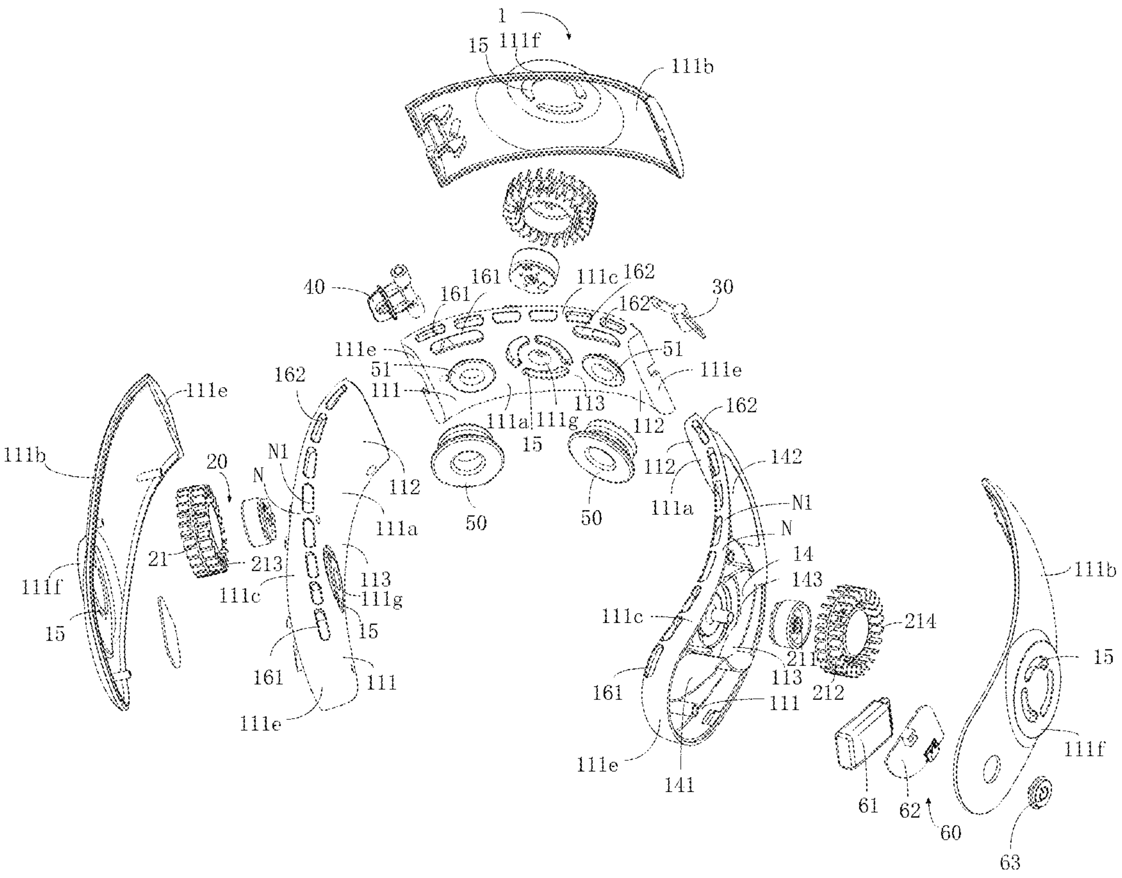
FIG. 69 is an exploded view of the neck fan shown in FIG. 67.
Figure 70:
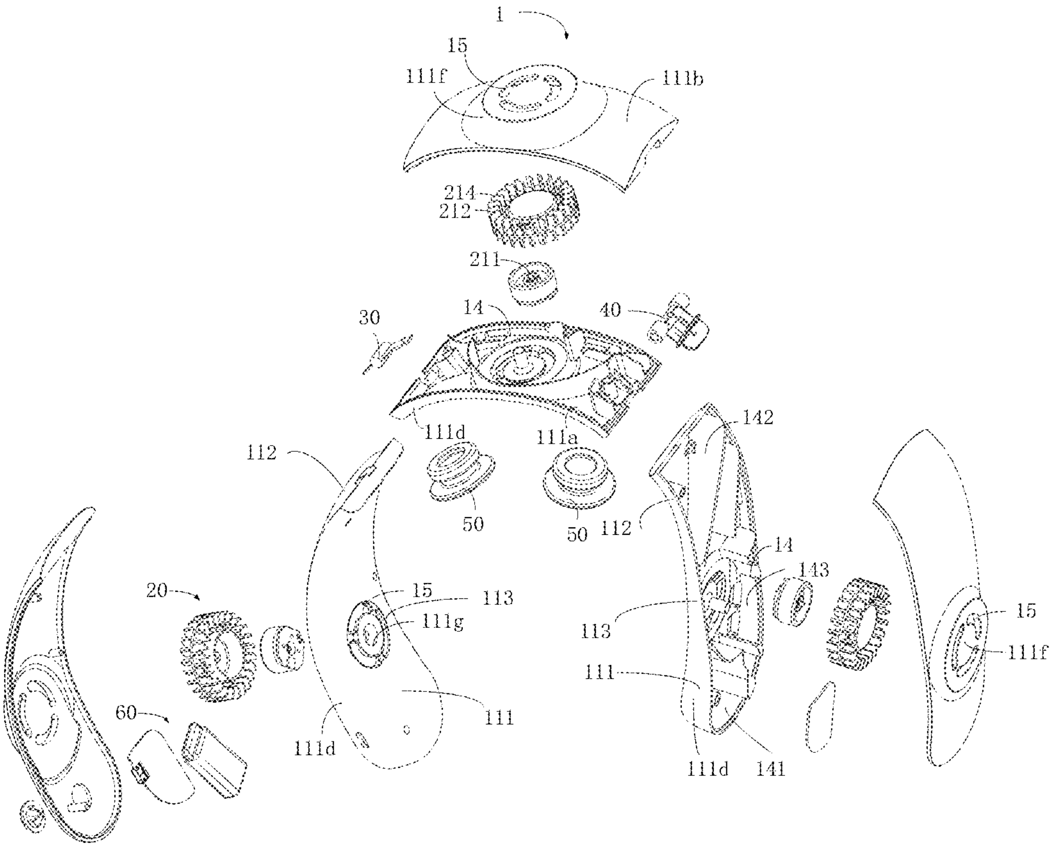
FIG. 70 is an exploded view of the neck fan shown in FIG. 68.

As shown in FIGS. 69 and 70, FIG. 69 is an exploded view of the neck fan shown in FIG. 67, and FIG. 70 is an exploded view of the neck fan shown in FIG. 68. In the present embodiment, the neck fan 1 may further include at least three fan assemblies 20 arranged inside the shell 10. The shell 10 includes a first shell 11, a second shell 12 and a third shell 13. The first shell 11 and said second shell 12 may be configured to hang near two opposite sides of the user's neck respectively. The third shell 13 may be connected to the first shell 11 and the second shell 12 and disposed between the first shell 11 and the second shell 12. Each of the first shell 11, the second shell 12 and the third shell 13 defines a receiving cavity 14, an air inlet 15 communicated with the receiving cavity 14 and an air outlet 16 communicated with the receiving cavity 14. One fan assembly 20 may be received in each of the receiving cavity 14 of the first shell 11, the receiving cavity 14 of the second shell 12 and the receiving cavity 14 of the third shell 13, and may be configured to guide the air to flow from the air inlet 15 to the air outlet 16 respectively. It shall be understood that the first shell 11, the second shell 12 and the third shell 13 of the neck fan 1 may be connected to form an arc, such that the neck fan may fit curvature of the user's neck and may be easily worn. Further, the first shell 11 and the second shell 12 are disposed at two opposite sides of the user's neck, weights of the two sides of the neck fan may be balanced, the neck fan may be worn stably and not easily fall off from the user's neck. In addition, receiving one fan assembly 20 in the receiving cavity 14 of the third shell 13 allows the neck fan 1 to blow out the wind towards the back of the neck, and airflows may surround the user's neck and may flow uniformly, such that the user's neck may be cooled quickly, improving the user's experience.

According to the neck fan 1 in the above embodiment, the arc-shaped shell 10 allows the neck fan 1 to hang around the neck, the neck fan may blow the wind directly towards the neck and face, the user may be cooled quickly, improving the user's experience. In addition, arranging three fan assemblies 20 may increase the air out-flowing efficiency and increase the air output volume, such that a large area can be covered by the air out of the neck fan, further enabling the user to be cooled quickly, improving the user's experience. The three fan assemblies 20 are received in receiving cavities 14, and therefore, the hair or foreign matters may not be caught in the fan assemblies 20, ensuring the user's safety while using the neck fan 1.

As shown in FIGS. 67-70, at least one of the first shell 11, the second shell 12 and the third shell 13 includes a first portion 111, a second portion 112 and a third portion 113. The third portion 113 is connected to the first portion 111 and the second portion 112 and is disposed between the first portion 111 and the second portion 112. The receiving cavity 14 extends from the first portion 111 through the third portion 113 to the second portion 112. The receiving cavity 14 includes a first sub-cavity 141 in the first portion 111, a second sub-cavity 142 in the second portion 112 and a third sub-cavity 143 in the third portion 113. The first sub-cavity 141, the second sub-cavity 142 and the third sub-cavity 143 are communicated with each other. The fan assembly 20 is received in the third sub-cavity 143 of the third portion 113 and is configured to guide the air from the air inlet 15 to the air outlet 16.

It shall be understood that, in the neck fan 1 of the present embodiment, the first shell 11 and the second shell 12, which are disposed at two opposite sides of the user's neck, may be structurally symmetrical. Each of the first shell 11, the second shell 12 and the third shell 13 may include the first portion 111, the second portion 112, and the third portion 113. One fan assembly 20 is arranged inside each of the third portion 113 of the first shell 11 and the third portion 113 of the second shell 12. While the neck fan 1 is operating, the fan assemblies 20 arranged at the two opposite sides of the user's neck may respectively guide the air from the air inlet 15 of the first shell 11 to flow to the air outlet 16 of the first shell 11 and guide the air from the air inlet 15 of the second shell 12 to flow to the air outlet 16 of the second shell 12. In addition, one fan assembly 20 is arranged in the third portion 113 of the third shell 13 and is configured to guide the air from the air inlet 15 of the third shell 13 to flow to the air outlet 16 of the third shell 13. Since the receiving cavity 14 is defined in each of the first shell 11, the second shell 12, and the third shell 13, and the fan assembly 20 is received in the third sub-cavity 143 of the third cavity 14 of each of the first shell 11, the second shell 12, and the third shell 13, the air flowing out of the first shell 11, the air flowing out of the second shell 12, and the air flowing out of the third shell 13 may be spaced apart from each other and may not interfere with each other. Therefore, the loss in the air out flowing may be reduced, and the efficiency of air flowing out of the neck fan 1 may be improved.

As shown in FIGS. 67 and 69, the air outlet 16 includes a first air outlet 161 defined in the first portion 111 and communicated with the first sub-cavity 141 and a second air outlet 162 defined in the second portion 112 and communicated with the second sub-cavity 142. The third portion 113 includes a wind-free region N. The wind-free region N is disposed between the first air outlet 161 and the second air outlet 162 and corresponds to a position where the fan assembly 20 is arranged. It shall be understood that, in the present embodiment, the wind-free region N does not define any air outlet, but defines a blind hole Ni, which does not allow any air to flow through. Further, the wind-free region N corresponds to the fan assembly 20, such that the wind generated by the fan assembly 20 may flow towards the first air outlet 161 and the second air outlet 162, which locate at two opposite sides of the fan assembly 20. In this way, the air flowing efficiency may be increased, the air may flow out of the neck fan more softly and more comfortably. In some embodiments, the wind-free region N may be a region without any hole. Alternatively, the wind-free region N may define openings, and a blocking plate may be arranged to block the openings, preventing the air from flowing through the openings, such that the wind-free region N is formed. According to the present embodiment, the wind-free region N separates the first air outlet 161 and the second air outlet 162, such that the air may be distributed to two sides, the air may not be concentrated towards air outlets on one side, and therefore, the air volume may not be excessively high on one side, and an air blowing time may be not be excessively long on one side, the user may be comfortable, and the user's safety while using the neck fan 1 may be improved.

As shown in FIGS. 69 and 70, each of the first portion 111, the second portion 112 and the third portion 113 includes an inner plate 111*a*, an outer plate 111*b*, a first connection plate 111*c*, and a second connection plate 111*d*. The inner plate 111*a* is disposed near the neck. The outer plate 111*b* is disposed opposite to the inner plate 111*a*. The first connection plate 111*c* is connected to the inner plate 111*a* and the outer plate 111*b* and is disposed near the head. The second connection plate 111*d* is disposed opposite to the first connection plate 111*c*. The air inlet 15 is defined in at least one of the inner plate 111*a* of the third portion 113 and the outer plate 111*b* of the third portion 113. The first air outlet 161 is defined in the first connection plate 111*c* of the first portion 111. The second air outlet 162 is defined in the first connection plate 111*c* of the second portion 112. The wind-free region N is disposed on the first connection plate 111*c* of the third portion 113. Furthermore, the wind-free region N of the present embodiment may correspond to the user's ears and a middle of the neck, preventing the wind noise generated when the wind blows directly to the ears, and preventing the neck from being uncomfortable when the wind blows directly to the neck. Further, hearing of the user may be protected, improving the user's experience. In the present embodiment, in order to allow the fan assembly 20 to blow the air towards the user's head to cool the user quickly and to improve the user's experience, the first air outlet 161 may be defined in the first connection plate 111*c* of the first portion 111, and the second air outlet 162 may be defined in the first connection plate 111*c* of the second portion 112. For the third shell, the first air outlet 161 may be defined in the inner plate 111*a* of the first portion 111, and the second air outlet 162 may be defined in the inner plate 111*a* of the second portion 112.

In some embodiments, in order to further increase the air flowing volume and an area covered by the air flowing out of the neck fan, in addition to defining the first air outlet 161 in the first connection plate 111*c* of the first portion 111 and defining the second air outlet 162 in the first connection plate 111*c* of the second the 112, the first air outlet 161 may further be defined in at least one of the inner plate 111*a* and the second connection plate 111*d* of the first portion 111, and the second air outlet 162 may further be defined in at least one of the inner plate 111*a* and the second connection plate 111*d* of the second portion 112. According to the present embodiment, the first air outlet 161 is defined in the first connection plate 111*c* of the first portion 111, and the second air outlet 162 is defined in the first connection plate 111*c* of the second portion 112. In this way, the fan assembly 20 is disposed located between the first air outlet 161 and the second air outlet 162. The fan assembly 20 may drive the air from the air inlet 15 to flow along to opposite sides of the fan assembly 20 to reach the first air outlet 161 and the second air outlet 162. The air flowing out of the first air outlet 161 and the second air outlet 162 do not interfere each other, reducing the loss of the air while outputting the air out of the neck fan. In addition, the air inlet 15 is defined in the inner plate 111*a* of the third portion 113 and the outer plate 111*b* of the third portion 113. In this way, the air intaking through the air inlet 15 does not interfere the air flowing out of the neck fan through the first air outlet 161 and the second air outlet 162. Further, circulation of intaking the air and outputting the air may be achieved, the efficiency of the air flowing out of the neck fan 1 may be improved.

As shown in FIGS. 67-70, the air inlet 15 is defined in the inner plate 111*a* of the third portion 113 and in the outer plate 111*b* of the third portion 113. The outer plate 111*b* of the third portion 113 includes a first protrusion 111*f* protruding from the outer plate 111*b* away from the user's neck. The first projection 111*f* defines a plurality of air inlets 151, and the plurality of air inlets 151 may be arranged as a circle. The inner plate 111*a* of the third portion 113 includes a second protrusion 111*g* protruding away from the user's neck. A plurality of air inlets 152 are defined and arranged as circle at a periphery of the second protrusion 111*g*. In some embodiments, the air inlets 15 may be defined in at least one of the inner plate 111*a* of the first portion 111, the outer plate 111*b* of the first portion 111, the inner plate 111*a* of the second portion 112, and the outer plate 111*b* of the second portion 112. In the present embodiment, the air inlets 15 are defined in the inner plate 111*a* of the third portion 113 and the outer plate 111*b* of the third portion 113. In this way, the air inlets 15 may correspond to the fan assembly 20, preventing the wind stifling effect caused when the air inlet 15 is defined only in the inner plate 111*a* or only in the outer plate 111*b*. The air may fluently flow all the way through the air inlet 15, the air outlet 16 and the air duct communicating with the air inlet 15 and the air outlet 16. In this way, the air may flow fluently, and the wind noise may be reduced. In the present embodiment, the air inlet 15 is defined in the inner plate 111*a* of the third portion 113 and the outer plate 111*b* of the third portion 113, such that the amount of the air taken in from the fan assembly 20 may be increased, and the efficiency of the air flowing out of the neck fan 1 may be improved.

Figure 71:
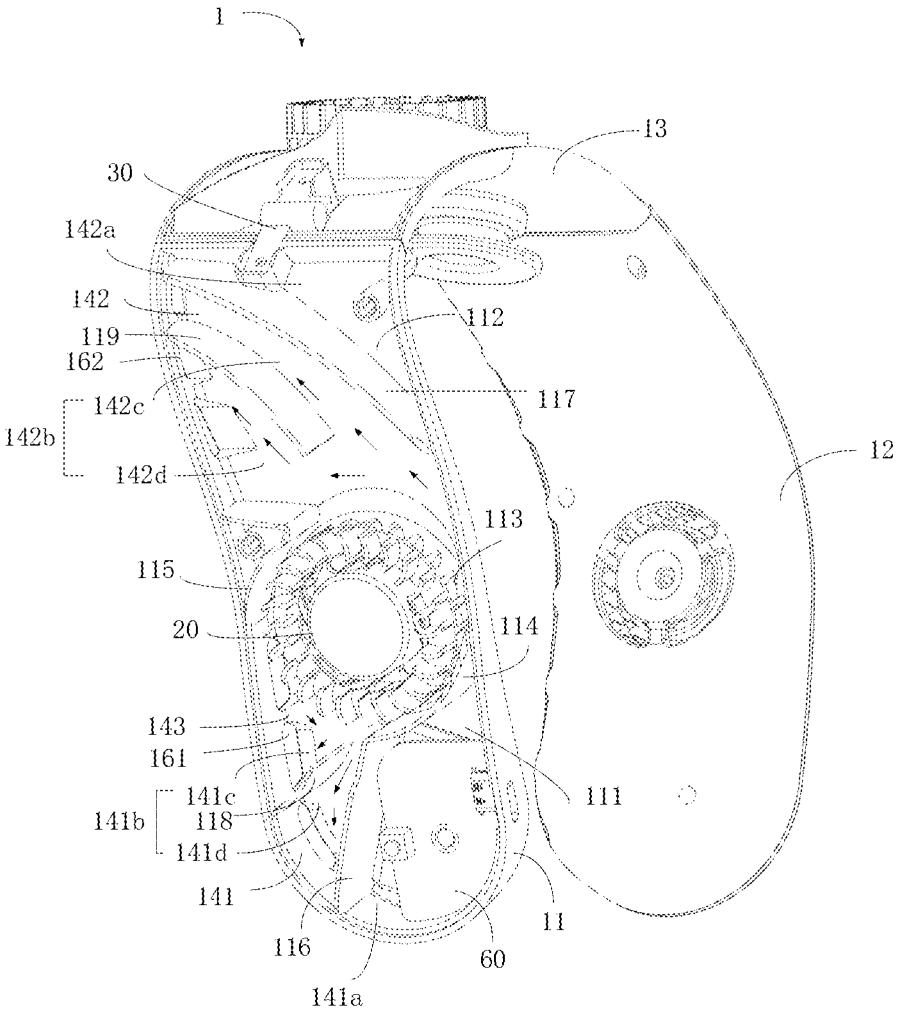
FIG. 71 illustrates an inside of a first portion of the neck fan shown in FIG. 67.

As shown in FIG. 71, FIG. 71 illustrates an inside of a first portion of the neck fan shown in FIG. 67. In order to reduce the air flowing loss and increase the air out flowing efficiency, in some embodiments, at least one of the first shell 11, the second shell 12 further includes a first partition portion 114, a second partition portion 115, a first air guide portion 116, and a second air guide portion 117. The first partition portion 114 is at least partially received in said first sub-cavity 141 and covers a side of the fan assembly 20 near the user's face and the first portion 111. The second partition portion 115 covers a periphery of the fan assembly 20 and is opposite to the first partition portion 114. The first air guide portion 116 is connected to the first partition portion 114 and is received in the first sub-cavity 141. The second air guide portion 117 is received in the second sub-cavity 142. The first air guide portion 116 divides the first sub-cavity 141 into a first receiving space 141*a* and a first air duct 141*b* communicated with the first outlet 161 of the first portion 111. The second air guide portion 117 divides the second sub-cavity 142 into a second receiving space 142*a* and a second air duct 142*b* communicated with the second outlet 162 of the second portion 112. It shall be understood that the wind generated by the fan assembly 20 is directed to two opposite sides of the fan assembly 20 and guided by the first partition portion 114 and the second partition portion 115 respectively to flow to the first air guide portion 116 and the second air guide portion 117. Further, the air is guided by the first air guide portion 116 to flow into the first air duct 141*b* to be blown out through the first air outlet 161, and guided by the second air guide portion 117 to flow into the second air duct 142*b* to be blown out through the second air outlet 162, respectively, as indicated by arrows in FIG. 71. According to the present embodiment, the first partition portion 114 and the first air guide portion 116 are arranged, such that the first sub-cavity 141 is divided into a first receiving space 141*a* and a first air duct 141*b* communicated with the first outlet 161 of the first portion 111. The second partition portion 115 and the second air guide portion 117 are arranged, such that the second sub-cavity 142 is divided into a second receiving space 142*a* and a first air duct 142*b* communicated with the second outlet 162 of the second portion 112. The first air duct 141*b*, the second air duct 142*b* may direct the wind generated by the fan assembly 20 to flow to the first outlet 161 and the second outlet 162 respectively. In this way, loss of the airflows while blowing out the air is reduced, positions towards which the air is blown may be controlled accurately, and the efficiency of the air flowing out of the neck fan may be increased.

Figure 72:
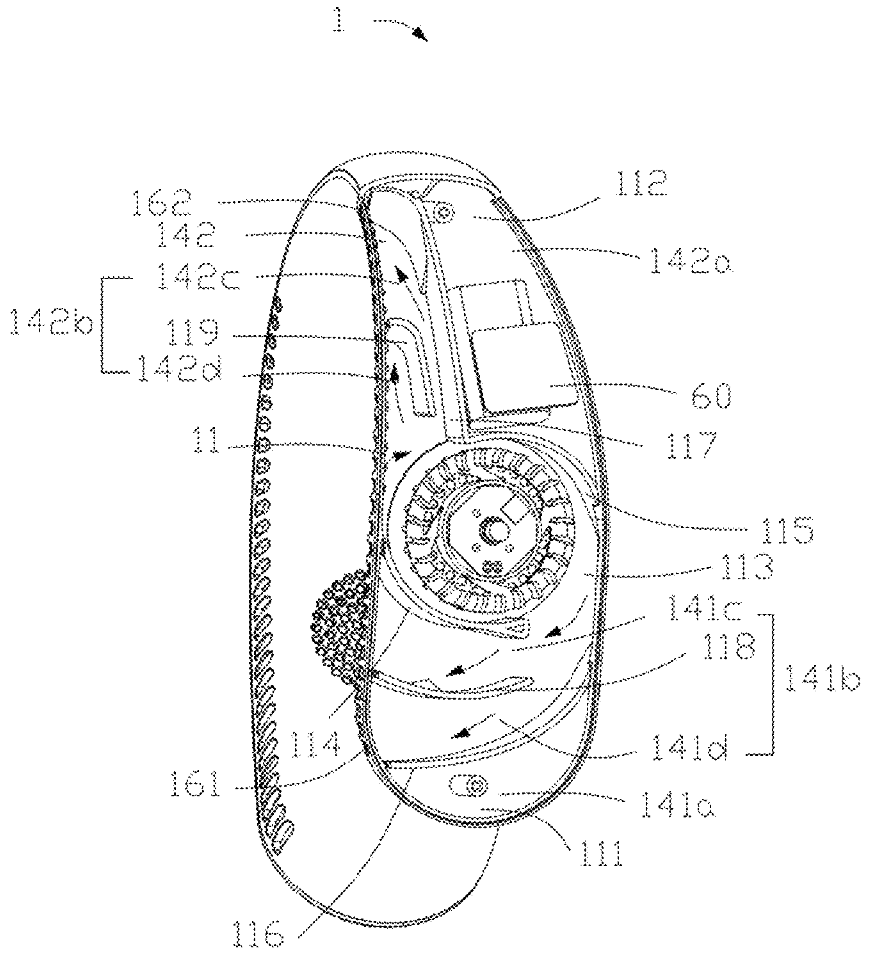
FIG. 72 illustrates an inside of a first portion of a neck fan according to another embodiment of the present disclosure.

As shown in FIG. 72, FIG. 72 illustrates an inside of a first portion of a neck fan according to another embodiment of the present disclosure. In order to reduce the air loss of the neck fan 1 and increase the air out-flowing efficiency, in some embodiments, at least one of the first shell 11 and the second shell 12 further includes the first partition portion 114, the second partition portion 115, a first air guide portion 116, and a second air guide portion 117. The first partition portion 114 is at least partially received in the third sub-cavity 143 and covers the side of the fan assembly 20 near the user's face and the first portion 111. The second partition portion 115 covers the periphery of the fan assembly 20 and is opposite to said first the first partition section 114. The first air guide portion 116 is disposed in the first sub-cavity 141. The second air guide portion 117 is disposed in said second sub-cavity 142 and connected to the second partition portion 115. The first air guide portion 116 divides the first sub-cavity 141 into a first receiving space 141*a* and a first air duct 141*b* communicated with the first outlet 161 of the first portion 111. The second air guide 117 divides the second sub-cavity 142 into a second receiving space 142*a* and a second air duct 142*b* communicated with the second outlet 162 of the second portion 112. It shall be understood that the wind generated by the fan assembly 20 is directed two opposite sides of the fan assembly 20 and is guided by the first partition portion 114 and the second partition portion 115 to the first air guide portion 116 and the second air guide portion 117, respectively. Further, the wind is guided by said first air guide portion 116 to flow into the first air duct 141*a* to further be blown out of the neck fan through the first air outlet 161, and at the same time, the wind is guided by said second air guide portion 117 to flow into the second air duct 141*b* to further be blown out of the neck fan through the second air outlet 162, as indicated by arrows in the FIG. 72. According to the present embodiment, the first partition portion 114 and the first air guide portion 116 are arranged to divide the first sub-cavity 141 into the first receiving space 141*a* and the first air duct 141*b* communicated with the first outlet 161 of the first portion 111. The second partition portion 115 and the second air guide portion 117 are arranged to divide the second sub-cavity 142 into the second receiving space 142*a* and the second air duct 142*b* communicated with the second outlet 162 of the second portion 112. The first air duct 141*b* and the second air duct 142*b* direct the wind generated by the fan assembly 20 to flow to the first outlet 161 and the second outlet 162 respectively. In this way, the loss in the air out flowing may be reduced, positions towards which the air is blown may be controlled accurately, and the efficiency of the air flowing out of the neck fan may be increased.

In some embodiments, the first air guide portion 116 received in the first sub-cavity 141 is connected to the first partition portion 114, and the second air guide portion 117 is connected to the second partition portion 115.

Further, as shown in FIGS. 71 and 72, the neck fan 1 includes a first auxiliary air guide plate 118 and a second auxiliary air guide plate 119. The first auxiliary air guide plate 118 is configured to divide the first air duct 141*b* into a first sub-duct 141*c* and a second sub-duct 141*d*. The first air duct 141*b* is communicated with a portion of a plurality of air outlets 16 of the first portion 111. The second sub-duct 141*d* is communicated with another portion of the air outlets 16 of the first portion 111. The second auxiliary air guide plate 119 is configured to divide the second air duct 142*b* into a third sub-duct 142*c* and a fourth sub-duct 142*d*. The third sub-duct 142*c* is communicated with a portion of a plurality of air outlets 16 of the second portion 112. The fourth sub-duct 142*d* is communicated with another portion of the air outlets 16 of the second portion 112. In the present embodiment, an end portion of the first auxiliary air guide plate 118 near the first air outlet 161 may be substantially perpendicular to a wall of the shell that defines the first air outlet 161, and an end portion of the second auxiliary air guide plate 119 near the second air outlet 162 may be substantially perpendicular to a wall of the shell that defines the second air outlet 162. In this way, the air is guided by the first auxiliary air guide plate 118 and the second auxiliary air guide plate 119, such that the air is blown out of the neck fan along a direction substantially perpendicular to a plane where the first connection plate 111*c* is arranged. In this way, the wind is blown to the user straightforwardly. A problem of interference between inclined air flowing may be solved, and the wind force may be maintained. According to the present embodiment, the first auxiliary air guide plate 118 divides the first air duct 141*b* into the first sub-duct 141*c* and the second sub-duct 141*d*. The second auxiliary air guide plate 119 is arranged to divide the second air duct 142*b* into the third sub-duct 142*c* and the fourth sub-duct 142*d*. In this way, the air may uniformly flow out through the first air outlet 161 and the second air outlet 162, the loss in the air out flowing may be reduced, positions towards which the air is blown may be controlled accurately, and the efficiency of the air flowing out of the neck fan may be increased.

As shown in FIGS. 69-72, the neck fan 1 further includes an electronic control assembly 60. The electronic control assembly 60 includes at least one of a battery 61, a circuit board 62 and a control button 63. At least part of the electronic control assembly 60 is received in the first receiving space 141*a* or the second receiving space 142*a*. The electronic control assembly 60 allows the user to manipulate the neck fan 1 easily. The battery 61 may further supply power to the neck fan 1 when an external power source is unavailable, such that the neck fan 1 may be portable and may be used more conveniently, and the neck fan 1 may be applied in various application scenarios. In addition, the first air guide portion 116 is connected to the first partition portion 114, and at least part of the electronic control assembly 60 is received in the first receiving space 141*a*. Alternatively, the second air guide portion 117 is connected to the second partition section 115, and at least part of the electronic control assembly 60 is received in the second receiving space 141*b*. Alternatively, the first air guide portion 116 is connected to the first partition portion 114, the second air guide portion 117 is connected to the second partition section 115, and at least part of the electronic control assembly 60 is received in the first receiving space 141*a* or the second receiving space 141*b*. Receiving at least part of the electronic control assembly 60 in the first receiving space 141*a* or the second receiving space 141*b* ensures air tightness of the first receiving space 141*a* or the second receiving space 142*a* that receives the electronic control assembly 60. In this way, external moisture, dust, and the like may be prevented from entering the neck fan through the air inlet, improving the safety of the neck fan 1.

Figure 73:
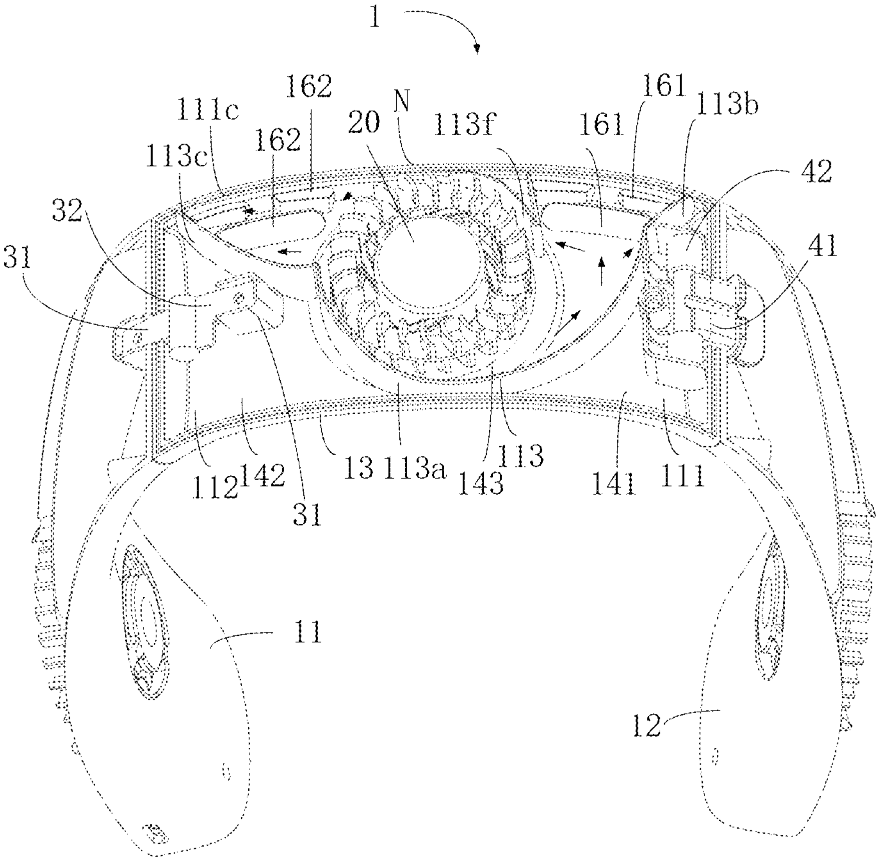
FIG. 73 illustrates an inside of a third portion of the neck fan shown in FIG. 67.

As shown in FIG. 73, FIG. 73 illustrates an inside of a third portion of the neck fan shown in FIG. 67. The third shell 13 includes a third partition plate 113*a*, a first extension portion 113*b*, a second extension portion 113*c*, and a third air guide portion 113*f*. The third partition plate 113*a* covers a side of the fan assembly 20 away from the first connection plate 111*c*. The first extension portion 113*b* is connected to an end of the third partition portion 113*a* near the first portion 111 and the first connection plate 111*c*. The second extension portion 113*c* is connected to an end of the third partition plate 113*a* near the second portion 112 and the first connection plate 111*c*. The third air guide portion 113*f* covers a side of the fan assembly 20 away from the third partition plate 113*a* and is connected to the wind-free region N. The third partition portion 113*a* extends along a curved direction. The fan assembly 20 is arranged eccentrically relative to the third partition plate 113*a*. The fan assembly 20 drives the air from the air inlet 15 to flow through the third partition portion 113*a*, the first extension portion 113*b* and the third air guide portion 113*f* to reach the first air outlet 161. The fan assembly 20 drives the air from the air inlet 15 to flow through the second extension 113*c* to reach the second air outlet 162. It shall be understood that, in the present embodiment, the air out of the fan assembly 20 is directed by the third partition portion 113*a*, the first extension portion 113*b*, and the second extension portion 113*c*, and further guided by the third air guide portion 113*f*, reaching and flowing out of the neck fan through the first air outlet 161 and the second air outlet 162, as indicated by arrows shown in FIG. 73. In this way, an air blowing effect may be ensured, and an air blowing force may be ensured. Arranging the third partition portion 113*a*, the first extension portion 113*b*, the second extension portion 113*c* and the third air guide portion 113*f* allows the air to uniformly flow out of the first air outlet 161 and the second air outlet 162 of the third shell 13. A loss in the air flowing may be reduced, positions towards which the air is blown may be controlled accurately, and the efficiency of the air flowing out of the neck fan may be increased.

Further, as shown in FIGS. 69-71, each of the first shell 11 and the second shell 12 is rotatably connected to the third shell 13. The shell 10 further includes a first connection member 30. The first connection member 30 is connected to the first shell 11 and the third shell 13 and disposed between the first shell 11 and the third shell 13. The shell 10 further includes a second connection member 40. The second connection member 40 is connected to the second shell 12 and the third shell 13 and disposed between the second shell 12 and the third shell 13. The first connection member 30 includes two first connection portions 31 and a second connection portion 32. The two first connection portions 31 are arranged inside the first shell 11 and the third shell 13 respectively, and the second connection portion 32 is connected to the two first connection portions 31. The second connection portion 32 extends through the third shell 13 and the first shell 11 and is rotatable. In this way, the first shell 11 is rotatably connected to the third shell 13. The second connection member 40 includes two third connection portions 41 and a fourth connection portion 42. The two third connection portions 41 are arranged inside the second shell 12 and the third shell 13, respectively. The fourth connection portion 42 is connected to the two third connection portions 41. The fourth connection portion 42 extends through the third shell 13 and the second shell 12 and is rotatable. In this way, the second shell 12 is rotatably connected to the third shell 13. It shall be understood that when the user is wearing the neck fan 1, the user may turn the first connection member 30 and the second connection member 40 to increase a gap between the first shell 11 and the second shell 12. The first shell 11 and the second shell 12 may be reset when relaxed. In this way, the user may easily wear the neck fan 1 around the neck.

In some embodiments, as shown in FIGS. 69 and 70, the fan assembly 20 includes a turbine fan 21. The turbine fan 21 includes a fan shaft 211 and a plurality of turbine blades 212 arranged to surround the fan shaft 211. An air flowing direction of the turbine fan 21 is perpendicular to an extending direction of the fan shaft 211. In this way, the fan may output a large air volume but occupy a small space, increasing an air out-flowing rate of the neck fan 1. Since the fan assembly 20 includes the turbine fan 21, operation noise of the neck fan 1 may be effectively reduced, and the efficiency of the air flowing out of the neck fan 1 may be improved. The plurality of turbine blades 212 include a first end face 213 and a second end face 214 arranged in the extending direction of the fan shaft 211. The first end face 213 corresponds to the inner plate 111*a* of the third portion 113, and the second end face 214 corresponds to the outer plate 111*b* of the third portion 113. The fan shaft 211 extends in a direction from the inner plate 111*a* to the outer plate 111*b*. A diameter of the turbine fan 21 is in the range of 35 mm to 45 mm. A thickness of the turbine fan 21 in the extending direction of the fan shaft 211 is in the range of 10 mm to 25 mm. A distance between the first end face 213 and the corresponding inner plate 111*a* is in a range of 1 mm to 6 mm; and/or a distance between the second end face 214 and the corresponding outer plate 111*b* is in a range of 1 mm to 6 mm. In some embodiments, the distance between the first end face 213 and the inner plate 111*a* may be 1 mm; and/or the distance between the second end face 214 and the outer plate 111*b* may be 1 mm. According to the present disclosure, the distance between the first end face 213 and the corresponding inner plate 111*a* is in the range of 1 mm to 6 mm, and/or the distance between the second end face 214 and the corresponding outer plate 111*b* is in the range of 1 mm to 6 mm; the diameter of the turbine fan 21 is in the range of 35 mm to 45 mm; and the thickness of the turbine fan 21 in the extending direction of the fan shaft 211 is in the range of 10 mm to 25 mm, the efficiency of the air flowing out of the fan assembly 20 may be improved. In some embodiments, when the distance between the first end face 213 and the inner plate 111*a* is 1 mm, and/or the distance between the second end face 214 and the outer plate 111*b* is 1 mm, the efficiency of the air flowing out of the fan assembly 20 may be optimal.

As shown in FIGS. 69 and 70, the neck fan 1 further includes a support member 50. A side of the third shell 13 near the user's neck is arranged with a mounting portion 51. The support member 50 is mounted on the mounting portion 51. In the present embodiment, two mounting portions 51 and two support members 50 are arranged, but the number shall not be limited by the present disclosure. The two mounting portions 51 are disposed at end of the third shell 13 near the first shell 11 and at end of the third shell 13 near the second shell 12, respectively. A recessed region is disposed between the two support members 50, and the air outlet 16 is defined in the recessed region. In the present embodiment, when the user is using the neck fan 1, the support members 50 may abut against two sides of the back neck to support the neck fan 1, allowing the neck fan 1 to leave a certain distance away from the user's neck. In addition, the recessed region is disposed between the two support members 50, such that each of the end of the third shell 13 near the first shell 11 and the end of the third shell 13 near the second shell 12 defines an air inlet 16. In this way, the air may flow out of the air outlet 16 and may be blown directly towards the back neck at the recessed region. The recessed region between the two support members 50 may define an air inlet 15, allowing the fan assembly 20 in the third shell 13 to intake the air. In the present embodiment, the support member 50 is arranged to support the neck fan 1 on the neck, and a gap is defined between the neck fan 1 and the neck, allowing the air to be taken in or flow out in the recessed region fluently, improving the user's experience.

As shown in FIGS. 67-69, the support member 50 includes a first support portion 53 mounted on the mounting portion 51 and a second support portion 52 connected to an end of the first support portion 53 away from the mounting portion 51. A side of the second support portion 52 near the user's neck is arranged with a recessed portion 521. The support member 50 has a support direction towards the user's neck. A diameter of the second support portion 52 perpendicular to the support direction is greater than a diameter of the first support portion 53 perpendicular to the support direction. It shall be understood that, the recessed portion 521 prevents the neck fan 1 from contacting the skin without a gap, such that the user may be comfortable when wearing the neck fan. A larger diameter of the second support portion 52 increases a contact area between the second support portion 52 and the neck, such that a certain space for movement may be provided at an outer edge, reducing a support pressure, such that the user may be comfortable.

Figure 74:
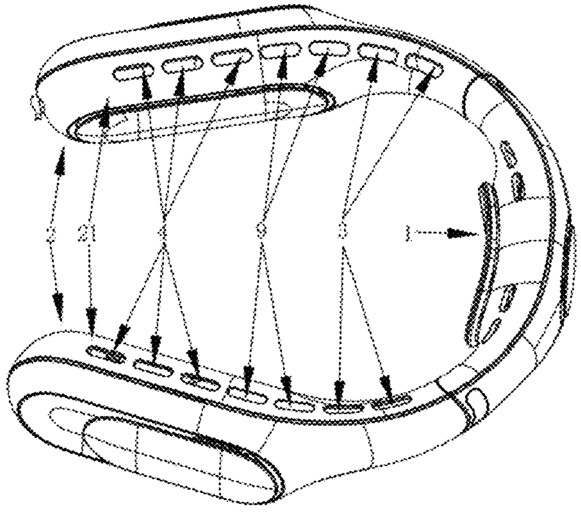
FIG. 74 is a schematic view of a neck fan according to an embodiment of the present disclosure.
Figure 75:
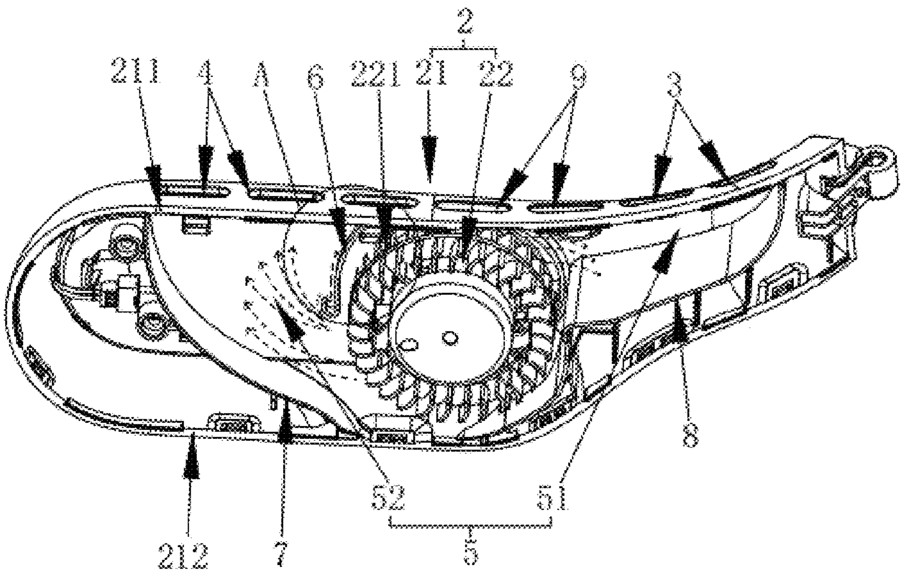
FIG. 75 is a schematic view of a fan assembly of a neck fan according to an embodiment of the present disclosure.
Figure 76:
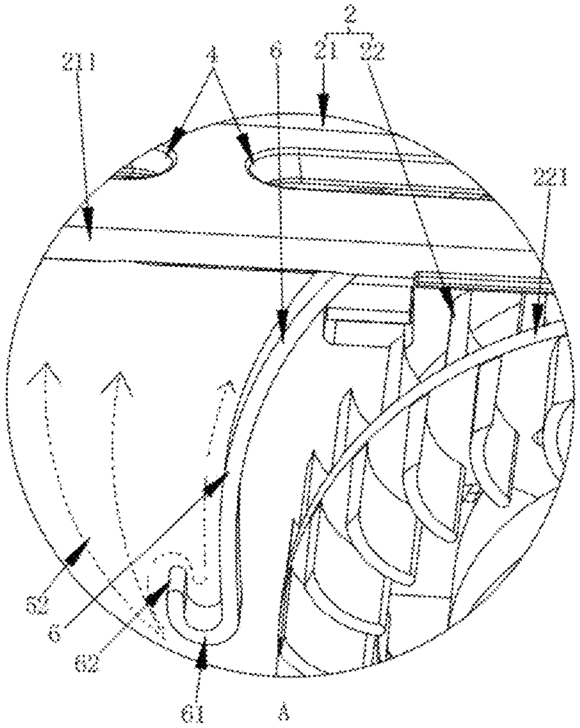
FIG. 76 is an enlarged view of a portion A shown in FIG. 75.

FIGS. 74-76 show a neck fan according to an embodiment of the present disclosure.

FIG. 74 illustrates a fan assembly and a neck fan. The neck fan includes at least two fan bodies 2 and a neck body 1 connected between the two fan bodies 2. Each of the two fan bodies 2 includes an air outlet assembly to blow out air. The two fan bodies 2 and the neck body 1 cooperatively define a neck cavity. The neck fan is worn around the neck via the neck cavity, such that the user may use the neck fan.

As shown in FIGS. 74 and 75, in an embodiment, the air outlet assembly includes a shell 21, a wind guide tongue 6 and a fan assembly 22. The shell 21 defines a receiving cavity 5. The fan assembly 22 is received in the receiving cavity 5. The wind guide tongue 6 is received in the receiving cavity 5 and surrounds the fan assembly 22. A gap is defined between the wind guide tongue 6 and the fan assembly 22. In the present embodiment, the fan assembly 22 is a centrifugal fan. The centrifugal fan intakes an airflow axially and out puts an air flow in a circumferential direction by taking a centrifugal force.

The shell 21 includes a top wall 211 and a bottom wall 212 that cooperatively define the receiving cavity 5. When the neck fan is worn, the top wall 211 is located above the bottom wall 212, the top wall 211 is located above the fan assembly 22, and the bottom wall 212 is located below the fan assembly 22. The top wall 211 defines an air outlet 3 and an air outlet 4. The air outlet 3 and an air outlet 4 communicate with the receiving cavity 5. The air outlet 3 and the fan assembly 22 are located on a first side of the wind guide tongue 6, and the air outlet 4 is located on a second side of the wind guide tongue 6, opposite to the first side. That is, the air outlet 4 is located on a side of the wind guide tongue 6 away from the fan assembly 22. The wind guide tongue 6 is disposed between the air outlet 4 and the fan assembly 22. The wind guide tongue 6 is configured to guide an air flowing direction. The airflow generated by the fan assembly 22 is guided by the wind guide tongue 6 to flow to the air outlet 3 and the air outlet 4 respectively, such that the air flows out of the neck fan from both the air outlet 3 and the air outlet 4, increasing the area covered by the air flowing out of the neck fan. The wind guide tongue 6 is further configured to control the air flowing direction. The wind guide tongue 6 controls the airflow generated by the fan assembly 22 to flow the air outlet 3 and the air outlet 4 respectively. In this way, the air may uniformly flow out of the neck fan through the air outlet 3 and the air outlet 4.

As shown in FIGS. 75 and 76, the wind guide tongue 6 is a curved plate. The curved plate surrounds the fan assembly 22. The curved plate guides the air flowing out of the fan assembly 22. The airflow guided by the curved plate flows near and along the curved plate to reach the air outlet 3 and the air outlet 4. In addition, the airflow may be guided by the wind guide tongue 6 flowing towards the air outlet 4, based on the Coanda effect, when the airflow reaches an end of the wind guide tongue 6, and when a speed of the airflow is large enough, the airflow may generate the centrifugal force. Apart of the airflow may be released from the Coanda effect of the wind guide tongue 6, and another part of the airflow continues to flow along a wall of the wind guide tongue due to the Coanda effect, and the air may further flow away from the wind guide tongue 6 to reach the air outlet 4. The curved plate further controls the air flowing direction. The curved plate controls the air flowing out of the fan assembly 22 to flow to the air outlet 3 and air outlet 4 respectively. In this way, the air may uniformly flow out of the air outlet 3 and air outlet 4.

In detail, the fan assembly 22 includes a circumference wall 221. A distance between the circumference wall 221 of the fan assembly 22 and the curved plate is 1 mm to 6 mm, preferably 2.5 mm to 4 mm. The fan assembly 22 is cylindrical. A diameter (curvature) of the curved plate is adapted with a diameter of the fan assembly 22. The diameter of the curved plate is preferably greater than or equal to the diameter of the fan assembly 22. A centre of the curved plate is located on a side of the fan assembly 22, i.e. on a first side of the curved plate.

More specifically, in an embodiment, the diameter of the curved plate is in a range from 40 mm to 60 mm, preferably 45 mm to 55 mm.

In some embodiments, the wind guide tongue 6 includes a first end and a second end opposite the first end. The first end is away from the top wall 211 of the shell 21 and is bent and extending towards the top wall 211. The first end is bent and extends away from the fan assembly 22. In more detail, the first end is bent and extending to form a semicircular shape in the direction away from the fan assembly 22. That is, the first end includes a bent portion 61 connected to the curved plate and a free end 62 disposed at an end of the bent portion. The bent portion 61 is bent, shown as a semicircle. The free end 62 is disposed at the end of the bent portion 61. The free end 62 extends towards the top wall 211. In some embodiments, the first end may be bent and extending away from the fan assembly 22 to form other suitable shapes. A radius of the bent portion 61 is in a range of 0.5 mm to 5 mm, preferably 1 mm to 4 mm. A distance from a circular center of the bent portion 61 to the top wall 211 is in a range of 6 mm to 25 mm, preferably from 15 mm to 22 mm. An extending length of the free end 62 is in a range of 0.1 mm to 1.5 mm. A gap is defined between an end of the free end 62 and the top wall 211 of the shell 21. The air flowing out of the fan assembly 22 is guided by the wind guide tongue 6 to flow from the first side and the second side of the wind guide tongue 6 to reach the air outlet 3 and the air outlet 4 respectively. The airflow directed to the second side via the first end of the wind guide tongue 6 may flow near and along the wind guide tongue 6 according to the Coanda effect. That is, the airflow follows the first end of the wind guide tongue 6 towards a region where the semicircular portion is formed and extending away from the fan assembly 22, and the air further flows to reach the air outlet 4. The second end of the wind guide tongue 6 is fixedly connected to top wall 211 of the shell 21. The second end of the wind guide tongue 6, compared to the first end, is further away from the fan assembly, and that is, along a direction from the second end to the first end, the first end is closer to the fan assembly 22.

In some embodiments, the second end of the wind guide tongue 6 may not be fixedly connected to the top wall 211, and a gap may be defined between the second end and the top wall 211 of the shell 21.

It shall be understood that, in some embodiments, the wind guide tongue 6 may be a curved plate or a plurality of curved plates spliced together. A gap may be defined between two adjacent curved plates, or two adjacent curved plates may be connected.

In some embodiments, the air outlet 3 and the air outlet 4 are both defined in the top wall 211 of the shell 21. The wind guide tongue 6 is disposed between the air outlet 3 and the air outlet 4. That is, the second end of the wind guide tongue 6 is disposed between the air outlet 3 and the air outlet 4. The wind guide tongue 6 divides the receiving cavity 5 into a first air duct 51 and a second air duct 52. The first air duct 51 is communicated with the air outlet 3, and the second air duct 52 is communicated with the air outlet 4.

The air outlet 3 and the air outlet 4 are spaced apart from each other. A blind hole 9 is defined between the air outlet 3 and the air outlet 4. The air outlet 3 includes two sub-outlets, and a gap is defined between the two sub-outlets. The air outlet 4 includes three sub-outlets, the three sub-outlets are spaced apart from each other, and a gap is defined between every two adjacent sub-outlets.

The receiving cavity 5 is defined to further receive an air guide plate 7 and a partition plate 8. Two ends of the air guide plate 7 are connected to the top wall 211 and the bottom wall 212 of the shell 21 respectively, and two ends of the partition plate 8 are connected to the top wall 211 and the bottom wall 212 of the shell 21 respectively. The air guide plate 7 and the partition plate 8 are disposed on two opposite sides of the fan assembly 22. A connection position between the air guide plate 7 and the top wall 211 of the shell 21 is disposed at a relative outer side of the air outlet 4 away from the air outlet 3. A connection position between the partition plate 8 and the top wall 211 of the shell 21 is disposed at a relative outer side of the air outlet 3 away from the air outlet 4. When the neck fan is worn, a connection position between the air guide plate 7 and the bottom wall 212 of the shell 21 and a connection position between the partition plate 8 and the bottom wall 212 of the shell 21 are disposed below the fan assembly 22. A gap is defined between the connection position between the air guide plate 7 and the bottom wall 212 of the shell 21 and the connection position between the partition plate 8 and the bottom wall 212 of the shell 21. The air guide plate 7 and the partition plate 8 are arranged inclined with respect to each other, such that the air guide plate 7 and the partition plate 8 can guide the airflow. The air guide plate 7 and the top wall 211 cooperatively define a second air duct 52, and the wind guide tongue 6 is received in the second air duct 52. More specifically, the air guide plate 7, the top wall 211, and the wind guide tongue 6 cooperatively define the second air duct 52. The partition plate 8 and the top wall 211 cooperatively define a first air duct 51. The fan assembly 22 is received in the first air duct 51. More specifically, the fan assembly 22, the partition plate 8, and the top wall 211 cooperatively define the first air duct 51. In other words, the wind guide tongue 6, the bottom wall 212, the partition plate 8, and the top wall 211 cooperatively define the first air duct 51.

According to the present embodiment, the receiving cavity 5 is defined to receive the wind guide tongue 6. The wind guide tongue 6 divides the v cavity 5 into the first air duct 51 and the second air duct 52. The first air duct 51 communicates with the air outlet 3, and the second air duct 52 communicates with the air outlet 4. The fan assembly 22 is received in the first air duct 51. The air flowing out of the fan assembly 22 flows through the wind guide tongue 6 to the first air duct 51 and the second air duct 52 respectively, such that the air may flow out of the shell 21 from the air outlet 3 and the air outlet 4. The wind guide tongue 6 is configured to guide the air flowing directions. The air flowing out of the fan assembly 22 is directed to the air outlet 3 and air outlet 4 respectively after being guided by the wind guide tongue 6, such that the air may flow out of the neck fan from both the air outlet 3 and the air outlet 4, increasing the area covered by the air flowing out of the shell 21, and the structure of the neck fan may be more appropriate. Further, the wind guide tongue 6 is configured to control the air flowing direction. The wind guide tongue 6 controls the air flowing out of the fan assembly 22 to flow to the air outlet 3 and the air outlet 4 respectively, such that the air may uniformly flow through the air outlet 3 and the air outlet 4, enabling the air flowing intensity at the air outlet 3 and that at the air outlet 4 to be of equal, improving the user's experience.

FIGS. 77-80 show a neck fan according to another embodiment of the present disclosure.

As shown in FIGS. 77-80, an air outlet assembly 80 includes: a first engaging cover 10, a second engaging cover 20, a battery holder 30, a battery 40 and a fan assembly 50. The second engaging cover 20 is connected to the first engaging cover 10 by embedding, and the second engaging cover 20 and the first engaging cover 10 cooperatively define a first receiving cavity 60. The battery holder 30 is received in the first receiving cavity 60. A second receiving cavity 61 is defined by the battery holder 30 and the second engaging cover 20. A side of the battery holder 30 facing the first engaging cover 10 defines a first receiving slot 31. The battery 40 is received in the first receiving slot 31. The fan assembly 50 is received in the first receiving cavity 60. The fan assembly 50 is connected to the second receiving cavity 61, and the fan assembly 50 and the second receiving cavity 61 are disposed on a same side of the battery holder 30.

In air outlet assembly 80 of the present embodiment, the side of the battery holder 30 facing the first engaging cover 10 defines the first receiving slot 31, such that the battery 40 is fixed. The fan assembly 50 is received in the first receiving cavity 60, and is connected to the second receiving cavity 61, such that the battery 40 and the fan assembly 50 are fixed at two separated layers, allowing the battery holder 30 to restrict and fix the battery 40 and to facilitate the air out of the fan assembly 50 to flow to the second receiving cavity 61. The fan assembly 50 extends through the battery holder 30, or the fan assembly 50 is located on a same side of the battery holder 30. In this way, the airflow of fan assembly 50 may be guided to flow between the battery holder 30 and the second engaging cover 20, optimally utilizing the space where the fan assembly 50 and the battery holder 30 are arranged, and reducing an impact in an air guiding area of the fan assembly 50 caused by the battery holder 30.

Figure 78:
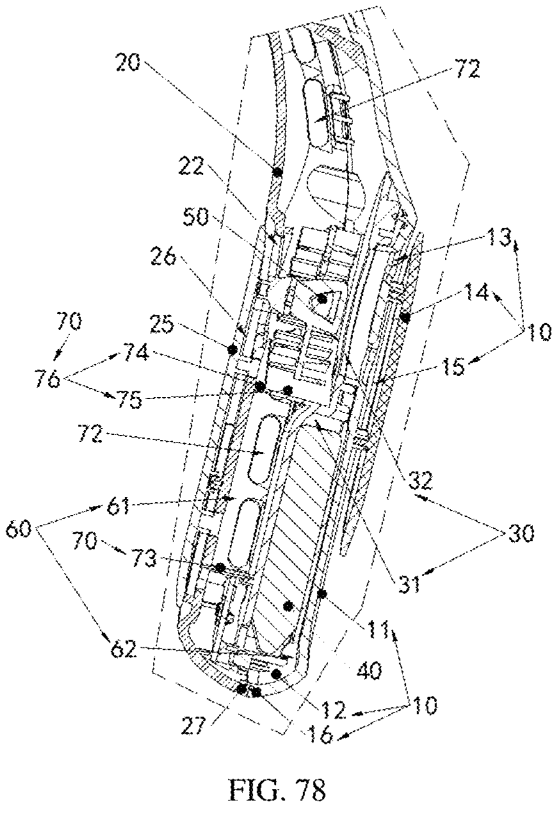
FIG. 78 is a cross section view of a portion of the neck fan shown in FIG. 77.
Figure 79:
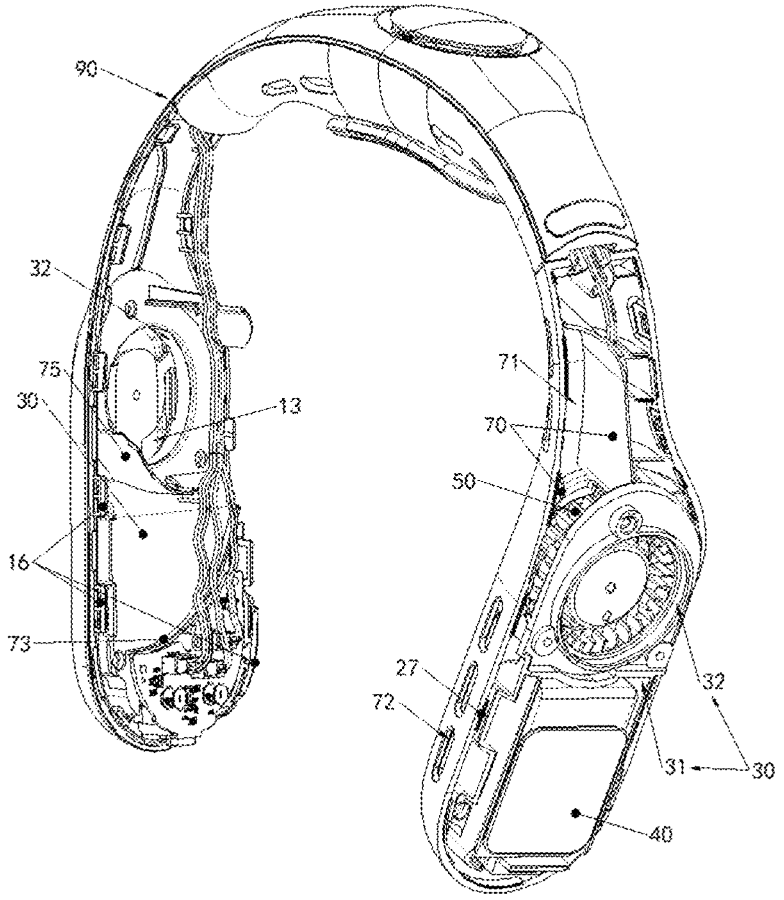
FIG. 79 is a first exploded view of the neck fan shown in FIG. 77.
Figure 80:
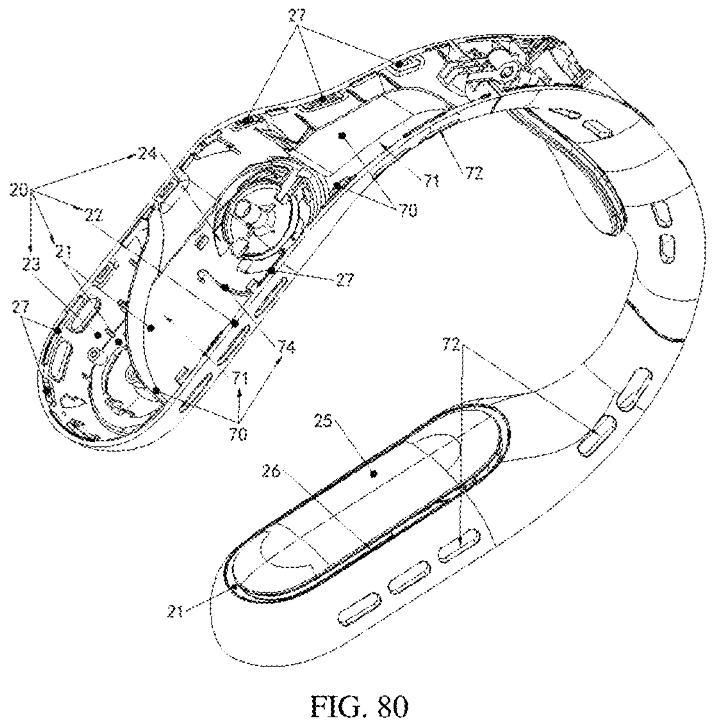
FIG. 80 is a second exploded view of the neck fan shown in FIG. 77.

As shown in FIGS. 78-80, in an embodiment, the battery holder 30 further includes a through hole 32. A third receiving cavity 62 is defined between the battery holder 30 and the first engaging cover 10. The second receiving cavity 61 is communicated with the third receiving cavity 62 through the through hole 32.

In detail, since the second receiving cavity 61 is communicated to the third receiving cavity 62 through the through hole 32, the air guiding area of the fan assembly 50 may be increased, reducing the impact in the air guiding area of the fan assembly 50 caused by the battery holder 30. Further, the battery 40 in the first receiving slot 31 may be cooled, ensuring the battery 40 to be used safely.

As shown in FIGS. 78-80, in an embodiment, the fan assembly 50 is received in the through hole 32. The fan assembly 50 is connected to the second receiving cavity 61 and the third receiving cavity 62 through the through hole 32. An axis of the fan assembly 50 coincides with an axis of the through hole 32.

In detail, the axis of the fan assembly 50 coincides with the axis of the through bore 32, such that the air guiding area occupied by the fan assembly 50 may be reduced.

As shown in FIGS. 77-80, in an embodiment, the first engaging cover 10 includes a top wall 11 and a third side wall 12. The third side wall 12 extends around and is fixed on the top wall 11. The top wall 11 defines a first air inlet 13. The first air inlet hole 13 is covered by a first stopper 14. A first gap 15 is defined between the first stopper 14 and the top wall 11. The first gap 15 intersects with an axis of the first air inlet 13. The first receiving cavity 60 is communicated with the first gap 15 through the first air inlet 13. The bottom wall 21 defines a second air inlet 24. The second air inlet 24 is covered by a second stopper 25. A second gap 26 is defined between the second stopper 25 and the bottom wall 21. The second gap 26 intersects an axis of the second air inlet 24. The second receiving cavity 61 is communicated to the second gap 26 through the second air inlet 24.

In detail, defining the first air inlet 13 and the first gap 15 allows the third receiving cavity 62 to receive the external air, and defining the second air inlet 24 and the second gap

26 allows the second receiving cavity 61 to receive external air, such that the fan assembly 50 is able to intake the external air. Further, the first stopper 14 covers the first air inlet 13, the first gap 15 is defined between the first stopper 14 and the top wall 11, and the first gap 15 intersects with the axis of the first air inlet 13, such that the user's hair or foreign matter may be prevented from being sucked directly into the first receiving cavity 60, preventing the user's hair or the foreign matters from winding the fan assembly 50, ensuring the fan assembly 50 to operate normally.

As shown in FIG. 78, the axis of the first inlet 13, the axis of the through hole 32 and the axis of the second inlet 24 coincide with each other, allowing the fan assembly 50 in the through hole 32 to intake the external air from the first inlet 13 and the second inlet 24.

Further, the second inlet 24 may also serve as an air outlet, increasing the area covered by the air flowing out of the air outlet assembly 80.

As shown in FIGS. 78-80, in an embodiment, the second receiving cavity 61 receives a plurality of air guide members 70. The air guide members 70 abut against the battery holder 30, such that the air guide members 70 and the battery holder 30 cooperatively define an air guide channel 71. The second engaging cover 20 defines a plurality of air flowing holes 72 communicating with the air guide channel 71.

Defining the air guide channel 71 and the plurality of air flowing holes 72 allows the fan assembly 50 to be communicated with the external air, such that the air flowing out of the fan assembly 50 flows to the external through the air guide channel 71 and the air flowing holes 72.

In detail, as shown in FIGS. 78-80, in an embodiment, the air guide member 70 is arranged with a first air guide plate 73 and a second air guide plate 74. A bottom of the first air guide plate 73 and a bottom of the second air guide plate 74 are fixed to the second engaging cover 20. A top of the first air guide plate 73 abuts against the battery holder 30. A third air guide plate 75 is arranged on and protruding from a bottom of the battery holder 30. The second air guide plate 74 and the third air guide plate 75 abut against each other and cooperatively define a fourth air guide plate 76. A gap is defined between the first air guide plate 73 and the fourth air guide plate 76. The second engaging cover 20, the first air guide plate 73, the fourth air guide plate 76 and the battery holder 30 cooperatively define the air guide channel 71. The fan assembly 50 is communicated with the air flowing holes 72 through the air guide channel 71.

The second engaging cover 20, the first air guide plate 73, the fourth air guide plate 76 and the battery holder 30 cooperatively define the air guide channel 71, such that the fan assembly 50 is communicated with the air flowing holes 72. Further, the second air guide plate 74 abuts against the third air guide plate 75, and the second air guide plate 74 and the third air guide plate 75 are spliced to serve as the fourth air guide plate 76, ensuring the air guide channel 71 to be used normally. In addition, connection the battery holder 30 and the second engaging cover 20 may be more fixed.

Further, in an embodiment, the second air guide plate 74 is arranged a protrusion, and the third air guide plate 75 defines a recess. The protrusion is inserted to the recess for connection. In this way, the second air guide plate 74 and the third air guide plate 75 are spliced together to serves as the fourth air guide plate 76.

In detail, as shown in FIG. 80, in some embodiments, the second engaging cover 20 includes a bottom wall 21 and a first side wall 22 and a second side wall 23. The first side wall 22 and the second side wall 23 extend out of the bottom wall 21 and are opposite to each other. The fourth air guide plate 76 surrounds the fan assembly 50. Each of the first air guide plate 73 and the second air guide plate 74 extends to be fixed to the bottom wall 21. An end of the second air guide plate 74 is connected to the first side wall 22, and a gap is defined between the other end of the second air guide plate 74 and the second side wall 23. Two ends of the first air guide plate 73 is connected to the first side wall 22 and the second side wall 23 respectively.

In the present embodiment, the end of the second air guide plate 74 is connected to the first side wall 22, and the gap is defined between the other end of the second air guide plate 74 and the second side wall 23. Further, the second air guide plate 74 abuts against the third air guide plate 75, and the second air guide plate 74 and the third air guide plate 75 are spliced together to serves as the fourth air guide plate 76. In this way, the air guide channel 71 may be used normally. Further, the fourth air guide plate 76 surrounds the fan assembly 50, preventing the fan assembly 50 form communicating with the air flowing holes 72 in a linear straight direction. Therefore, foreign matters are prevented from entering through the air flowing holes 72, and that is, the fan assembly 50 may be prevented from being wound by the foreign matters, ensuring the fan assembly 50 to operate normally.

In some embodiments, the plurality of air flowing holes 72 are distributed on a same side of the fan assembly 50, such that only one air guide member 70 is arranged.

Figure 77:
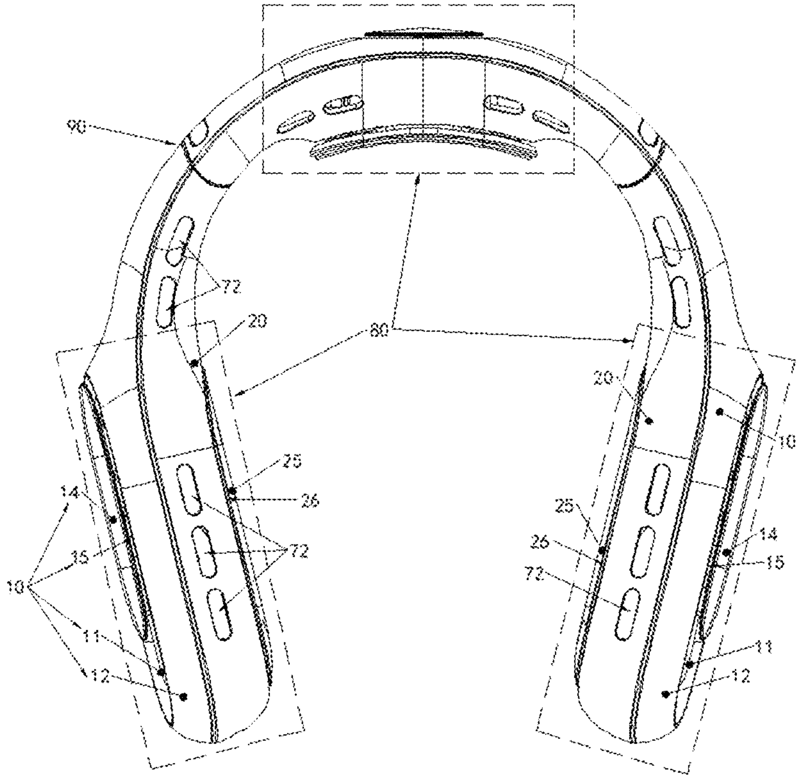
FIG. 77 is a schematic view of a neck fan according to an embodiment of the present disclosure.

As shown in FIGS. 77, and 79-80, in an embodiment, the plurality of air flowing holes 72 are divided into two groups, and the two groups are distributed on two sides of the fan assembly 50, respectively. Each of two sides of the fan assembly 50 is arranged with one air guide member 70. Further, two corresponding the air guide channels 71 are defined.

In detail, two air guides members 70 on the two sides of the fan assembly 50 have a same structure. Each of the two air guide members 70 is formed by the first air guide plate 73 and the fourth air guide plate 76. Alternatively, one of the two air guide members 70 is formed by the first air guide plate 73 and the fourth air guide plate 76, and the other one of the two air guide members 70 is formed by two first air guide plates 73. A side of the fan assembly 50 is indirectly connected to a first group of the air flowing holes 72 through the fourth air guide plate 76. The other side of the fan assembly 50 is connected to the second group of air flowing holes 72 through the first air guide plate 73. In this way, the fan assembly 50 may be prevented from being wound by the foreign matters, ensuring the fan assembly 50 to operate safely.

In addition to the above embodiment, each of the first side wall 22 and the second side wall 23 is arranged with a first embedding member 27. The third side wall 12 is arranged with a second embedding member 16. The first embedding member 27 may be connected to the second embedding member 16 by embedding. In this way, the first engaging cover 10 and the second engaging cover 20 are connected by embedding.

According to the air outlet assembly 80 in the present disclosure, the battery 40 is received in the first receiving slot 31, preventing the battery 40 from shaking in the first receiving cavity 60. The fan assembly 50 is received in the first receiving cavity 60, and the fan assembly 50 and the second receiving cavity 61 are connected, such that the battery 40 and the fan assembly 50 are fixed in separated layers. In this way, the battery holder 30 may limit and fix the battery 40 and facilitate the air flowing out of the fan assembly 50 to flow to the second receiving cavity 61. The fan assembly 50 extends through the battery holder 30 or is disposed on a same side of the battery holder 30, allowing the air out of the fan assembly to flow between the battery holder 30 and the second engaging cover 20. In this way, spaces for arranging the fan assembly 50, the battery holder 30, and the like, may be utilized optimally, reducing the impact in the air guiding area of the fan assembly caused by the battery holder 30.

As shown in FIGS. 77-80, the neck fan further includes a suspension member 90 and at least one of the above-mentioned air outlet assembly 80. The air outlet assembly 80 is arranged on the suspension member 90.

In detail, the battery holder 30 is arranged in the air outlet assembly 80, such that the battery 40 and the air guide channel 71 are arranged in separated layers. In this way, the battery 40 is limited and fixed, and spaces for arranging the fan assembly 50, the battery holder 30, and the battery 40, may be utilized optimally, reducing the impact in the air guiding area of the fan assembly 50. The battery 40 may be fixedly arranged, and the fan assembly 50 may be assisted to guide the air flowing.

As shown in FIGS. 77-80, in some embodiments, the neck fan of the present disclosure includes two air outlet assemblies 80. The two air outlet assemblies 80 are arranged at two ends of the suspension member 90. In another embodiment, the neck fan of the present disclosure includes three air outlet assemblies 80. The three air outlet assemblies 80 are arranged at each of two ends of the suspension member 90 and at a middle of the suspension member 90, respectively. In this case, the suspension member 90 may be arch-shaped. The air guiding area of the neck fan is increased.

Figure 81:
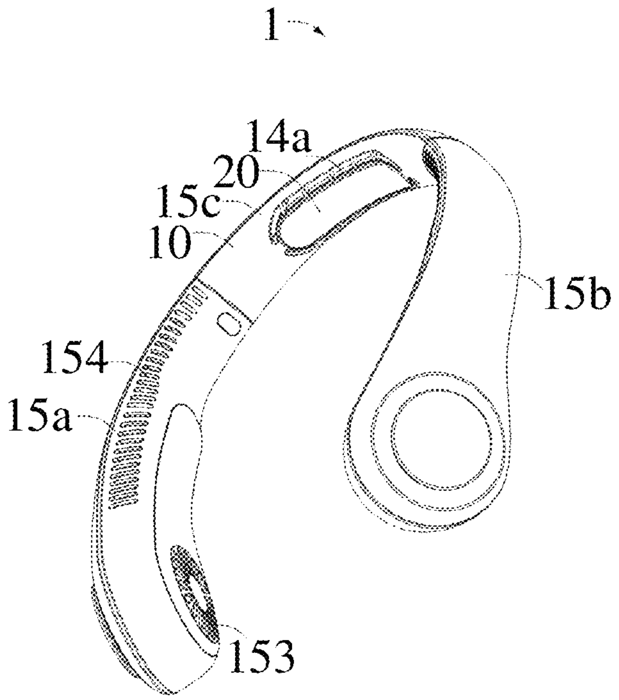
FIG. 81 is a schematic view of a temperature adjustment apparatus that hang around a user's neck according to an embodiment of the present disclosure.
Figure 82:
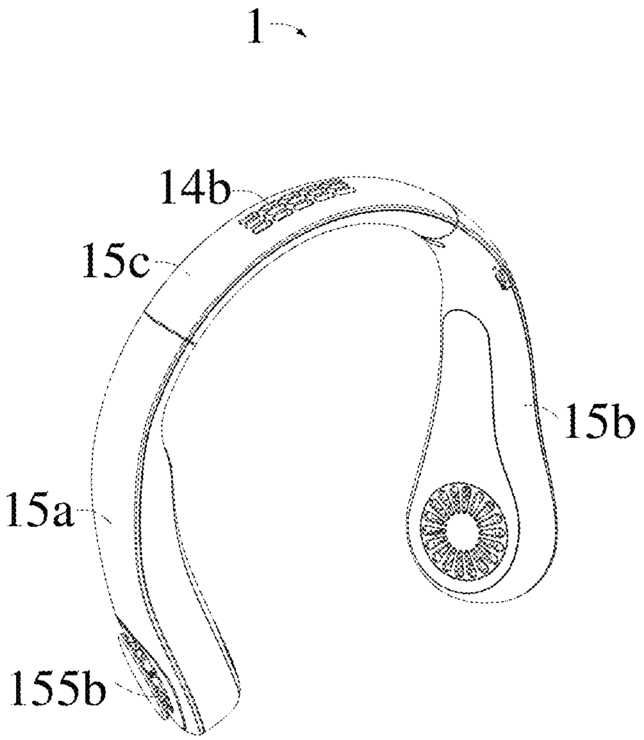
FIG. 82 is another schematic view of the temperature adjustment apparatus shown in FIG. 81.
Figure 83:
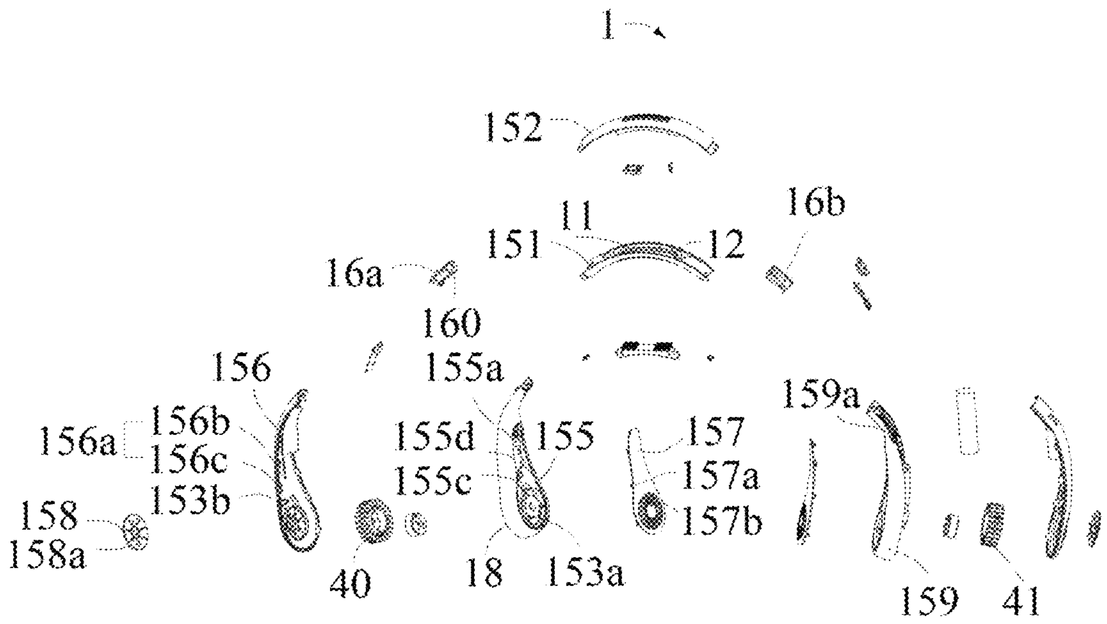
FIG. 83 is an exploded view of the temperature adjustment apparatus shown in FIG. 81.
Figure 84:
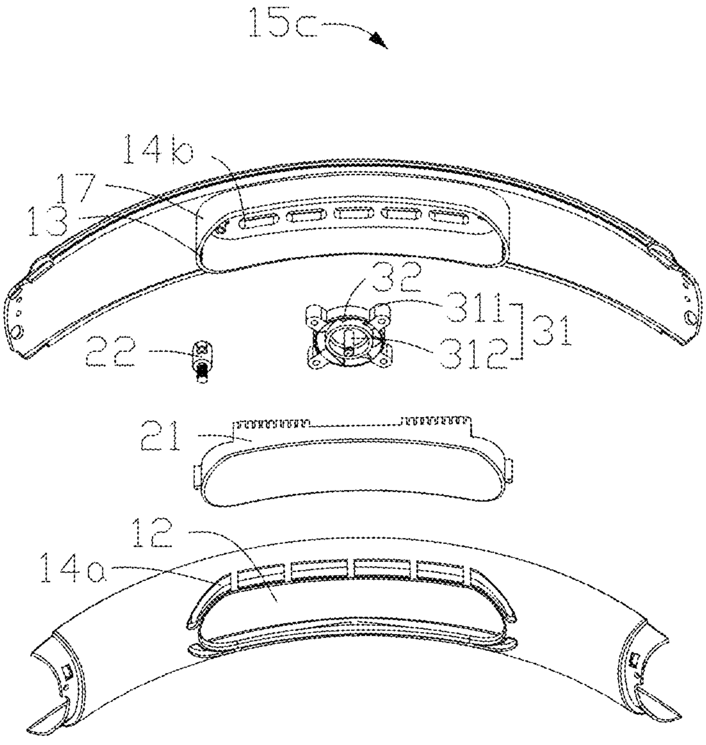
FIG. 84 is an exploded view of a middle portion of the temperature adjustment apparatus shown in FIG. 81.
Figure 85:
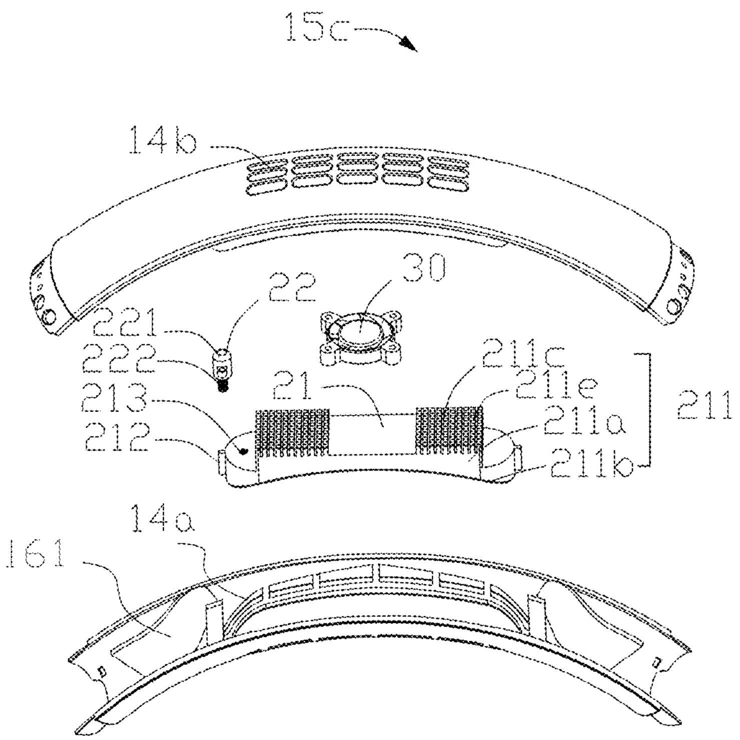
FIG. 85 is another exploded view of a middle portion of the temperature adjustment apparatus shown in FIG. 81.
Figure 86:
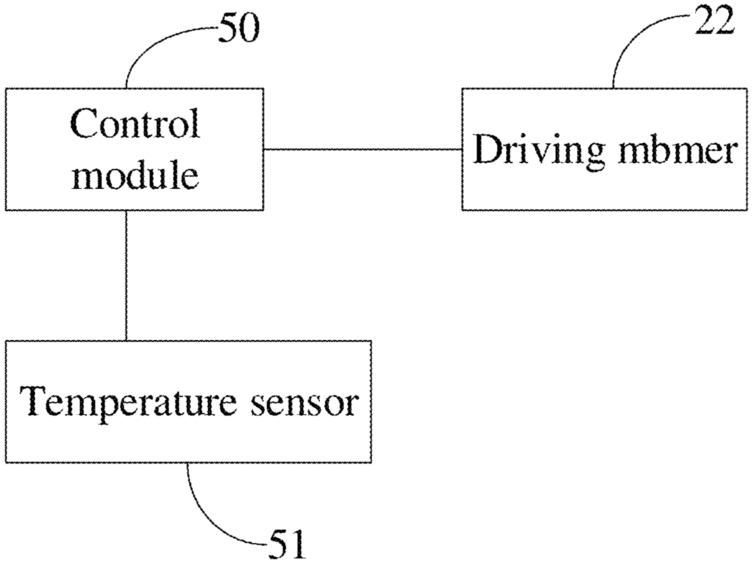
FIG. 86 is a diagram of a circuit of the temperature adjustment apparatus shown in FIG. 81.

As shown in FIGS. 81-86, FIG. 81 is a schematic view of a neck fan 1 according to another embodiment of the present disclosure. The neck fan 1 may serve as a temperature adjustment apparatus 1 that hangs around a user's neck, FIG. 82 is another schematic view of the temperature adjustment apparatus 1 shown in FIG. 81, FIG. 83 is an exploded view of the temperature adjustment apparatus 1 shown in FIG. 81, FIG. 84 is an exploded view of a middle portion 15*c* of the temperature adjustment apparatus 1 shown in FIG. 81, and FIG. 85 is another exploded view of the middle portion 15*c* of the temperature adjustment apparatus 1 shown in FIG. 81. The temperature adjustment apparatus 1, which can be worn by a user to hang around the user's neck, includes an arc-shaped shell 10 and a movable temperature adjustment assembly 20. FIG. 86 is a diagram of a circuit of the temperature adjustment apparatus 1 shown in FIG. 81.

The arc-shaped shell 10 is wearable around the neck. The arc-shaped shell 10 has a first receiving cavity 11 and a first opening 12 communicated with the first receiving cavity 11 and oriented towards the neck. The movable temperature adjustment assembly 20 includes a temperature adjustment member 21 and a driving member 22. The temperature adjustment member 21 is mounted corresponding to the first opening 12. The driving member 22 is connected to the arc-shaped shell 10 and the temperature adjustment member 21. The temperature adjustment member 21 is configured to absorb heat emitted from the neck, such that the temperature adjustment member 21 may cool the neck. In some embodiments, the temperature adjustment member 21 may be configured to release heat to warm the neck. The driving member 22 is configured to drive the temperature adjustment member 21 to move, such that the temperature adjustment member 21 may be switched between an extended state and a retracted state. In the extended state, the temperature adjustment member 21 extends out of the first opening 12, further extending towards the neck. In the retracted state, at least part of the temperature adjustment member 21 is retracted through the first opening, such that the temperature adjustment member 21 is received in the receiving cavity 11, and the temperature adjustment member 21 is separated from the neck. It shall be understood that, the user may free the user's hands by wearing the arc-shaped shell 10 around the neck, such that the temperature adjustment apparatus 1 hangs around the neck. In this way, the user's neck may be cooled down and/or warmed up by the temperature adjustment apparatus 1 while the user is performing other activities, such that the temperature is adjusted, and at the same time, the user's experience is improved.

According to the present embodiment, for the temperature adjustment apparatus 1, the arc-shaped shell 10 has the first receiving cavity 11 and the first opening 12 communicated to the first receiving cavity 11. The first opening 12 faces towards the user's neck. The temperature adjustment member 21 of the movable temperature adjustment assembly 20 may extend out of the shell through the first opening 12 and face towards the neck to absorb heat from the neck to cool the neck and/or to release heat to warm the neck. In this way, the user may be cooled rapidly at higher temperatures and may be warmed at lower temperatures. Therefore, the temperature adjustment apparatus 1 may be applied to various application scenarios, and the user's experience may be improved. In addition, the shell 10 of the temperature adjustment apparatus 1 is arc-shaped, the temperature adjustment apparatus 1 may be attached to the neck appropriately, enabling the user to feel comfortable, and allowing the user to be cooled and warmed quickly (i.e., an efficiency of increasing or decreasing the temperature may be improved). In addition, the temperature adjustment member 21 is driven by the driving member 22, such that the temperature adjustment member 21 may be switched between the extended state and the retracted state. In the extended state, the temperature adjustment member 21 extends out of the first opening 12, further extending towards the neck. In the retracted state, at least part of the temperature adjustment member 21 is retracted through the first opening, such that the temperature adjustment member 21 is received in the receiving cavity 11, and the temperature adjustment member 21 is separated from the neck. In this way, the temperature adjustment member 21 may be received in the first receiving cavity 11 when not in use, improving the user's experience. More specifically, when the temperature adjustment member 21 contacts the neck for a certain period of time, a temperature of the temperature adjustment member 21 gradually tends to be the same as a temperature of the neck, such that the user may be gradually insensitive, reducing the user's experience. However, the driving member 22 may control the temperature adjustment member 21 to be extended or retracted, the temperature adjustment member 21 may be controlled to touch the neck at time intervals. For example, when the user does not feel about the temperature adjustment apparatus, the temperature adjustment member 21 may be controlled to be in the retracted state for a period of time. When the temperature of the temperature adjustment member 21 is different from the temperature of the neck, then the temperature adjustment member 21 may be controlled to be extended to contact the neck. In this way, the user may feel an obvious temperature difference, improving the user's experience.

Further, as shown in FIG. 86, the temperature adjustment apparatus 1 may further include a control module 50. The control module 50 is electrically connected to the driving member 22. The control module 50 is configured to control the driving member 22 to drive the temperature adjustment member 21 to move. The temperature adjustment apparatus 1 may further include a temperature sensor 51. The temperature sensor 51 may be arranged on the temperature adjustment member 21 to detect the temperature of the temperature adjustment member 21 and output a temperature detection signal. The control module 50 is configured to receive the temperature detection signal and control the driving member 22 to drive the temperature adjustment member 21 to move based on the temperature detection signal. The control module 50 is configured to determine whether the temperature of the temperature adjustment member 21 is greater than or equal to a predetermined temperature based on the temperature detection signal. When the temperature of the temperature adjustment member 21 is greater than or equal to the predetermined temperature, the control module 50 controls the driving member 22 to drive the temperature adjustment member 21 to enter and stay in the retracted state. When the temperature of the temperature adjustment member 21 is less than or equal to the predetermined temperature, the control module 50 controls the driving member 22 to drive the temperature adjustment member 21 to enter and stay in the extended state. It shall be understood that the control module 50 may control the driving member 22 to drive the temperature adjustment member 21 to move, such as controlling the temperature adjustment member 21 to extend or retract periodically. Alternatively, the driving member may drive the temperature adjustment member 21 to extend or retract based on the user's instructions or preferences (such as a button pressed by the user, a voice instruction, a gesture instruction, and so on). In this way, demands of various users may be satisfied, improving the user's experience. Further, the temperature sensor 51 detects the temperature of the temperature adjustment member 21 and controls the temperature adjustment member 21 to be extended or retracted based on the temperature of the temperature adjustment member 21. In this way, the temperature adjustment member 21 may be controlled in a more intelligent manner, improving the user's experience.

Further, the temperature adjustment member 21 includes a semiconductor cooler 211. The semiconductor cooler 211 includes a semiconductor cooling structure 211*a*, a thermal conductor 211*b*, and a heat dissipator 211*c*. The thermal conductor 211*b* is connected to a cool end of the semiconductor cooling structure 211*a* and is configured to contact the user's neck. The heat dissipator 211*c* is connected to a warm end of the semiconductor cooling structure 211*a*. The thermal conductor 211*b* includes a metal thermal conductor 211*b*. The heat dissipator 211*c* includes a plurality of heat dissipating fins 211*e*. The temperature adjustment member 21 further includes a first sliding structure 212 arranged on the semiconductor cooler 211. For example, in the present embodiment, at least two first sliding structures 212 may be arranged. The arc-shaped shell is arranged with a second sliding structures 13 corresponding to the first sliding structure 212. For example, in the present embodiment, at least two second sliding structures 212 may be arranged. The driving member 22 is configured to drive the temperature adjustment member 21, such that the first sliding structure 212 slides relative to the second sliding structure 13, and therefore, the temperature adjustment member 21 is switched between the extended state and the retracted state. One of the first sliding structure 212 and the second sliding structure 13 includes a slide groove, and the other one of the first sliding structure 212 and the second sliding structure 13 includes a slide block. The slide block may be received in the slide groove and slidable along the slide groove. The number of first sliding structures 212 may be two, and the number of second sliding structures 13 may be two. The two first sliding structures 212 may be opposite to each other. In the present embodiment, the second sliding structure 13 defines a slide groove. The first sliding structure 212 includes a slide block. The slide block may be received in the slide groove and slidable along the slide groove. When the temperature is low, and the user needs to be warmed, the first sliding structure 212 slides out of the second sliding structure 13, such that the temperature adjustment member 21 is in the extended state and near the neck, and the neck is warmed by the thermal conductor 211*b*. When the temperature is high, and the user needs to be cooled, the first sliding structure 212 slides out of the second sliding structure 13, such that the temperature adjustment member 21 is in the extended state and close to the neck, the warm may be cooled by the heat dissipator 211*c*. When the neck temperature adjustment apparatus 1 is not in use, the first sliding structure 212 slides into the second sliding structure 13, such that the temperature adjustment member 21 is in the retracted state, and the temperature adjustment apparatus may be easily stored and carried. According to the present embodiment, the thermal conductor 211*b* includes the metal thermal conductor 211*b*. The heat dissipator 211*c* includes the plurality of heat dissipating fins 211*e*, a heat conducting efficiency and a heat dissipating efficiency may be increased, such that the user may be cooled or warmed quickly. In addition, since two first sliding structures 212 are arranged oppositely, and two second sliding structures 13 are arranged oppositely, the temperature adjustment member 21 may be stable while being lifted and lowered. One of the first sliding structure 212 and the second sliding structure 13 includes the slide groove, and the other of the first sliding structure 212 and the second sliding structure 13 includes the slide block. The slide block may be received in the slide groove and slidable along the slide groove. The slide block sliding in the slide groove allows the first sliding structure 212 to slide stably in the second sliding structure 13.

Further, the driving member 22 includes a motor 221 and a motor shaft 222 connected to the motor 221. The motor 221 is fixed to the arc-shaped shell 10. The motor shaft 222 has an external thread. The temperature adjustment member 21 defines a thread hole 213. The external thread of the motor shaft 222 engages with an internal thread arranged on a wall of the thread hole 213. In this way, when the motor 221 drives the motor shaft 222 to rotate, the temperature adjustment member 21 moves along the motor shaft 222, such that the temperature adjustment member is switched between the extended state and the retracted state. The motor 221 may be a stepper motor 221. In the present embodiment, the driving member 22 includes the motor 221 and the motor shaft 222 connected to the motor 221. The motor 221 is fixed to the arc-shaped shell 10. The motor shaft 222 has the external thread. The temperature adjustment member 21 defines the thread hole 213. The external thread of the motor shaft 222 engages with the internal thread arranged on the wall of the thread hole 213. In this way, the driving member 22, the temperature adjustment member 21, and the arc-shaped shell 10 are fixedly connected with each other. In addition, the thread of the motor shaft 222 engages with the inner thread of the thread hole 213, such that the motor 221 controls the temperature adjustment member 21 to be extended and retracted. The structure of the temperature adjustment apparatus may be simplified and may be manipulated stably.

Further, the arc-shaped shell further defines a plurality of first through holes 14*a*. The plurality of first through holes 14*a* are distributed surrounding an outer periphery of the first opening 12. The arc-shaped shell further defines a plurality of second through holes 14*b* located on a side of the movable temperature adjustment assembly 20 away from the neck. The temperature adjustment apparatus 1 further includes a first fan assembly 30. The first fan assembly 30 is received in the first receiving cavity 11 and is disposed on the side of the movable temperature adjustment assembly 20 away from the neck. The first fan assembly 30 is configured to blow air towards the first through holes 14*a* and/or the second through holes 14*b*. The first fan assembly 30 is disposed corresponding to a middle region of the movable temperature adjustment assembly 20. The first fan assembly 30 includes a first mounting member 31 and a first blade assembly 32. The first mounting member 31 has a first mounting body 311 and a first mounting shaft 312. The first mounting body 311 is connected to the arc-shaped shell 10. The first mounting shaft 312 is connected to a side of the first mounting body 311 near the movable temperature adjustment assembly 20. The blade assembly is mounted on the first mounting shaft 312. When the temperatures is high, and when the user needs to be cooled, the first fan assembly 30 blows out wind through the second through holes 14*b* to dissipate heat generated from the heat dissipator 211*c*, allowing the heat dissipator 211*c* to be cooled quickly. When the temperature is low, and when the user needs to be warmed, the fan assembly 30 blows out hot air through the through holes 14*a*, allowing the thermal conductor 211*b* to conduct heat to the user. According to the present embodiment, the fan assembly 30 is arranged to operate together with the temperature adjustment member 21. When the user needs to be cooled, the wind is blown to the second through holes 14*b*, increasing a heat dissipating efficiency. When the user needs to be warmed, the hot air is blown to the first through holes 14*a*, increasing a thermal conducting efficiency. In this way, the user may feel comfortable in various temperature.

Further, the arc-shaped shell includes a first portion 15*a*, a second portion 15*b* and a middle portion 15*c* connected between the first portion 15*a* and the second portion 15*b*. The middle portion 15*c* defines the first receiving cavity 11 and the first opening 12. The first portion 15*a* and the second portion 15*b* are configured to be located on two opposite sides of the neck. The middle portion 15*c* extends in an arc direction and includes a first arc member 151 and a second arc member 152. The first arc member may be near the neck when the shell is worn to the user. The second arc member 152 may be away from the neck when the shell is worn to the user. A cross section of the first arc member 151 taken by a plane perpendicular to the arc direction may be arc shaped, protruding towards the user's neck. A cross section of the second arc member 152 taken by the plane perpendicular to the arc direction may be arc shaped, protruding away from the user's neck. A space between the first arc member 151 and the second arc member 152 may be the first receiving cavity 11. The first opening 12 extends through the first arc member 151 and communicates with the first receiving cavity 11. Since the cross section of the first arc member 151 taken by the plane perpendicular to the arc direction may be arc shaped, protruding towards the user's neck, and the cross section of the second arc member 152 taken by the plane perpendicular to the arc direction may be arc shaped, protruding away from the user's neck, the user may feel comfortable when wearing the temperature adjustment apparatus 1 around the neck.

Further, the middle portion 15*c* further includes a ring-shaped extending plate 17. The extending plate 17 is connected to a side of the second arc member 152 near the first arc member 151. The extending plate 17 may be disposed to surround an outer periphery of the movable temperature adjustment apparatus. The arc-shaped shell 10 may further include a first connection member 16*a* and a second connection member 16*b*. The first connection member 16*a* may be connected between the first portion 15*a* and the middle portion 15*c*. The second connection member 16*b* may be connected between the second portion 15*b* and the middle portion 15*c*. According to the present embodiment, the middle portion 15*c* further includes the ring-shaped extending plate 17. The extending plate 17 is connected to the side of the second arc member 152 near the first arc member 151. The extending plate 17 may be disposed to surround the outer periphery of the movable temperature adjustment assembly 20. In this way, a position of the movable temperature adjustment assembly 20 may be restricted, ensuring the temperature adjustment assembly 20 to be stability and accurately switched between the extended state and the retracted state.

Further, each of the first portion 15*a* and the second portion 15*b* defines a second receiving cavity 18. Each of the first portion 15*a* and the second portion 15*b* defines an air inlet 153 and an air outlet 154. The air inlet 153 and the air outlet 154 may be communicated with the second receiving cavity 18. The temperature adjustment apparatus 1 may further include at least two fan assemblies 40. Each of the second receiving cavity 18 of the first portion 15*a* and the second receiving cavity 18 of the second portion 15*b* receives one of the at least two fan assemblies 40. Each fan assembly 40 is configured to drive the air from the air inlet 153 to flow to the corresponding air outlet 154. Since the fan assembly 40 drives the air from the air inlet 153 to flow to the corresponding air outlet 154, the user may be cooled quickly, increasing the efficiency of reducing the temperature.

Further, each of the first connection member 16*a* and the second connection member 16*b* includes a through hole 160, extending through the first connection member 16*a* and the second connection member 16*b*, respectively. The through hole 160 of the first connection member 16*a* is communicated between the second receiving cavity 18 of the first portion 15*a* and the first receiving cavity 11. The through hole 160 of the second connection member 16*b* is communicated between the second receiving cavity 18 of the second portion 15*b* and the first receiving cavity 11. Each of the fan assembly 40 in the first portion 15*a* and the fan assembly 40 in the second portion 15*b* is further configured to drive the air from the air inlet 153 to flow through the corresponding second receiving cavity 18, the corresponding through hole 160, the first receiving cavity 11, to reach the first through holes 14*a*. It shall be understood that, defining the through hole 160 allows the air in the first portion 15*a* and the second portion 15*b* to flow through the through hole 160 to reach the first receiving cavity 11. Subsequently, the air is further blown out of the shell through the first through holes 14*a* of the middle portion 15*c*. In this way, the neck may be cooled effectively. In addition, a wind guide plate 161 may be received in the first receiving cavity 11 of the middle portion 15*c*. The wind guide plate 161 is further configured to guide the air from the through hole 160 to flow to the first through hole 14*a*, allowing the air to be blown out, increasing the air out flowing efficiency.

Further, the second fan assembly 40 includes turbine blades 41 rotating in a predetermined direction. The air inlet 153 may include a first air inlet 153*a* and a second air inlet 153*b*. The first air inlet 153*a* and the second air inlet 153*b* are arranged along the predetermined direction, and are disposed between two opposite sides of the second fan assembly 40. Each of the first portion 15*a* and the second portion 15*b* includes an inner wall 155, an outer wall 156, and a connection wall 159. The inner wall 155, the outer wall 156, and the connection wall 159 cooperatively define the second receiving cavity 18. The outer wall 156 is opposite to the inner wall 155. The connection wall 159 is connected between the inner wall 155 and the outer wall 156. The first air inlet 153*a* is defined in the inner wall 155. The second air inlet 153*b* is defined in the outer wall 156. The connection wall 159 includes a top wall 159*a* facing towards the user's head. The air outlet 154 is defined in the top wall 159*a*. In the present embodiment, a plurality of air outlets 154 are defined. A first portion of the plurality of air outlets 154 are distributed near the middle portion 15*c*, and a second portion of the plurality of air outlets 154 are distributed away from the middle portion 15*c*. A size of the first portion of the plurality of air outlets 154 is less than a size of the second portion of the plurality of air outlets 154. Turbine blades 41 of two second fan assemblies 40 may intake air from the first air inlets 153*a* and the second air inlets 153*b* at the same time, and drive the air to flow along an air duct in the first portion 15*a* and an air duct in the second portion 15*b* respectively, reaching the air outlets 154. The air may be blown out of the air outlets 154 to directly flow towards the user's head, enabling the user to be cooled efficiently. According to the present embodiment, the first air inlet 153*a* and the second air inlet 153*b* are defined to increase an amount of the air to be taken in, such that an air out flowing efficiency of the second fan assembly 40 may be increased. In the present embodiment, the plurality of air outlets 154 are defined. The size of the first portion of the air outlets 154 near the middle portion 15*c* is less than a size of the second portion of the air outlets 154 away from the middle portion 15*c*. In this way, the air out flowing efficiency is increased, the hair and other foreign matters may not be easily caught by the second fan assembly 40, increasing the user's safety.

Further, each of the first portion 15*a* and the second portion 15*b* includes a first cover 157. A surface of the inner wall 155 facing the user's neck has a first mounting portion 155*a*. The first cover 157 and the first mounting portion 155*a* are mounted fixedly. The first cover 157 covers the first air inlet 153*a*. The first cover 157 defines a plurality of air inlets 157*a*. The plurality of air inlets 157*a* correspond to the plurality of first air inlets 153*a* and are distributed in a ring shape. Each of the first portion 15*a* and the second portion 15*b* includes a second cover 158. A surface of the outer wall 156 away from the neck has a second mounting portion 156*a*. The second cover 158 and the second mounting portion 156*a* are mounted fixedly. The second cover 158 covers the second air inlet 153*b*. An air inlet 155*b* is defined between an edge of the second cover 158 and the first portion 15*a* and between the edge of the second cover 158 and the second portion 15*b*. In this way, the air at an outer side of the temperature adjustment apparatus 1 flows through the air inlet 155*b* to reach the second air inlet 153*b*. Since the air inlet 155*b* is defined between the edge of the second cover 158 and the first portion 15*a* and between the edge of the second cover 158 and the second portion 15*b*, the air that is to be blown out of the shell may be compressed optimally, an air pressure near the second air inlet 153*b* may be greater than an air pressure inside the second receiving cavity 18, such that a negative pressure is generated to push the air out of the second air inlet 153*b* to the second air inlet 153*b*, increasing an air intaking rate. Since the air inlet 155*b* is defined between the edge of the second cover 158 and the first portion 15*a* and between the edge of the second cover 158 and the second portion 15*b*, the air intaking rate is increased, and the hair and other foreign matters may not be easily caught by the second fan assembly 40, improving the user's safety.

Further, the first mounting portion 155*a* includes a first slot portion 155*c* and a first fastening portion 155*d*. The first air inlet 153*a* is defined in a bottom wall of the first slot portion 155*c*. The first fastening portion 155*d* is arranged on the first slot portion 155*c*. The first cover 157 is arranged with a second fastening portion 157*d*, fastening with the first fastening portion 155*d*. The second mounting portion 156*a* includes a second slot portion 156*b* and a third fastening portion 156*c*. The second air inlet 153*b* is defined in a bottom wall of the second slot portion 156*b*. The third fastening portion 156*c* is arranged on the second slot portion 156*b*. The second cover 158 is arranged with a fourth fastening portion 158*a*, fastening with the third fastening portion 156*c*. The arc-shaped shell may include a wind guide plate arranged inside the first portion 15*a* and another wind guide plate arranged inside the second portion 15*b*. The wind guide plate and a wall of the first portion 15*a* cooperatively defines an air duct, and the another wind guide plate and a wall of the second portion 15*b* cooperatively defines another air duct. In this way, the second fan assembly 40 may drive the air from the air inlet 153 to flow through the air duct to reach the air outlet 154. In the present embodiment, the first fastening portion 155*d*, the second fastening portion 157*b*, the third fastening portion 156*c*, and the fourth fastening portion 158*a* are arranged to allow the first mounting portion 155*a* to be fastened with the first cover 157 and to allow the second mounting portion 156*a* to be fastened with the second cover 158. The shell may be assembled easily, and the connection may be stable. Further, wind guide plates are arranged to define the air duct in each of the first portion 15*a* and the second portion 15*b*. The air duct may guide the wind generated by the fan assembly 40, increasing the air out flowing efficiency of the second fan assembly 40.

The above description is only specific implementation of the present disclosure, but the scope of the present disclosure is not limited thereto. Variations or substitutions that is raised by any ordinary skilled person in the art shall be included in the scope disclosed of the present disclosure. Therefore, the scope of the present disclosure shall be subject to the scope of the appended claims.

What is claimed is:

1. A neck fan, configured to be worn around a neck of a user, the neck fan comprising:
- a shell, defining a receiving channel;
- two centrifugal fans, wherein one of the two centrifugal fans is disposed at an end of the receiving channel, and an other one of the two centrifugal fans is disposed at an other end of the receiving channel;
- wherein each of the two centrifugal fans comprises:
- a plurality of blades, wherein the plurality of blades are configured to rotate to intake air from an outside of the centrifugal fan to generate wind; and
- a vortex tongue structure, comprising a pressurizing plate and a wind guiding plate connected to the pressurizing plate, wherein the pressurizing plate is a curved wall arranged around ends of some of the plurality of blades, the wind guiding plate protrudes from and is extending away from an outer surface of the pressurizing plate.

2. The neck fan according to claim 1, wherein each of the two centrifugal fans further comprises:

a motor, wherein the plurality of blades are configured to be driven by the motor to rotate to generate the wind.

3. The neck fan according to claim 1, wherein the neck fan further comprises a partition, received in the receiving channel and dividing the receiving channel into a first channel and a second channel;

the second channel is configured to receive electric components of the neck fan; and the wind guiding plate defines an air channel communicating with the first channel and is configured to guide the wind to flow from the vortex tongue structure to the first channel.

4. The neck fan according to claim 3, wherein the wind guiding plate is spaced apart from the partition.

5. The neck fan according to claim 1, wherein each of the two centrifugal fans comprises two side walls, the two side walls are opposite to each other and are connected to two opposite edges of the curved wall;

the curved wall surrounds and covers ends of the some of the plurality of blades away from the motor;

the curved wall and the two side walls cooperatively define a receiving space, the plurality of blades are received in the receiving space, each of the two side walls defines an air inlet window, the plurality of blades are configured to rotate to intake the air from the air inlet window of each of the two side walls.

6. The neck fan according to claim 5, wherein each of the two centrifugal fans comprises a first wind guiding sub-plate, a second wind guiding sub-plate opposite to the first wind guiding sub-plate, a third wind guiding sub-plate connected between the first wind guiding sub-plate and the second wind guiding sub-plate, and a fourth wind guiding sub-plate connected between the first wind guiding sub-plate and the second wind guiding sub-plate and opposite to the third wind guiding sub-plate;

the first wind guiding sub-plate, the second wind guiding sub-plate, the third wind guiding sub-plate, and the fourth wind guiding sub-plate cooperatively define an air channel communicating with the receiving space; and the plurality of blades are configured to generate the wind from the air intaken from the air inlet window, the pressurizing plate is configured to guide the wind to flow to the air channel from a rest of the plurality of blades uncovered by the pressurizing plate.

7. The neck fan according to claim 6, wherein, the shell comprises:

an inner shell, disposed near the neck and defining a plurality of air outlets;

an outer shell, connected to the inner shell and disposed opposite to the inner shell and away from the neck, wherein the outer shell and the inner shell cooperatively define the receiving channel communicating with the plurality of air outlets;

wherein each of the inner shell and the outer shell defines a plurality of air inlets;

the air inlet window, which is in one of the two side walls disposed near the inner shell, corresponds to and communicate with the plurality of air inlets in the inner shell;

the air inlet window, which is in an other one of the two side walls disposed near the outer shell, corresponds to and communicate with the plurality of air inlets in the outer shell.

8. The neck fan according to claim 7, wherein a first direction in which the air is flowing from the outside of the neck fan into the two centrifugal fans through the plurality of air inlets is parallel to a second direction in which the plurality of blades intake the air from the outside of the centrifugal fan through the air inlet windows; and a third direction to which an opening of the air channel faces is perpendicular to the first direction and the second direction.

9. The neck fan according to claim 1, wherein a cross-sectional area of an air duct is decreased along a direction away from a location where each of the two centrifugal fans is disposed.

10. The neck fan according to claim 1, wherein the pressurizing plate defines a receiving space, an air inlet window, and an air outlet port; the air inlet window and the air outlet port are communicated with the receiving space; the receiving space receives the plurality of blades; the pressurizing plate is configured to pressurize the wind generated by the plurality of blades rotating and to guide the pressurized wind to flow to the air outlet port; the wind guiding plate defines an air channel communicating with the air outlet port of the pressurizing plate.

* * * * *